(12) United States Patent
Kitano et al.

(10) Patent No.: US 6,369,110 B1
(45) Date of Patent: Apr. 9, 2002

(54) SUBSTITUTED GUANIDINE DERIVATIVES AND PROCESS FOR PRODUCING THE SAME

(75) Inventors: Masahumi Kitano; Naohito Ohashi, both of Takatsuki (JP)

(73) Assignee: Sumitomo Pharmaceuticals Company, Osaka (JP)

( * ) Notice: Subject to any disclaimer, the term of this patent is extended or adjusted under 35 U.S.C. 154(b) by 0 days.

(21) Appl. No.: 09/701,269
(22) PCT Filed: May 25, 1999
(86) PCT No.: PCT/JP99/02738
§ 371 Date: Nov. 27, 2000
§ 102(e) Date: Nov. 27, 2000
(87) PCT Pub. No.: WO99/61414
PCT Pub. Date: Dec. 2, 1999

(30) Foreign Application Priority Data

May 26, 1998 (JP) ............................................ 10-144599
Mar. 4, 1999 (JP) ............................................ 11-057589

(51) Int. Cl.[7] ..................... C07C 279/02; A61K 31/155
(52) U.S. Cl. ..................... 514/617; 564/180; 564/237; 514/618; 514/619; 514/620; 514/621; 514/622
(58) Field of Search ................ 564/180, 237; 514/619, 617, 618, 620, 621, 622

(56) References Cited

U.S. PATENT DOCUMENTS 5,733,934 A    3/1998   Ramakrishna et al. ...... 514/634

FOREIGN PATENT DOCUMENTS

JP   WO 99/55690    11/1999
WO      98/55475    12/1998

OTHER PUBLICATIONS

International Search Report.
Bedair, A.H., et al, "Biologically Active Sulphonamides Derived from α–Pyrones", Indian Journal of Chemistry, vol. 26B, Jan. 1987, pp. 91–94.

Primary Examiner—Richard L. Raymond
Assistant Examiner—H Kahsay Habte
(74) Attorney, Agent, or Firm—Sughrue Mion, PLLC

(57) ABSTRACT

A compound represented by the general formula (1):

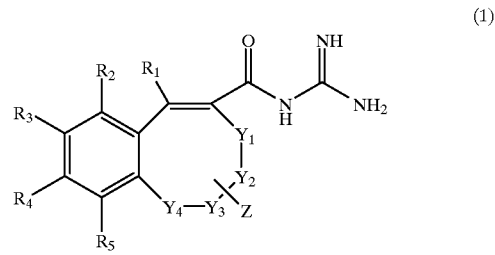

(1)

wherein each of $R_1$, $R_2$, $R_3$, $R_4$ and $R_5$ is a hydrogen atom, an alkyl group, a substituted alkyl group, an alkenyl group, an alkynyl group, a cycloalkyl group, a cycloalkenyl group, a saturated heterocyclic group, an aromatic group, an acyl group or the like; each of $Y_1$, $Y_2$, $Y_3$ and $Y_4$ is a single bond, —$CH_2$—, —O—, —CO— or the like, provided that at least two of $Y_1$ through $Y_4$ are independently a group other than a single bond; and Z may be absent, or one or more Zs may be present and are independently an alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group or the like, is useful as a therapeutic or prophylactic agent for diseases caused by the acceleration of the sodium/proton exchange transport system.

18 Claims, No Drawings

SUBSTITUTED GUANIDINE DERIVATIVES AND PROCESS FOR PRODUCING THE SAME

TECHNICAL FIELD

The present invention relates to novel substituted guanidine derivatives, prodrugs thereof or pharmaceutically acceptable salts of the derivatives or prodrugs, and a process for production of the derivatives, prodrugs or salts. The compounds of the present invention inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion [e.g. cardiac ischemic reperfusion-injury, acute renal failure, or disorders induced by surgical treatment such as organ transplantation or percutaneous transluminal coronary angioplasty (PTCA)], cerebro-ischemic injury [e.g. injury associated with cerebral infarction, injury caused as sequelae of stroke, or brain edema], diseases caused by hyperplasia such as hyperplasia of fibroblast, hyperplasia of smooth muscle cells or hyperplasia of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or restenosis after PTCA, or diseases caused by endotherial cell injury.

BACKGROUND ART

As substituted guanidine derivatives having inhibitory effect on the sodium/proton ($Na^+/H^+$) exchange transport system, there are known, for example, pyrazinoylguanidine derivatives represented by amiloride (for instance, J. Membrane Biol., Vol. 105, 1(1988); Circulation, Vol. 79, 1257 (1989)). It has been reported that benzoylguanidine derivatives inhibit the sodium/proton ($Na^+/H^+$) exchange transport system and hence have antiarrhythmic effect (for instance, J. Mol. Cell. Cardiol., Vol. 24, Suppl. I, S.92(1992); J. Mol. Cell. Cardiol., Vol. 24, Suppl. I, S.117(1992); Japanese Patent Unexamined Publication Nos. 5-339228, 6-9545, 6-345715 and 7-109251). It has also been reported that polycyclic aroylguanidine derivatives inhibit the sodium/proton ($Na^+/H^+$) exchange transport system (for instance, Japanese Patent Unexamined Publication Nos. 7-10839, 7-145149, 7-206823, 8-41028, 8-225513, 8-277269, 9-77753 and 9-291076). In addition, it has been reported that indenoylguanidine derivatives inhibit the sodium/proton ($Na^+/H^+$) exchange transport system (for instance, Japanese Patent Unexamined Publication Nos. 8-291131 and 9-268172). Furthermore, it has been reported that acryloylguanidine derivatives inhibit the sodium/proton ($Na^+/H^+$) exchange transport system (for instance, Japanese Patent Unexamined Publication Nos. 8-319266, 9-52823, 9-59245, 9-67332, 9-67340 and 9-249660).

DISCLOSURE OF THE INVENTION

The present invention is intended to provide novel substituted guanidine derivatives, prodrugs thereof or pharmaceutically acceptable salts of the derivatives or prodrugs, which inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion [e.g. heart muscle ischemic reperfusion-associated disorders, acute renal failure, or disorders induced by surgical treatment such as organ transplantation or percutaneous transluminal coronary angioplasty (PTCA)], cerebro-ischemic disorders [e.g. disorders associated with cerebral infarction, disorders caused after cerebral apoplexy as sequelae, or cerebral edema], diseases caused by excessive cell proliferation such as proliferation of fibroblast, proliferation of smooth muscle cells or proliferation of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or recurrent stricture after PTCA, or diseases caused by endotherial cell injury; and a process for production of said derivatives, prodrugs thereof, or salts of the derivatives or prodrugs.

The present invention includes the aspects described in the following items [1] to [23].

[1]

A compound represented by the general formula (1):

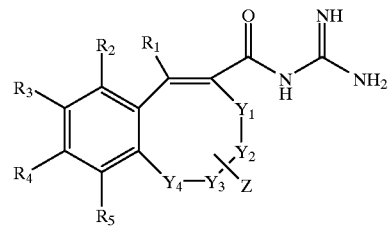

wherein $R_1$ is a hydrogen atom, an alkyl group, a substituted alkyl group, an alkenyl group, an alkynyl group, a cycloalkyl group, a cycloalkenyl group, a saturated heterocyclic group, an aromatic group, an acyl group, a halogen atom, —$OR_6$, —$S(O)_nR_7$, —Q—Ra or

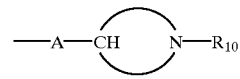

wherein A is an oxygen atom or —$S(O)_n$—, $R_{10}$ is a hydrogen atom, an alkyl group, a substituted alkyl group, an acyl group, —$S(O)_nR_7$ or —Q—Ra, and the ring is a 3- to 8-membered saturated heterocyclic group composed of a nitrogen atom and carbon atoms;

$R_2$, $R_3$, $R_4$ and $R_5$ are independently a hydrogen atom, an alkyl group, a substituted alkyl group, an alkenyl group, an alkynyl group, a cycloalkyl group, a cycloalkenyl group, a saturated heterocyclic group, an aromatic group, an acyl group, a carboxyl group, an alkoxycarbonyl group, a halogen atom, a nitro group, —$OR_6$, —$N(R_8)R_9$, —$CON(R_8)R_9$, —$SO_2N(R_8)R_9$, —$S(O)_nR_7$, —Q—Ra or

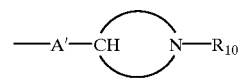

wherein A' is an oxygen atom, —$S(O)_n$— or —$N(R_{51})$—, and $R_{10}$ and the ring are as defined above;

$Y_1$, $Y_2$, $Y_3$ and $Y_4$, which may be the same or different, are independently a single bond, —$CH_2$—, —O—, —CO—, —C(=C($R_{12}$)$R_{13}$)— or —N($R_{11}$)—, provided that at least two of $Y_1$ through $Y_4$ are independently a group other than a single bond;

Z may be absent, or one or more Zs may be present and are, the same or different, independently the following substituent for a hydrogen atom bonded to any of the carbon atoms constituting the ring formed by $Y_1$ through $Y_4$: an alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —$OR_6$, —N($R_8$)$R_9$, —S(O)$_n$$R_7$, —C(O)N($R_8$)$R_9$, —$SO_2$N($R_8$)$R_9$, or —Q—Ra;

Q is a substituted or unsubstituted lower alkylene group;

Ra is a substituted or unsubstituted vinyl group, or a substituted or unsubstituted ethynyl group;

$R_6$ is a hydrogen atom, an alkyl group, a substituted alkyl group, a cycloalkyl group, a cycloalkenyl group, a saturated heterocyclic group or an aromatic group;

$R_7$ is an alkyl group, a substituted alkyl group or an aromatic group;

n is an integer of 0, 1 or 2;

$R_8$ and $R_9$ are independently a hydrogen atom, an alkyl group, a substituted alkyl group, a cycloalkyl group, a cycloalkenyl group, a saturated heterocyclic group, an aromatic group, an acyl group, —S(O)$_2$$R_7$ or —Q—Ra, or $R_8$ and $R_9$, when taken together with the nitrogen atom to which they are bonded, form a 5- to 7-membered saturated cyclic amino group which may contain other heteroatom(s) in the ring and may be substituted by one or more alkyl groups, substituted alkyl groups, hydroxyl groups or —$OR_6$ groups;

$R_{11}$ is a hydrogen atom, an alkyl group, a substituted alkyl group, a cycloalkyl group, a saturated heterocyclic group, an aromatic group, an acyl group, —S(O)$_2$$R_7$ or —Q—Ra;

$R_{51}$ is a hydrogen atom, an alkyl group, a substituted alkyl group, a cycloalkyl group, a saturated heterocyclic group, an aromatic group, an acyl group, —S(O)$_2$$R_7$ or —Q—Ra; and $R_{12}$ and $R_{13}$ are independently a hydrogen atom, an alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —$OR_6$, —CON($R_8$)$R_9$, —S(O)$_n$$R_7$ or —Q—Ra, a prodrug of said compound, or a pharmaceutically acceptable salt of said compound or prodrug.

[2]

A compound, a prodrug thereof or a pharmaceutically acceptable salt of the compound or prodrug according to [1], wherein $Y_1$, $Y_2$, $Y_3$ and $Y_4$, which may be the same or different, are independently a single bond, —$CH_2$—, —CO—, —C(=C($R_{12}$)$R_{13}$)— or —N($R_{11}$)—.

[3]

A compound, a prodrug thereof or a pharmaceutically acceptable salt of the compound or prodrug according to [1], wherein one or two of $Y_1$ through $Y_4$ is a single bond, and the others are independently a group other than a single bond.

[4]

A compound, a prodrug thereof or a pharmaceutically acceptable salt of the compound or prodrug according to [2], wherein one or two of $Y_1$ through $Y_4$ is a single bond, and the others are independently a group other than a single bond.

[5]

A compound, a prodrug thereof or a pharmaceutically acceptable salt of the compound or prodrug according to [1], wherein one of $Y_1$ through $Y_4$ is a single bond, and the others are independently a group other than a single bond.

[6]

A compound, a prodrug thereof or a pharmaceutically acceptable salt of the compound or prodrug according to [2], wherein one of $Y_1$ through $Y_4$ is a single bond, and the others are independently a group other than a single bond.

[7]

A compound, a prodrug thereof or a pharmaceutically acceptable salt of the compound or prodrug according to [5], wherein Z is an alkyl group or a substituted alkyl group.

[8]

A compound, a prodrug thereof or a pharmaceutically acceptable salt of the compound or prodrug according to [5] or [7], wherein each of $Y_1$, $Y_2$ and $Y_3$ is —$CH_2$— which may be substituted by one Z or two or more Zs which may be the same or different, and $Y_4$ is a single bond.

[9]

A compound, a prodrug thereof or a pharmaceutically acceptable salt of the compound or prodrug according to [8], wherein one of $Y_1$, $Y_2$ and $Y_3$ is —$CH_2$— substituted by one Z or two Zs which may be the same or different, and the two others are independently unsubstituted —$CH_2$—, and $Y_4$ is a single bond.

[10]

A compound, a prodrug thereof or a pharmaceutically acceptable salt of the compound or prodrug according to [8], wherein $Y_1$ is —$CH_2$— substituted by one Z or two Zs which may be the same or different, $Y_2$ and $Y_3$ are independently unsubstituted —$CH_2$—, and $Y_4$ is a single bond.

[11]

A compound, a prodrug thereof or a pharmaceutically acceptable salt of the compound or prodrug according to [8], wherein $Y_3$ is —$CH_2$— substituted by one Z or two Zs which may be the same or different, $Y_1$ and $Y_2$ are independently unsubstituted —$CH_2$—, and $Y_4$ is a single bond.

[12]

A compound, a prodrug thereof or a pharmaceutically acceptable salt of the compound or prodrug according to any one of [1] to [11], wherein one of $R_2$, $R_3$, $R_4$ and $R_5$ is a substituted alkyl group, an alkenyl group, an alkynyl group, a cycloalkyl group, a cycloalkenyl group, an acyl group, a carboxyl group, an alkoxycarbonyl group, —CON($R_8$)$R_9$, —$SO_2$N($R_8$)$R_9$, —S(O)$_n$$R_7$, —Q—Ra or

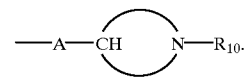

[13]

A compound, a prodrug thereof or a pharmaceutically acceptable salt of the compound or prodrug according to any one of [1] to [12], wherein at least one Z is present.

[14]

A compound, a prodrug thereof or a pharmaceutically acceptable salt of the compound or prodrug according to any one of [1] to [12], wherein at least one of $Y_1$ through $Y_4$ is —N($R_{11}$)— in which $R_{11}$ is an alkyl group, a substituted alkyl group, a cycloalkyl group, a saturated heterocyclic group, an aromatic group, an acyl group, —S(O)$_2$$R_7$ or —Q—Ra.

[15]
N-(aminoiminomethyl)-7-methyl-6,7-dihydro-5H-benzocycloheptene-8-carboxamide or
N-(aminoiminomethyl)-7,7-dimethyl-6,7-dihydro-5H-benzocycloheptene-8-carboxamide, a prodrug thereof, or a pharmaceutically acceptable salt of any one of these compounds or prodrugs.

[16]
A process for producing a compound of the formula (1), a prodrug thereof or a pharmaceutically acceptable salt of the compound or prodrug according to [1], which comprises reacting a compound represented by the formula (2):

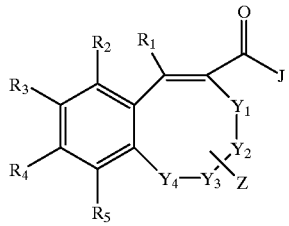

(2)

wherein $R_1$, $R_2$, $R_3$, $R_4$, $R_5$, $Y_1$, $Y_2$, $Y_3$, $Y_4$ and Z are as defined in [1], and J is a hydroxyl group or a leaving group replaceable by a nucleophilic reagent, with guanidine.

[17]
A pharmaceutical composition comprising a compound, a prodrug thereof or a pharmaceutically acceptable salt of the compound or prodrug according to any one of [1] to [15].

[18]
A sodium/proton exchange transport system inhibitor comprising a compound, a prodrug thereof or a pharmaceutically acceptable salt of the compound or prodrug according to any one of [1] to [15].

[19]
A pharmaceutical composition for the treatment or prophylaxis of hypertension, arrhythmia, angina pectoris, cardiac hypertrophy, diabetes mellitus, organ disorders associated with ischemia or ischemic reperfusion, cerebro-ischemic disorders, diseases caused by excessive cell proliferation, or diseases caused by endothelial cell injury, which comprises a compound, a prodrug thereof or a pharmaceutically acceptable salt of the compound or prodrug according to any one of [1] to [15].

[20]
Use of a compound, a prodrug thereof or a pharmaceutically acceptable salt of the compound or prodrug according to any one of [1] to [15] in the manufacture of a sodium/proton exchange transport system inhibitor.

[21]
Use of a compound, a prodrug thereof or a pharmaceutically acceptable salt of the compound or prodrug according to any one of [1] to [15] in the manufacture of a pharmaceutical composition for the treatment or prophylaxis of hypertension, arrhythmia, angina pectoris, cardiac hypertrophy, diabetes mellitus, organ disorders associated with ischemia or ischemic reperfusion, cerebro-ischemic disorders, diseases caused by excessive cell proliferation, or diseases caused by endothelial cell injury.

[22]
A method for inhibiting a sodium/proton exchange transport system which comprises administering a compound, a prodrug thereof or a pharmaceutically acceptable salt of the compound or prodrug according to any one of [1] to [15] to a mammal including a human being, in a pharmacologically effective amount.

[23]
A method for treating or preventing hypertension, arrhythmia, angina pectoris, cardiac hypertrophy, diabetes mellitus, organ disorders associated with ischemia or ischemic reperfusion, cerebro-ischemic disorders, diseases caused by excessive cell proliferation, or diseases caused by endothelial cell injury, which comprises administering a compound, a prodrug thereof or a pharmaceutically acceptable salt of the compound or prodrug according to any one of [1] to [15] to a mammal including a human being, in a pharmacologically effective amount.

BEST MODE FOR CARRYING OUT THE INVENTION

The various groups in the present invention are explained below.

As the alkyl group, there may be exemplified linear or branched alkyl groups of 8 or less carbon atoms, such as methyl, ethyl, propyl, 2-propyl, butyl, 2-butyl, 2-methylpropyl, 1,1-dimethylethyl, pentyl, hexyl, heptyl, octyl, etc.

The cycloalkyl group may be either an unsubstituted one or a substituted one having as the substituent(s) 1 to 4 alkyl groups, substituted alkyl groups, hydroxyl groups or —$OR_6$ groups, and includes, for example, 3- to 8-membered cycloalkyl groups such as cyclopropyl, cyclobutyl, cyclopentyl, cyclohexyl, cycloheptyl, 2-methylcyclopentyl, 3-methylcyclopentyl, 2-methylcyclohexyl, 3-methylcyclohexyl, 4-methylcyclohexyl, 2-hydroxycyclopentyl, 3-hydroxycyclopentyl, 2-hydroxycyclohexyl, 3-hydroxycyclohexyl, 4-hydroxycyclohexyl, 2-(hydroxymethyl)cyclopentyl, 3-(hydroxymethyl)cyclopentyl, 2-(hydroxymethyl)cyclohexyl, 3-(hydroxymethyl)cyclohexyl, 4-(hydroxymethyl)cyclohexyl, 2-(aminomethyl)cyclopentyl, 3-(aminomethyl)cyclopentyl, 2-(aminomethyl)cyclohexyl, 3-(aminomethyl)cyclohexyl, 4-(aminomethyl)cyclohexyl, 2-(methoxymethyl)-cyclopentyl, 3-(methoxymethyl)cyclopentyl, 2-(methoxymethyl)cyclohexyl, 3-(methoxymethyl)cyclohexyl, 4-(methoxymethyl)cyclohexyl, etc.

The cycloalkenyl group may be either an unsubstituted one or a substituted one having as the substituent(s) 1 to 4 alkyl groups, substituted alkyl groups, hydroxyl groups or —$OR_6$ groups, and includes, for example, 3- to 8-membered cycloalkenyl groups having a double bond, such as 1-cyclopentenyl, 2-cyclopentenyl, 3-cyclopentenyl, 1-cyclohexenyl, 2-cyclohexenyl, 3-cyclohexenyl, etc.

The saturated heterocyclic group may be either an unsubstituted one or a substituted one having as the substituent(s) 1 to 4 alkyl groups, substituted alkyl groups, hydroxyl groups or —$OR_6$ groups, and includes, for example, 3- to 8-membered saturated heterocyclic groups having an oxygen atom or a sulfur atom, such as 2-tetrahydrofuranyl, 3-tetrahydrofuranyl, 2-tetrahydro-2H-pyranyl, 4-tetrahydro-4H-pyranyl, etc.

The halogen atom includes, for example, iodine, fluorine, chlorine and bromine atoms.

As the alkoxycarbonyl group, there may be exemplified linear or branched alkoxycarbonyl groups of 6 or less carbon atoms, such as methoxycarbonyl, ethoxycarbonyl, propoxycarbonyl, 2-propoxycarbonyl, etc.

The aromatic group includes substituted or unsubstituted aryl groups and substituted or unsubstituted heteroaryl groups. As the aryl groups, there may be exemplified aryl groups of 10 or less carbon atoms, such as phenyl, naphthyl, etc. As the heteroaryl groups, there may be exemplified 5- or 6-membered heteroaryl groups containing 1 to 4 nitrogen atoms and 5- or 6-membered heteroaryl groups containing 0 to 2 nitrogen atoms and an oxygen atom or a sulfur atom, for example, 2-, 3- or 4-pyridyl, pyrrolyl, isoimidazolyl, triazolyl, tetrazolyl, 2- or 3-furyl, 2- or 3-thienyl, 1-, 3- or 4-oxazolyl, and 3-, 4- or 5-isoxazolyl.

The substituent of each of the substituted aryl group and the substituted heteroaryl group includes alkyl groups, substituted alkyl groups, halogen atoms, nitro group, alkoxycarbonyl groups, carboxyl group, and groups represented by the formula —$OR_6$, —$N(R_8)R_9$, —$CON(R_8)R_9$, —$SO_2N(R_8)R_9$ or —$S(O)_nR_7$.

When $R_1$, $R_2$, $R_3$, $R_4$ or $R_5$ is a group represented by the formula —$OR_6$ wherein $R_6$ is an aromatic group, typical examples of the —$OR_6$ group are phenoxy group and substituted phenoxy groups. Examples of the substituted phenoxy groups are phenoxy groups substituted by, for example, a nitro group; a —$N(R_8)R_9$ group wherein each of $R_8$ and $R_9$ is, for example, a hydrogen atom or an alkyl group; or a substituted alkyl group (the substituent is, for example, a hydroxyl group or a —$N(R_8)R_9$ group). More specific examples of the substituted phenoxy groups are o-, m- or p-nitrophenoxy, o-, m- or p-aminophenoxy, o-, m- or p-(dimethylamino)phenoxy, o-, m- or p-(aminomethyl)phenoxy, o-, m- or p-(dimethylaminomethyl)phenoxy, etc.

As the alkoxy group, there may be exemplified linear or branched alkoxy groups of 6 or less carbon atoms, such as methoxy, ethoxy, isopropoxy, tert-butoxy, etc.

As the heteroatom(s) of the 5- to 7-membered saturated cyclic amino group which $R_8$ and $R_9$ form when taken together with the nitrogen atom to which they are bonded, and which may contain other heteroatom(s) in the ring, there may be exemplified oxygen atom, nitrogen atom and sulfur atom. Specific examples of the 5- to 7-membered cyclic amino group are 5- to 7-membered ring groups containing 1 to 3 nitrogen atoms and 5- to 7-membered ring groups containing a nitrogen atom and an oxygen atom. More specific examples of the 5- to 7-membered cyclic amino group are 1-pyrrolidinyl, 1-piperidino, 1-piperazinyl, morpholino, 1-(4-methyl)piperazinyl, etc.

The substituent of the substituted alkyl group includes halogen atoms, hydroxyl group, alkoxy groups, cycloalkyl groups, cyano group, carboxyl group, alkoxycarbonyl groups, acyl groups, aromatic groups, and groups represented by the formula —CONRpRq wherein Rp and Rq is independently a hydrogen atom or an alkyl group, or Rp and Rq, when taken together, represent a 5- to 7-membered saturated cyclic amino group which may contain another heteroatom; —$N(R_8)R_9$; or

wherein R" is a hydrogen atom, an alkyl group or a substituted alkyl group, and the ring is a 3- to 8-membered saturated heterocyclic group composed of a nitrogen atom and carbon atoms. Particularly when $R_1$, $R_2$, $R_3$, $R_4$, $R_5$, $R_7$, $R_{12}$, $R_{13}$ or Z is a substituted alkyl group, the substituent includes, for example, cycloalkyl groups, halogen atoms, hydroxyl group, alkoxy groups, carboxyl group, alkoxycarbonyl groups, acyl groups, aromatic groups and groups represented by the formula —CONRpRq or —$N(R_8)R_9$. When $R_8$, $R_9$, $R_{10}$ or $R_{11}$ is a substituted alkyl group, the substituent includes, for example, cycloalkyl groups, hydroxyl group, alkoxy groups, carboxyl group, alkoxycarbonyl groups, acyl groups, aryl groups, and groups represented by the formula —CONRpRq or —$N(R_8)R_9$. As the alkyl portion of the substituted alkyl group, there may be exemplified the same groups as those exemplified above as the alkyl group.

Such a substituted alkyl group includes, for example, alkyl groups of 1 to 5 carbon atoms substituted by a cycloalkyl group of 3 to 6 carbon atoms; polyhaloalkyl groups of 1 to 5 carbon atoms; hydroxyalkyl groups of 1 to 6 carbon atoms, alkoxyalkyl groups of 2 to 6 carbon atoms; cyanoalkyl groups of 2 to 6 carbon atoms; carboxyalkyl groups of 2 to 6 carbon atoms; alkoxycarbonylalkyl groups of 3 to 8 carbon atoms; alkanoylalkyl groups of 3 to 8 carbon atoms; aroylalkyl groups of 16 or less carbon atoms; substituted or unsubstituted phenyl- or naphthyl-C1~C5 alkyl groups; carbamoyl-C1~C3 alkyl groups which may have one or two C1~C3 alkyl groups as a substituent(s) on the nitrogen atom; amino-C1~C5 alkyl groups which may have one or two C1~C3 alkyl or C7~C11 aralkyl groups as a substituent(s) on the nitrogen atom; and 5- to 7-membered saturated cyclic amino-C1~C3 alkyl groups.

As the aralkyl group, alkyl groups substituted by an aryl group may be exemplified.

Typical examples of the substituted alkyl group are polyhaloalkyl groups of 1 to 3 carbon atoms, such as trifluoromethyl, trifluoroethyl, trichloromethyl, etc.; hydroxyalkyl groups of 1 to 6 carbon atoms, such as hydroxymethyl, hydroxyethyl, 1-hydroxyethyl, etc.; aminoalkyl groups of 1 to 5 carbon atoms, such as aminomethyl, aminoethyl, 1-aminoethyl, etc.; alkoxyalkyl groups of 1 to 6 carbon atoms, such as methoxyethyl, ethoxyethyl, methoxypropyl, etc.; carboxyalkyl groups of 2 to 6 carbon atoms, such as carboxyethyl, carboxypropyl, etc.; alkoxycarbonylalkyl groups of 3 to 7 carbon atoms, such as methoxycarbonylmethyl, ethoxycarbonylmethyl, methoxycarbonylethyl, etc.; phenyl- or naphthyl-C1~C5 alkyl groups (which may have in the phenyl or naphthyl portion a substituent such as a C1~C3 alkyl group, halogen atom, nitro group, amino group, hydroxyl group, C1~C3 alkoxy group or the like) such as benzyl, phenylethyl, phenylpropyl, phenylbutyl, 1- or 2-naphthylmethyl, etc.; carbamoyl-C1~C3 alkyl groups which may have one or two C1~C3 alkyl groups as a substituent(s) on the nitrogen atom, for example, carbamoylmethyl, carbamoylethyl, dimethylcarbamoylmethyl, etc.; amino-C1~C5 alkyl groups which may have one or two C1~C3 alkyl or C7~C11 aralkyl groups as a substituent(s) on the nitrogen atom, for example, aminoethyl, aminopropyl, dimethylaminoethyl, dimethylaminopropyl, diethylaminoethyl, N-methyl-N-benzylaminoethyl, etc.; and 5- to 7-membered saturated cyclic amino-C1~C3 alkyl groups such as 1-pyrrolidinylethyl, piperidinoethyl, etc. For $R_8$ and $R_9$, phenyl-C1~C5 alkyl groups such as phenylethyl and the like may be exemplified as the substituted alkyl group.

The substituent of each of the lower alkylene group for Q and the vinyl or ethynyl group for Ra includes, for example, alkyl groups, substituted alkyl groups, cycloalkyl groups, cycloalkenyl groups, saturated heterocyclic groups, carboxyl group, alkoxycarbonyl groups, aromatic groups, and groups represented by the formula —$CON(R_8)R_9$.

As the lower alkylene group, there may be exemplified alkylene groups of 6 or less carbon atoms, such as methylene, ethylene, trimethylene, tetramethylene, pentamethylene, hexamethylene, etc.

The acyl group includes, for example, formyl group; alkanoyl groups of 2 to 6 carbon atoms, such as acetyl, propanoyl, etc.; cycloalkanecarbonyl groups of 4 to 7 carbon atoms, such as cyclopropanecarbonyl, cyclobutanecarbonyl, cyclopentanecarbonyl, cyclohexanecarbonyl, etc.; cycloalkenecarbonyl groups of 3 to 6 carbon atoms, such as cyclopentenecarbonyl, cyclohexenecarbonyl, etc.; aroyl groups of 6 to 10 carbon atoms, such as benzoyl, toluoyl, naphthoyl, etc.; saturated heterocyclic ring-carbonyl groups having a 5- or 6-membered saturated heterocyclic ring containing one or two heteroatoms selected from nitrogen atom, oxygen atom and sulfur atom, for example, 2-piperidinecarbonyl, 3-morpholinecarbonyl, etc.; and heteroaromatic acyl groups having a 5- or 6-membered heteroaromatic ring containing one or two heteroatoms selected from nitrogen atom, oxygen atom and sulfur atom, for example, furoyl, thenoyl, nicotinoyl, isonicotinoyl, etc.

As the cyclic amino group which Rp and Rq form when taken together, i.e., the 5- to 7-membered saturated cyclic amino group which may contain other heteroatom(s) in the ring, there may be exemplified the same groups as those exemplified above as the cyclic amino group formed by $R_8$ and $R_9$.

As the group represented by the formula $—S(O)_nR_7$, there may be exemplified alkylsulfonyl groups of 8 or less carbon atoms, such as methylsulfonyl group, ethylsulfonyl group, propylsulfonyl group, isopropylsulfonyl group, etc.; and corresponding alkylsulfinyl groups and alkylthio groups.

As the group represented by the formula:

there may be exemplified groups represented by the following formulas:

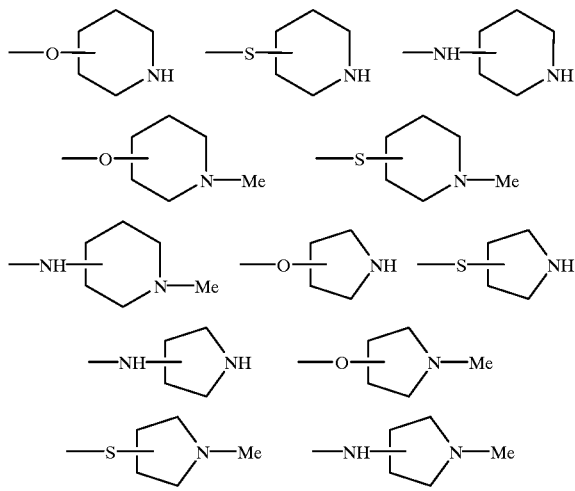

Preferable example thereof are (piperidin-3-yl)oxy, (piperidin-4-yl)oxy, (1-methylpiperidin-3-yl)oxy, (1-methylpiperidin-4-yl)oxy, (pyrrolidin-3-yl)oxy, (1-methylpyrrolidin-3-yl)oxy, (piperidin-3-yl)thio, (piperidin-4-yl)thio, (1-methylpiperidin-3-yl)thio, (1-methylpiperidin-4-yl)thio, (pyrrolidin-3-yl)thio, (1-methylpyrrolidin-2-yl)thio, (piperidin-3-yl)amino, (piperidin-4-yl)amino, (1-methylpiperidin-3-yl)amino, (1-methylpiperidin-4-yl)amino, (pyrrolidin-3-yl)amino, (1-methylpyrrolidin-3-yl)amino, etc.

As the alkenyl group, there may be exemplified alkenyl groups of 6 or less carbon atoms, such as vinyl, allyl, propenyl, 2-propenyl, butenyl, pentenyl, hexenyl, etc.

As the alkynyl group, there may be exemplified alkynyl groups of 6 or less carbon atoms, such as ethynyl, propargyl, butynyl, pentynyl, etc.

As $Y_1$, $Y_2$, $Y_3$ and $Y_4$, the following may be exemplified.

1. $Y_1$ through $Y_4$, which may be the same or different, are independently $—CH_2—$, $—O—$, $—CO—$, $—C(=C(R_{12})R_{13})—$ or $—N(R_{11})—$.

Specific examples of $Y_1$ through $Y_4$ are as follows.

1-1. $Y_1$ is $—CH_2—$, $—CO—$ or $—C(=C(R_{12})R_{13})—$, and $Y_2$ through $Y_4$, which may be the same or different, are independently $—CH_2—$, $—O—$, $—CO—$, $—C(=C(R_{12})R_{13})—$ or $—N(R_{11})—$.

1-2. $Y_1$ is $—CH_2—$, $—CO—$ or $—C(=C(R_{12})R_{13})—$, $Y_2$ and $Y_3$ are independently $—CH_2—$, and $Y_4$ is $—CH_2—$, $—O—$, $—CO—$, $—C(=C(R_{12})R_{13})—$ or $—N(R_{11})—$.

1-3. $Y_1$ is $—CH_2—$, and $Y_2$ through $Y_4$, which may be the same or different, are independently $—CH_2—$, $—O—$, $—CO—$, $—C(=C(R_{12})R_{13})—$ or $—N(R_{11})—$.

1-4. $Y_1$ is $—CH_2—$, one of $Y_2$ through $Y_4$ is $—N(R_{11})—$, and the two others are independently $—CH_2—$.

1-5. All of $Y_1$ through $Y_4$ are independently $—CH_2—$.

2. One of $Y_1$ through $Y_4$ is a single bond, and the three others, which may be the same or different, are independently $—CH_2—$, $—O—$, $—CO—$, $—C(=C(R_{12})R_{13})—$ or $—N(R_{11})—$.

In addition, specific examples of $Y_1$ through $Y_4$ are as follows.

2-1. $Y_1$ is $—CH_2—$, $—CO—$ or $—C(=C(R_{12})R_{13})—$, one of $Y_2$ through $Y_4$ is a single bond, and the two others, which may be the same or different, are independently $—CH_2—$, $—O—$, $—CO—$, $—C(=C(R_{12})R_{13})—$ or $—N(R_{11})—$.

2-2. $Y_1$ is $—CH_2—$, $—CO—$ or $—C(=C(R_{12})R_{13})—$, one of $Y_2$ and $Y_3$ is a single bond while the other is $—CH_2—$, $—O—$, $—CO—$, $—C(=C(R_{12})R_{13})—$ or $—N(R_{11})—$, and $Y_4$ is $—CH_2—$.

2-3. $Y_1$ is $—CH_2—$, $—CO—$ or $—C(=C(R_{12})R_{13})—$, one of $Y_2$ and $Y_3$ is a single bond while the other is $—CH_2—$, and $Y_4$ is $—N(R_{11})—$.

2-4. $Y_1$ is $—CH_2—$, one of $Y_2$ and $Y_3$ is a single bond while the other is $—CH_2—$, $—O—$, $—CO—$, $—C(=C(R_{12})R_{13})—$ or $—N(R_{11})—$, and $Y_4$ is $—CH_2—$.

2-5. $Y_1$ is $—CH_2—$, one of $Y_2$ and $Y_3$ is a single bond while the other is $—CH_2—$, and $Y_4$ is $—N(R_{11})—$.

2-6. $Y_1$ is $—CH_2—$, one of $Y_2$ and $Y_3$ is a single bond while the other is $—N(R_{11})—$, and $Y_4$ is $—CH_2—$.

2-7. One of $Y_1$ through $Y_4$ is a single bond, and the three others are independently $—CH_2—$.

3. Two of $Y_1$ through $Y_4$ are independently a single bond, and the two others, which may be the same or different, are independently $—CH_2—$, $—O—$, $—CO—$, $—C(=C(R_{12})R_{13})—$ or $—N(R_{11})—$.

In addition, specific examples of $Y_1$ through $Y_4$ are as follows.

3-1. $Y_1$ is $—CH_2—$, $—CO—$ or $—C(=C(R_{12})R_{13})—$, $Y_2$ and $Y_3$ are independently a single bond, and $Y_4$ is $—CH_2—$, $—O—$, $—CO—$, $—C(=C(R_{12})R_{13})—$ or $—N(R_{11})—$.

3-2. $Y_1$ is $—CH_2—$, $—CO—$ or $—C(=C(R_{12})R_{13})—$, $Y_2$ and $Y_3$ are independently a single bond, and $Y_4$ is $—CH_2—$.

3-3. $Y_1$ is $—CH_2—$, $—CO—$ or $—C(=C(R_{12})R_{13})—$, $Y_2$ and $Y_3$ are independently a single bond, and $Y_4$ is $—N(R_{11})—$.

3-4. $Y_1$ is $—CH_2—$, $Y_2$ and $Y_3$ are independently a single bond, and $Y_4$ is $—N(R_{11})—$.

3-5. Two of $Y_1$ through $Y_4$ are independently a single bond, and the two others are independently $—CH_2—$.

Furthermore, the present invention relates to a process for producing the compound (1), a prodrug thereof or a pharmaceutically acceptable salt of the compound (1) or prodrug. This process comprises reacting a carboxylic acid reactive derivative of the formula (2):

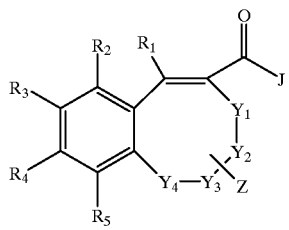

(2)

wherein $R_1$, $R_2$, $R_3$, $R_4$, $R_5$, $Y_1$, $Y_2$, $Y_3$, $Y_4$ and Z are as defined above, and J is a hydroxyl group or a leaving group replaceable by a nucleophilic reagent, with guanidine to form the guanidinocarbonyl group (—C(=O)N=C(NH$_2$)$_2$ group) shown in the formula (1), and if necessary, converting the reaction product to a pharmaceutically acceptable salt.

In the above reaction, when the acid derivative of the formula (2) has a reactive group such as hydroxyl group or amino group, the reactive group is previously protected with a suitable protective group, and the protective group is removed after carrying out the reaction, whereby a desired acylguanidine derivative (1) may be produced.

The leaving group replaceable by a nucleophilic reagent includes, for example, halogen atoms (e.g. fluorine, chlorine and bromine), lower alkoxy groups (e.g. methoxy and ethoxy), aralkyloxy groups (e.g. benzyloxy group), aryloxy groups (e.g. phenoxy group), and groups formed by a condensing agent and a compound of the formula (2) in which J is a hydroxyl group. A process for producing the carboxylic acid reactive derivative of the formula (2) in which J is any of the above-exemplified groups is concretely explained below.

As the carboxylic acid reactive derivative of the formula (2), there may be exemplified acid halides, acid anhydrides (including mixed acid anhydrides) and ester derivatives. Specific examples of the carboxylic acid reactive derivative are acid halides such as acid chlorides and acid bromides; mixed acid anhydrides of an alkyloxycarbonyl chloride type compound (e.g. ethyloxycarbonyl chloride or isobutoxycarbonyl chloride) and an α-polyalkyl-substituted carboxylic acid chloride type compound (2-ethyl-n-butyryl chloride or trimethylacetyl chloride); and ester derivatives such as activated esters (e.g. p-nitrophenyl esters, N-hydroxysuccinimide esters and pentafluorophenyl esters) and common esters (e.g. methyl esters and ethyl esters). Such a carboxylic acid reactive derivative can easily be obtained from a corresponding carboxylic acid according to a conventional method.

When guanidine is reacted with the acid halide or the acid anhydride (including the mixed acid anhydride), the reaction may be carried out in a solvent in the presence of a base or excess guanidine with cooling or at room temperature. As the base, there may be exemplified inorganic bases such as sodium hydroxide, potassium hydroxide, sodium carbonate, potassium carbonate, sodium hydrogencarbonate, etc.; and organic bases such as triethylamine, pyridine, etc. As the solvent, there may be exemplified aromatic hydrocarbon solvents such as benzene, toluene, xylene, etc.; ether solvents such as tetrahydrofuran, 1,4-dioxane, etc.; halogenated hydrocarbon solvents such as dichloromethane, chloroform, 1,2-dichloroethane, etc.; amide solvents such as dimethylformamide, dimethylacetamide, etc.; basic solvents such as pyridine, etc.; and mixed solvents thereof.

When guanidine is reacted with the ester derivative, the reaction is carried out in a solvent in the presence of an equimolar or excess amount of guanidine with heating or cooling. When the ester derivative is an activated ester, the reaction is preferably carried out, for example, in an ether solvent (e.g. tetrahydrofuran, 1,2-dimethoxymethane or dioxane), an ester solvent (e.g. ethyl acetate), dimethylformamide, or a mixed solvent thereof. When the ester derivative is other than activated esters, the reaction is preferably carried out, for example, in an alcohol solvent (e.g. methanol, ethanol or isopropanol), an ether solvent (e.g. tetrahydrofuran, 1,2-dimethoxyethane or dioxane), dimethylformamide, or a mixed solvent thereof. After the solvent is distilled off, the residue may be heated for a short time at about 130° C. if necessary.

The compound (1) of the present invention may be obtained by reacting a carboxylic acid of the general formula (3):

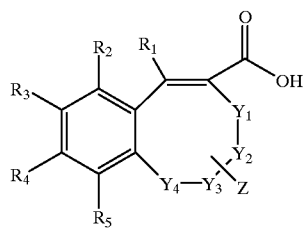

(3)

wherein $R_1$, $R_2$, $R_3$, $R_4$, $R_5$, $Y_1$, $Y_2$, $Y_3$, $Y_4$ and Z are as defined above, with guanidine preferably in the presence of a condensing agent in an inert solvent at room temperature or with heating.

In this reaction, when the compound of the formula (3) has a reactive group such as carboxyl group, hydroxyl group or amino group, the reactive group is previously protected with a suitable protective group, and the protective group is removed after carrying out the reaction, whereby a desired acylguanidine derivative (1) may be produced.

The reaction is preferably carried out in the presence of a condensing agent [e.g. dicyclohexylcarbodiimide (DCC), diisopropylcarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphonylazide (DPPA), or N,N-carbonyldiimidazole (Angew. Chem. Int. Ed. Engl., Vol. 1, 351(1962))] and optionally an additive [e.g. N-hydroxysuccinimide (HONSu), 1-hydroxy-benzotriazole (HOBt) or 3-hydroxy-4-oxo-3,4-dihydro-1,2,3-benzotriazine (HOObt)] in an aromatic hydrocarbon solvent (e.g. benzene, toluene or xylene), an ether solvent (e.g. tetrahydrofuran or 1,4-dioxane), a halogenated hydrocarbon solvent (e.g. dichloromethane, chloroform or 1,2-dichloroethane), an amide solvent (e.g. dimethylformamide or dimethylacetamide), a basic solvent (e.g. pyridine), or a mixed solvent thereof.

In the above-mentioned production, as the protective group for the reactive group such as hydroxyl group, amino group or carboxyl group, protective groups conventionally used in the field of organic synthetic chemistry may be used. The introduction and removal of such a protective group may be carried out by a conventional method (for example, Protective Groups in Organic Synthesis, JOHN WILLEY & SONS, 1991).

The protective group for the hydroxyl group includes, for example, methoxymethyl group and tetrahydropyranyl group. The protective group for the amino group includes, for example, tert-butoxycarbonyl group. Such a protective group for the hydroxyl group may be removed by reaction in a solvent such as aqueous methanol, aqueous ethanol or aqueous tetrahydrofuran in the presence of an acid such as hydrochloric acid, sulfuric acid or acetic acid. The protective group for the amino group may be removed by reaction in a solvent such as aqueous tetrahydrofuran, methylene chloride, chloroform or aqueous methanol in the presence of an acid such as hydrochloric acid or trifluoroacetic acid.

As a form in which the carboxyl group is protected, there may be exemplified tert-butyl esters, orthoesters and acid amides. The protective group used for this protection is removed as follows. In the case of the tert-butyl esters, the removal is carried out, for example, by reaction in an aqueous solvent in the presence of hydrochloric acid. In the case of the orthoesters, the removal is carried out by treatment with an acid and then an alkali such as sodium hydroxide in a solvent such as aqueous methanol, aqueous tetrahydrofuran or aqueous 1,2-dimethoxyethane. In the case of the acid amides, the removal may be carried out by reaction in a solvent such as water, aqueous methanol or aqueous tetrahydrofuran in the presence of an acid such as hydrochloric acid or sulfuric acid.

The compounds of the general formula (2) and the general formula (3), i.e., the starting compounds in the above-mentioned production processes, respectively, are known in literature or may be produced from compounds known in literature according to processes known in literature [for example, Bull. Soc. Chim. Fr., 2(1982), 3–4, 116–124; J. Org. Chem., 48(1983) 26, 5327–5332; J. Chem. Soc., 108 (1986) 7, 1617–1632; J. Chem. Soc., Perkin Trans. 1, 4(1993), 405–410; J. Org. Chem., 53(1988) 20, 4716–4719; J. Am. Chem. Soc., 105(1983) 6, 1586–1590; Synthesis, 2(1985), 169–171; and Synthetic Communications, 18(1998) 4, 343–349]. The carboxylic acid of the general formula (3) can easily be derived from a corresponding ester of the general formula (2) in which J=OR wherein R is a lower alkyl group such as methyl or ethyl, by a conventional hydrolysis reaction. The carboxylic acid reactive derivative of the general formula (2) may be synthesized from the carboxylic acid of the general formula (3) according to a conventional process.

There is given below examples of process for synthesizing each of esters of the general formulas (1d) and (1f) which correspond the general formula (2) in which J=OR wherein R is an alkyl group such as methyl or ethyl.

The esters of the general formulas (1d) and (1f) may be synthesized according to the following reaction formulas:

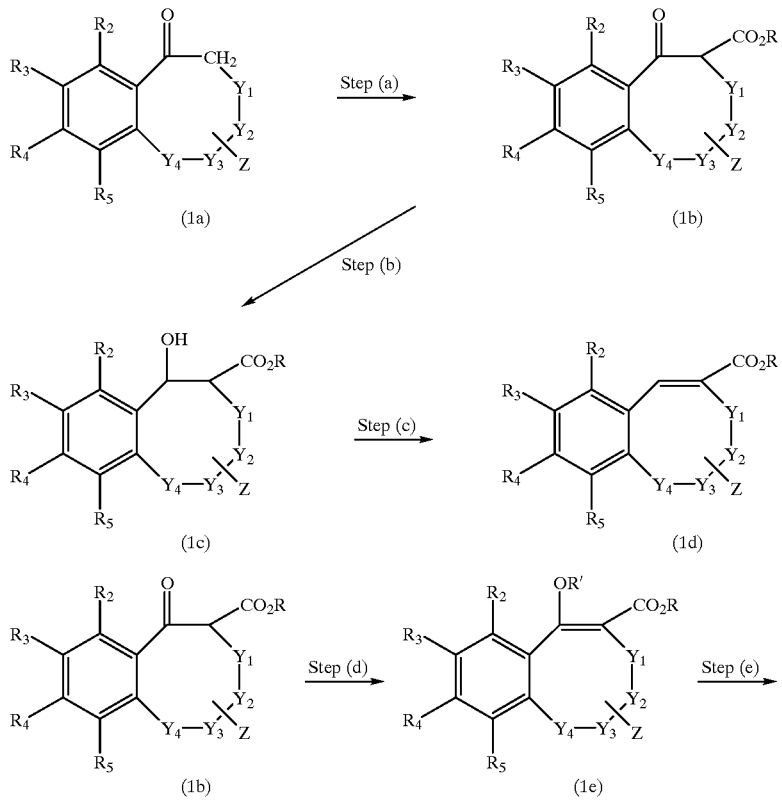

-continued

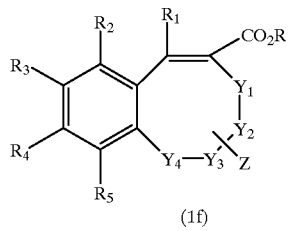

(1f)

wherein $R_1$, $R_2$, $R_3$, $R_4$, $R_5$, $Y_1$, $Y_2$, $Y_3$, $Y_4$ and Z are as defined above, and R and R', which may be the same or different, are independently a lower alkyl group.

The step (a) may be carried out by reacting a compound (1a) with a carbonic acid ester (e.g. diethyl carbonate or dimethyl carbonate), a phosphonoformic acid ester (e.g. ethyl diethylphosphonoformate), an oxalic acid ester (e.g. diethyl oxalate or dimethyl oxalate) or the like usually at 20° C. to 100° C. in the presence of a base (e.g. sodium hydride, sodium ethoxide or sodium methoxide) in an inert solvent (e.g. benzene, toluene, diethyl ether, tetrahydrofuran, dioxane, ethanol or N,N-dimethylformamide).

The reduction of a ketone in the step (b) may be carried out by the use of sodium tetrahydroborate, for example, in an alcohol (e.g. methanol or ethanol) usually at −30° C. to 30° C.

The dehydrating reaction in the step (c) may be carried out, for example, by treating a compound (1c) with a solvent (e.g. water) containing a suitable acid (e.g. sulfuric acid, acetic acid, hydrochloric acid, boric acid, oxalic acid or p-toluenesulfonic acid) usually at 20° C. to 100° C. Alternatively, the following reaction conditions may be employed. That is, the dehydrating reaction may be carried out also by reacting a compound (1c) with a halogenating agent (e.g. thionyl chloride) or a sulfonating agent (e.g. methanesulfonyl chloride or p-toluenesulfonyl chloride) usually at −20° C. to 30° C. either in an inert solvent (e.g. chloroform, methylene chloride, tetrahydrofuran or N,N-dimethylformamide) in the presence of a base (e.g. triethylamine), or in a basic solvent (e.g. pyridine).

The step (d) may be carried out, for example, by reacting a compound (1b) with a diazoalkane (e.g. diazomethane) usually at −20° C. to 30° C. Alternatively, the following reaction conditions may be employed. That is, the step (d) may be carried out also by reacting a compound (1b) with an alkyl halide or a sulfonic ester [e.g. an alkyl p-toluenesulfonate (e.g. methyl p-toluenesulfonate) or a dialkyl sulfate (e.g. dimethyl sulfate)] usually at −20° C. to 30° C. in an inert solvent (e.g. N,N-dimethylformamide or N-methyl-2-pyrrolidinone) in the presence of a base (e.g. potassium hydride, sodium hydride, potassium 1,1,1,3,3,3-hexamethyldisilazide, potassium tert-butoxide or potassium carbonate).

The step (e) can be carried out, for example, by reacting a compound (1e) with a Grignard reagent ($R_1MgX$ wherein X is a halogen atom such as iodine, bromine or chlorine) usually at −30° C. to 30° C. in an inert solvent (e.g. diethyl ether or tetrahydrofuran).

In each of the above-mentioned synthesis processes, when the intermediate compound used in any of the steps has a reactive group such as carboxyl group, hydroxyl group or amino group, the reactive group is previously protected with a suitable protective group, and the protective group is removed if necessary after carrying out the step, whereby a desired compound of the general formula (2) or (3) may be produced.

As the compound of the general formula (1) produced in the manner described above, the following compounds may be exemplified.

TABLE 1

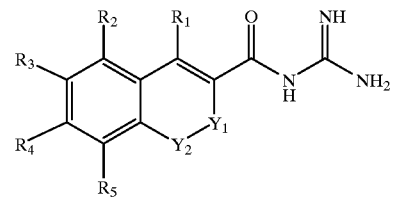

| $R_1$ | $R_2$ | $R_3$ | $R_4$ | $R_5$ | $Y_1$ | $Y_2$ |
|---|---|---|---|---|---|---|
| H | H | H | H | H | —$CH_2$— | —$CH_2$— |
| $CH_3$ | H | H | H | H | —$CH_2$— | —$CH_2$— |
| $C_2H_5$ | H | H | H | H | —$CH_2$— | —$CH_2$— |
| H | H | H | H | $CH_3$ | —$CH_2$— | —$CH_2$— |
| H | H | H | H | Cl | —$CH_2$— | —$CH_2$— |
| H | H | H | H | F | —$CH_2$— | —$CH_2$— |
| H | H | H | H | $OCH_3$ | —$CH_2$— | —$CH_2$— |
| H | H | H | H | $CF_3$ | —$CH_2$— | —$CH_2$— |
| $CH_3$ | H | H | H | $CH_3$ | —$CH_2$— | —$CH_2$— |
| $CH_3$ | H | H | H | Cl | —$CH_2$— | —$CH_2$— |
| $CH_3$ | H | H | H | F | —$CH_2$— | —$CH_2$— |
| $CH_3$ | H | H | H | $OCH_3$ | —$CH_2$— | —$CH_2$— |
| $CH_3$ | H | H | H | $CF_3$ | —$CH_2$— | —$CH_2$— |
| $C_2H_5$ | H | H | H | $CH_3$ | —$CH_2$— | —$CH_2$— |
| $C_2H_5$ | H | H | H | Cl | —$CH_2$— | —$CH_2$— |
| $C_2H_5$ | H | H | H | F | —$CH_2$— | —$CH_2$— |
| $C_2H_5$ | H | H | H | $OCH_3$ | —$CH_2$— | —$CH_2$— |
| $C_2H_5$ | H | H | H | $CF_3$ | —$CH_2$— | —$CH_2$— |
| H | H | H | H | $CH_3$ | —$CH_2$— | —NH— |
| H | H | H | H | Cl | —$CH_2$— | —NH— |
| H | H | H | H | F | —$CH_2$— | —NH— |
| H | H | H | H | $OCH_3$ | —$CH_2$— | —NH— |
| H | H | H | H | $CF_3$ | —$CH_2$— | —NH— |
| $CH_3$ | H | H | H | $CH_3$ | —$CH_2$— | —NH— |
| $CH_3$ | H | H | H | Cl | —$CH_2$— | —NH— |
| $CH_3$ | H | H | H | F | —$CH_2$— | —NH— |
| $CH_3$ | H | H | H | $OCH_3$ | —$CH_2$— | —NH— |
| $CH_3$ | H | H | H | $CF_3$ | —$CH_2$— | —NH— |
| $C_2H_5$ | H | H | H | $CH_3$ | —$CH_2$— | —NH— |
| $C_2H_5$ | H | H | H | Cl | —$CH_2$— | —NH— |
| $C_2H_5$ | H | H | H | F | —$CH_2$— | —NH— |
| $C_2H_5$ | H | H | H | $OCH_3$ | —$CH_2$— | —NH— |
| $C_2H_5$ | H | H | H | $CF_3$ | —$CH_2$— | —NH— |
| H | H | H | H | $CH_3$ | —$CH_2$— | —$N(CH_3)$— |
| H | H | H | H | Cl | —$CH_2$— | —$N(CH_3)$— |
| H | H | H | H | F | —$CH_2$— | —$N(CH_3)$— |
| H | H | H | H | $OCH_3$ | —$CH_2$— | —$N(CH_3)$— |
| H | H | H | H | $CF_3$ | —$CH_2$— | —$N(CH_3)$— |
| $CH_3$ | H | H | H | $CH_3$ | —$CH_2$— | —$N(CH_3)$— |
| $CH_3$ | H | H | H | Cl | —$CH_2$— | —$N(CH_3)$— |
| $CH_3$ | H | H | H | F | —$CH_2$— | —$N(CH_3)$— |
| $CH_3$ | H | H | H | $OCH_3$ | —$CH_2$— | —$N(CH_3)$— |
| $CH_3$ | H | H | H | $CF_3$ | —$CH_2$— | —$N(CH_3)$— |
| $C_2H_5$ | H | H | H | $CH_3$ | —$CH_2$— | —$N(CH_3)$— |
| $C_2H_5$ | H | H | H | Cl | —$CH_2$— | —$N(CH_3)$— |
| $C_2H_5$ | H | H | H | F | —$CH_2$— | —$N(CH_3)$— |
| $C_2H_5$ | H | H | H | $OCH_3$ | —$CH_2$— | —$N(CH_3)$— |

TABLE 1-continued

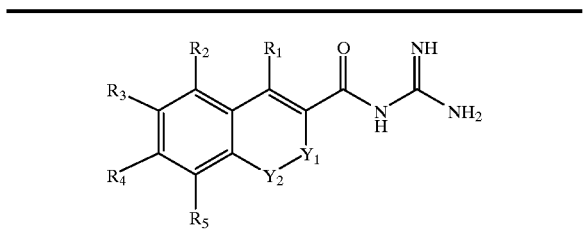

| $R_1$ | $R_2$ | $R_3$ | $R_4$ | $R_5$ | $Y_1$ | $Y_2$ |
|---|---|---|---|---|---|---|
| $C_2H_5$ | H | H | H | $CF_3$ | —$CH_2$— | —$N(CH_3)$— |

TABLE 2

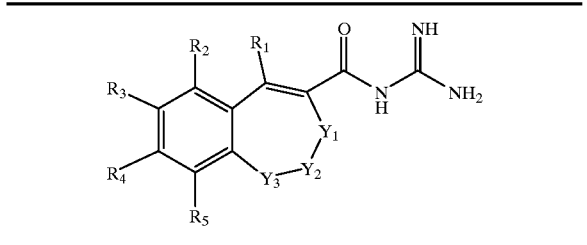

| $R_1$ | $R_2$ | $R_3$ | $R_4$ | $R_5$ | $Y_1$ | $Y_2$ | $Y_3$ |
|---|---|---|---|---|---|---|---|
| H | H | H | H | H | —$CH_2$— | —$CH_2$— | —$CH_2$— |
| $CH_3$ | H | H | H | H | —$CH_2$— | —$CH_2$— | —$CH_2$— |
| $C_2H_5$ | H | H | H | H | —$CH_2$— | —$CH_2$— | —$CH_2$— |
| H | H | H | H | $CH_3$ | —$CH_2$— | —$CH_2$— | —$CH_2$— |
| H | H | H | H | Cl | —$CH_2$— | —$CH_2$— | —$CH_2$— |
| H | H | H | H | F | —$CH_2$— | —$CH_2$— | —$CH_2$— |
| H | H | H | H | $OCH_3$ | —$CH_2$— | —$CH_2$— | —$CH_2$— |
| H | H | H | H | $CF_3$ | —$CH_2$— | —$CH_2$— | —$CH_2$— |
| $CH_3$ | H | H | H | $CH_3$ | —$CH_2$— | —$CH_2$— | —$CH_2$— |
| $CH_3$ | H | H | H | Cl | —$CH_2$— | —$CH_2$— | —$CH_2$— |
| $CH_3$ | H | H | H | F | —$CH_2$— | —$CH_2$— | —$CH_2$— |
| $CH_3$ | H | H | H | $OCH_3$ | —$CH_2$— | —$CH_2$— | —$CH_2$— |
| $CH_3$ | H | H | H | $CF_3$ | —$CH_2$— | —$CH_2$— | —$CH_2$— |
| $C_2H_5$ | H | H | H | $CH_3$ | —$CH_2$— | —$CH_2$— | —$CH_2$— |
| $C_2H_5$ | H | H | H | Cl | —$CH_2$— | —$CH_2$— | —$CH_2$— |
| $C_2H_5$ | H | H | H | F | —$CH_2$— | —$CH_2$— | —$CH_2$— |
| $C_2H_5$ | H | H | H | $OCH_3$ | —$CH_2$— | —$CH_2$— | —$CH_2$— |
| $C_2H_5$ | H | H | H | $CF_3$ | —$CH_2$— | —$CH_2$— | —$CH_2$— |
| H | H | H | H | $CH_3$ | —$CH_2$— | —$CH_2$— | —NH— |
| H | H | H | H | Cl | —$CH_2$— | —$CH_2$— | —NH— |
| H | H | H | H | F | —$CH_2$— | —$CH_2$— | —NH— |
| H | H | H | H | $OCH_3$ | —$CH_2$— | —$CH_2$— | —NH— |
| H | H | H | H | $CF_3$ | —$CH_2$— | —$CH_2$— | —NH— |
| $CH_3$ | H | H | H | $CH_3$ | —$CH_2$— | —$CH_2$— | —NH— |
| $CH_3$ | H | H | H | Cl | —$CH_2$— | —$CH_2$— | —NH— |
| $CH_3$ | H | H | H | F | —$CH_2$— | —$CH_2$— | —NH— |
| $CH_3$ | H | H | H | $OCH_3$ | —$CH_2$— | —$CH_2$— | —NH— |
| $CH_3$ | H | H | H | $CF_3$ | —$CH_2$— | —$CH_2$— | —NH— |
| $C_2H_5$ | H | H | H | $CH_3$ | —$CH_2$— | —$CH_2$— | —NH— |
| $C_2H_5$ | H | H | H | Cl | —$CH_2$— | —$CH_2$— | —NH— |
| $C_2H_5$ | H | H | H | F | —$CH_2$— | —$CH_2$— | —NH— |
| $C_2H_5$ | H | H | H | $OCH_3$ | —$CH_2$— | —$CH_2$— | —NH— |
| $C_2H_5$ | H | H | H | $CF_3$ | —$CH_2$— | —$CH_2$— | —NH— |
| H | H | H | H | $CH_3$ | —$CH_2$— | —$CH_2$— | —$N(CH_3)$— |
| H | H | H | H | Cl | —$CH_2$— | —$CH_2$— | —$N(CH_3)$— |
| H | H | H | H | F | —$CH_2$— | —$CH_2$— | —$N(CH_3)$— |
| H | H | H | H | $OCH_3$ | —$CH_2$— | —$CH_2$— | —$N(CH_3)$— |
| H | H | H | H | $CF_3$ | —$CH_2$— | —$CH_2$— | —$N(CH_3)$— |

TABLE 3

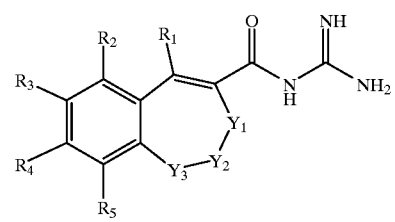

| $R_1$ | $R_2$ | $R_3$ | $R_4$ | $R_5$ | $Y_1$ | $Y_2$ | $Y_3$ |
|---|---|---|---|---|---|---|---|
| $CH_3$ | H | H | H | $CH_3$ | —$CH_2$— | —$CH_2$— | —$N(CH_3)$— |
| $CH_3$ | H | H | H | Cl | —$CH_2$— | —$CH_2$— | —$N(CH_3)$— |
| $CH_3$ | H | H | H | F | —$CH_2$— | —$CH_2$— | —$N(CH_3)$— |
| $CH_3$ | H | H | H | $OCH_3$ | —$CH_2$— | —$CH_2$— | —$N(CH_3)$— |
| $CH_3$ | H | H | H | $CF_3$ | —$CH_2$— | —$CH_2$— | —$N(CH_3)$— |
| $C_2H_5$ | H | H | H | $CH_3$ | —$CH_2$— | —$CH_2$— | —$N(CH_3)$— |
| $C_2H_5$ | H | H | H | Cl | —$CH_2$— | —$CH_2$— | —$N(CH_3)$— |
| $C_2H_5$ | H | H | H | F | —$CH_2$— | —$CH_2$— | —$N(CH_3)$— |
| $C_2H_5$ | H | H | H | $OCH_3$ | —$CH_2$— | —$CH_2$— | —$N(CH_3)$— |
| $C_2H_5$ | H | H | H | $CF_3$ | —$CH_2$— | —$CH_2$— | —$N(CH_3)$— |
| H | H | H | H | $CH_3$ | —$CH_2$— | —NH— | —$CH_2$— |
| H | H | H | H | Cl | —$CH_2$— | —NH— | —$CH_2$— |
| H | H | H | H | F | —$CH_2$— | —NH— | —$CH_2$— |
| H | H | H | H | $OCH_3$ | —$CH_2$— | —NH— | —$CH_2$— |
| H | H | H | H | $CF_3$ | —$CH_2$— | —NH— | —$CH_2$— |
| $CH_3$ | H | H | H | $CH_3$ | —$CH_2$— | —NH— | —$CH_2$— |
| $CH_3$ | H | H | H | Cl | —$CH_2$— | —NH— | —$CH_2$— |
| $CH_3$ | H | H | H | F | —$CH_2$— | —NH— | —$CH_2$— |
| $CH_3$ | H | H | H | $OCH_3$ | —$CH_2$— | —NH— | —$CH_2$— |
| $CH_3$ | H | H | H | $CF_3$ | —$CH_2$— | —NH— | —$CH_2$— |
| $C_2H_5$ | H | H | H | $CH_3$ | —$CH_2$— | —NH— | —$CH_2$— |
| $C_2H_5$ | H | H | H | Cl | —$CH_2$— | —NH— | —$CH_2$— |
| $C_2H_5$ | H | H | H | F | —$CH_2$— | —NH— | —$CH_2$— |
| $C_2H_5$ | H | H | H | $OCH_3$ | —$CH_2$— | —NH— | —$CH_2$— |
| $C_2H_5$ | H | H | H | $CF_3$ | —$CH_2$— | —NH— | —$CH_2$— |
| H | H | H | H | $CH_3$ | —$CH_2$— | —$N(CH_3)$— | —$CH_2$— |
| H | H | H | H | Cl | —$CH_2$— | —$N(CH_3)$— | —$CH_2$— |
| H | H | H | H | F | —$CH_2$— | —$N(CH_3)$— | —$CH_2$— |
| H | H | H | H | $OCH_3$ | —$CH_2$— | —$N(CH_3)$— | —$CH_2$— |
| H | H | H | H | $CF_3$ | —$CH_2$— | —$N(CH_3)$— | —$CH_2$— |
| $CH_3$ | H | H | H | $CH_3$ | —$CH_2$— | —$N(CH_3)$— | —$CH_2$— |
| $CH_3$ | H | H | H | Cl | —$CH_2$— | —$N(CH_3)$— | —$CH_2$— |
| $CH_3$ | H | H | H | F | —$CH_2$— | —$N(CH_3)$— | —$CH_2$— |
| $CH_3$ | H | H | H | $OCH_3$ | —$CH_2$— | —$N(CH_3)$— | —$CH_2$— |
| $CH_3$ | H | H | H | $CF_3$ | —$CH_2$— | —$N(CH_3)$— | —$CH_2$— |
| $C_2H_5$ | H | H | H | $CH_3$ | —$CH_2$— | —$N(CH_3)$— | —$CH_2$— |
| $C_2H_5$ | H | H | H | Cl | —$CH_2$— | —$N(CH_3)$— | —$CH_2$— |
| $C_2H_5$ | H | H | H | F | —$CH_2$— | —$N(CH_3)$— | —$CH_2$— |
| $C_2H_5$ | H | H | H | $OCH_3$ | —$CH_2$— | —$N(CH_3)$— | —$CH_2$— |
| $C_2H_5$ | H | H | H | $CF_3$ | —$CH_2$— | —$N(CH_3)$— | —$CH_2$— |

TABLE 4

| R₂ | R₃ | R₄ | R₆ | Y₁ | Y₂ | Y₃ |
|---|---|---|---|---|---|---|
| CH₃ | H | H | H | —CH(CH₃)— | —CH₂— | —CH₂— |
| Cl | H | H | H | —CH(CH₃)— | —CH₂— | —CH₂— |
| F | H | H | H | —CH(CH₃)— | —CH₂— | —CH₂— |
| OCH₃ | H | H | H | —CH(CH₃)— | —CH₂— | —CH₂— |
| CF₃ | H | H | H | —CH(CH₃)— | —CH₂— | —CH₂— |
| SCH₃ | H | H | H | —CH(CH₃)— | —CH₂— | —CH₂— |
| SO₂CH₃ | H | H | H | —CH(CH₃)— | —CH₂— | —CH₂— |
| H | CH₃ | H | H | —CH(CH₃)— | —CH₂— | —CH₂— |
| H | Cl | H | H | —CH(CH₃)— | —CH₂— | —CH₂— |
| H | F | H | H | —CH(CH₃)— | —CH₂— | —CH₂— |
| H | OCH₃ | H | H | —CH(CH₃)— | —CH₂— | —CH₂— |
| H | CF₃ | H | H | —CH(CH₃)— | —CH₂— | —CH₂— |
| H | SCH₃ | H | H | —CH(CH₃)— | —CH₂— | —CH₂— |
| H | SO₂CH₃ | H | H | —CH(CH₃)— | —CH₂— | —CH₂— |
| H | H | CH₃ | H | —CH(CH₃)— | —CH₂— | —CH₂— |
| H | H | Cl | H | —CH(CH₃)— | —CH₂— | —CH₂— |
| H | H | F | H | —CH(CH₃)— | —CH₂— | —CH₂— |
| H | H | OCH₃ | H | —CH(CH₃)— | —CH₂— | —CH₂— |
| H | H | CF₃ | H | —CH(CH₃)— | —CH₂— | —CH₂— |
| H | H | SCH₃ | H | —CH(CH₃)— | —CH₂— | —CH₂— |
| H | H | SO₂CH₃ | H | —CH(CH₃)— | —CH₂— | —CH₂— |
| H | H | H | CH₃ | —CH(CH₃)— | —CH₂— | —CH₂— |
| H | H | H | Cl | —CH(CH₃)— | —CH₂— | —CH₂— |
| H | H | H | F | —CH(CH₃)— | —CH₂— | —CH₂— |
| H | H | H | OCH₃ | —CH(CH₃)— | —CH₂— | —CH₂— |
| H | H | H | CF₃ | —CH(CH₃)— | —CH₂— | —CH₂— |
| H | H | H | SCH₃ | —CH(CH₃)— | —CH₂— | —CH₂— |
| H | H | H | SO₂CH₃ | —CH(CH₃)— | —CH₂— | —CH₂— |

TABLE 5

| R₂ | R₃ | R₄ | R₅ | Y₁ | Y₂ | Y₃ |
|---|---|---|---|---|---|---|
| CH₃ | H | H | H | —C(CH₃)₂— | —CH₂— | —CH₂— |
| Cl | H | H | H | —C(CH₃)₂— | —CH₂— | —CH₂— |
| F | H | H | H | —C(CH₃)₂— | —CH₂— | —CH₂— |
| OCH₃ | H | H | H | —C(CH₃)₂— | —CH₂— | —CH₂— |
| CF₃ | H | H | H | —C(CH₃)₂— | —CH₂— | —CH₂— |
| SCH₃ | H | H | H | —C(CH₃)₂— | —CH₂— | —CH₂— |
| SO₂CH₃ | H | H | H | —C(CH₃)₂— | —CH₂— | —CH₂— |
| H | CH₃ | H | H | —C(CH₃)₂— | —CH₂— | —CH₂— |
| H | Cl | H | H | —C(CH₃)₂— | —CH₂— | —CH₂— |
| H | F | H | H | —C(CH₃)₂— | —CH₂— | —CH₂— |
| H | OCH₃ | H | H | —C(CH₃)₂— | —CH₂— | —CH₂— |
| H | CF₃ | H | H | —C(CH₃)₂— | —CH₂— | —CH₂— |
| H | SCH₃ | H | H | —C(CH₃)₂— | —CH₂— | —CH₂— |
| H | SO₂CH₃ | H | H | —C(CH₃)₂— | —CH₂— | —CH₂— |
| H | H | CH₃ | H | —C(CH₃)₂— | —CH₂— | —CH₂— |
| H | H | Cl | H | —C(CH₃)₂— | —CH₂— | —CH₂— |

TABLE 5-continued

| R₂ | R₃ | R₄ | R₅ | Y₁ | Y₂ | Y₃ |
|---|---|---|---|---|---|---|
| H | H | F | H | —C(CH₃)₂— | —CH₂— | —CH₂— |
| H | H | OCH₃ | H | —C(CH₃)₂— | —CH₂— | —CH₂— |
| H | H | CF₃ | H | —C(CH₃)₂— | —CH₂— | —CH₂— |
| H | H | SCH₃ | H | —C(CH₃)₂— | —CH₂— | —CH₂— |
| H | H | SO₂CH₃ | H | —C(CH₃)₂— | —CH₂— | —CH₂— |
| H | H | H | CH₃ | —C(CH₃)₂— | —CH₂— | —CH₂— |
| H | H | H | Cl | —C(CH₃)₂— | —CH₂— | —CH₂— |
| H | H | H | F | —C(CH₃)₂— | —CH₂— | —CH₂— |
| H | H | H | OCH₃ | —C(CH₃)₂— | —CH₂— | —CH₂— |
| H | H | H | CF₃ | —C(CH₃)₂— | —CH₂— | —CH₂— |
| H | H | H | SCH₃ | —C(CH₃)₂— | —CH₂— | —CH₂— |
| H | H | H | SO₂CH₃ | —C(CH₃)₂— | —CH₂— | —CH₂— |

25

TABLE 6

| R₂ | R₃ | R₄ | R₅ | Y₁ | Y₂ | Y₃ |
|---|---|---|---|---|---|---|
| CH₃ | H | H | H | —CH(C₂H₅)— | —CH₂— | —CH₂— |
| Cl | H | H | H | —CH(C₂H₅)— | —CH₂— | —CH₂— |
| F | H | H | H | —CH(C₂H₅)— | —CH₂— | —CH₂— |
| OCH₃ | H | H | H | —CH(C₂H₅)— | —CH₂— | —CH₂— |
| CF₃ | H | H | H | —CH(C₂H₅)— | —CH₂— | —CH₂— |
| SCH₃ | H | H | H | —CH(C₂H₅)— | —CH₂— | —CH₂— |
| SO₂CH₃ | H | H | H | —CH(C₂H₅)— | —CH₂— | —CH₂— |
| H | CH₃ | H | H | —CH(C₂H₅)— | —CH₂— | —CH₂— |
| H | Cl | H | H | —CH(C₂H₅)— | —CH₂— | —CH₂— |
| H | F | H | H | —CH(C₂H₅)— | —CH₂— | —CH₂— |
| H | OCH₃ | H | H | —CH(C₂H₅)— | —CH₂— | —CH₂— |
| H | CF₃ | H | H | —CH(C₂H₅)— | —CH₂— | —CH₂— |
| H | SCH₃ | H | H | —CH(C₂H₅)— | —CH₂— | —CH₂— |
| H | SO₂CH₃ | H | H | —CH(C₂H₅)— | —CH₂— | —CH₂— |
| H | H | CH₃ | H | —CH(C₂H₅)— | —CH₂— | —CH₂— |
| H | H | Cl | H | —CH(C₂H₅)— | —CH₂— | —CH₂— |
| H | H | F | H | —CH(C₂H₅)— | —CH₂— | —CH₂— |
| H | H | OCH₃ | H | —CH(C₂H₅)— | —CH₂— | —CH₂— |
| H | H | CF₃ | H | —CH(C₂H₅)— | —CH₂— | —CH₂— |
| H | H | SCH₃ | H | —CH(C₂H₅)— | —CH₂— | —CH₂— |
| H | H | SO₂CH₃ | H | —CH(C₂H₅)— | —CH₂— | —CH₂— |
| H | H | H | CH₃ | —CH(C₂H₅)— | —CH₂— | —CH₂— |
| H | H | H | Cl | —CH(C₂H₅)— | —CH₂— | —CH₂— |
| H | H | H | F | —CH(C₂H₅)— | —CH₂— | —CH₂— |
| H | H | H | OCH₃ | —CH(C₂H₅)— | —CH₂— | —CH₂— |
| H | H | H | CF₃ | —CH(C₂H₅)— | —CH₂— | —CH₂— |
| H | H | H | SCH₃ | —CH(C₂H₅)— | —CH₂— | —CH₂— |
| H | H | H | SO₂CH₃ | —CH(C₂H₅)— | —CH₂— | —CH₂— |

TABLE 7

| R$_2$ | R$_3$ | R$_4$ | R$_5$ | Y$_1$ | Y$_2$ | Y$_3$ |
|---|---|---|---|---|---|---|
| CH$_3$ | H | H | H | —CH$_2$— | —CH$_2$— | —CH(CH$_3$)— |
| Cl | H | H | H | —CH$_2$— | —CH$_2$— | —CH(CH$_3$)— |
| F | H | H | H | —CH$_2$— | —CH$_2$— | —CH(CH$_3$)— |
| OCH$_3$ | H | H | H | —CH$_2$— | —CH$_2$— | —CH(CH$_3$)— |
| CF$_3$ | H | H | H | —CH$_2$— | —CH$_2$— | —CH(CH$_3$)— |
| SCH$_3$ | H | H | H | —CH$_2$— | —CH$_2$— | —CH(CH$_3$)— |
| SO$_2$CH$_3$ | H | H | H | —CH$_2$— | —CH$_2$— | —CH(CH$_3$)— |
| H | CH$_3$ | H | H | —CH$_2$— | —CH$_2$— | —CH(CH$_3$)— |
| H | Cl | H | H | —CH$_2$— | —CH$_2$— | —CH(CH$_3$)— |
| H | F | H | H | —CH$_2$— | —CH$_2$— | —CH(CH$_3$)— |
| H | OCH$_3$ | H | H | —CH$_2$— | —CH$_2$— | —CH(CH$_3$)— |
| H | CF$_3$ | H | H | —CH$_2$— | —CH$_2$— | —CH(CH$_3$)— |
| H | SCH$_3$ | H | H | —CH$_2$— | —CH$_2$— | —CH(CH$_3$)— |
| H | SO$_2$CH$_3$ | H | H | —CH$_2$— | —CH$_2$— | —CH(CH$_3$)— |
| H | H | CH$_3$ | H | —CH$_2$— | —CH$_2$— | —CH(CH$_3$)— |
| H | H | Cl | H | —CH$_2$— | —CH$_2$— | —CH(CH$_3$)— |
| H | H | F | H | —CH$_2$— | —CH$_2$— | —CH(CH$_3$)— |
| H | H | OCH$_3$ | H | —CH$_2$— | —CH$_2$— | —CH(CH$_3$)— |
| H | H | CF$_3$ | H | —CH$_2$— | —CH$_2$— | —CH(CH$_3$)— |
| H | H | SCH$_3$ | H | —CH$_2$— | —CH$_2$— | —CH(CH$_3$)— |
| H | H | SO$_2$CH$_3$ | H | —CH$_2$— | —CH$_2$— | —CH(CH$_3$)— |
| H | H | H | CH$_3$ | —CH$_2$— | —CH$_2$— | —CH(CH$_3$)— |
| H | H | H | Cl | —CH$_2$— | —CH$_2$— | —CH(CH$_3$)— |
| H | H | H | F | —CH$_2$— | —CH$_2$— | —CH(CH$_3$)— |
| H | H | H | OCH$_3$ | —CH$_2$— | —CH$_2$— | —CH(CH$_3$)— |
| H | H | H | CF$_3$ | —CH$_2$— | —CH$_2$— | —CH(CH$_3$)— |
| H | H | H | SCH$_3$ | —CH$_2$— | —CH$_2$— | —CH(CH$_3$)— |
| H | H | H | SO$_2$CH$_3$ | —CH$_2$— | —CH$_2$— | —CH(CH$_3$)— |

TABLE 8

| R$_2$ | R$_3$ | R$_4$ | R$_5$ | Y$_1$ | Y$_2$ | Y$_3$ |
|---|---|---|---|---|---|---|
| CH$_3$ | H | H | H | —CH(CH$_2$NH$_2$)— | —CH$_2$— | —CH$_2$— |
| Cl | H | H | H | —CH(CH$_2$NH$_2$)— | —CH$_2$— | —CH$_2$— |
| F | H | H | H | —CH(CH$_2$NH$_2$)— | —CH$_2$— | —CH$_2$— |
| OCH$_3$ | H | H | H | —CH(CH$_2$NH$_2$)— | —CH$_2$— | —CH$_2$— |
| CF$_3$ | H | H | H | —CH(CH$_2$NH$_2$)— | —CH$_2$— | —CH$_2$— |
| SCH$_3$ | H | H | H | —CH(CH$_2$NH$_2$)— | —CH$_2$— | —CH$_2$— |
| SO$_2$CH$_3$ | H | H | H | —CH(CH$_2$NH$_2$)— | —CH$_2$— | —CH$_2$— |
| H | CH$_3$ | H | H | —CH(CH$_2$NH$_2$)— | —CH$_2$— | —CH$_2$— |
| H | Cl | H | H | —CH(CH$_2$NH$_2$)— | —CH$_2$— | —CH$_2$— |
| H | F | H | H | —CH(CH$_2$NH$_2$)— | —CH$_2$— | —CH$_2$— |
| H | OCH$_3$ | H | H | —CH(CH$_2$NH$_2$)— | —CH$_2$— | —CH$_2$— |
| H | CF$_3$ | H | H | —CH(CH$_2$NH$_2$)— | —CH$_2$— | —CH$_2$— |
| H | SCH$_3$ | H | H | —CH(CH$_2$NH$_2$)— | —CH$_2$— | —CH$_2$— |
| H | SO$_2$CH$_3$ | H | H | —CH(CH$_2$NH$_2$)— | —CH$_2$— | —CH$_2$— |
| H | H | CH$_3$ | H | —CH(CH$_2$NH$_2$)— | —CH$_2$— | —CH$_2$— |
| H | H | Cl | H | —CH(CH$_2$NH$_2$)— | —CH$_2$— | —CH$_2$— |

TABLE 8-continued

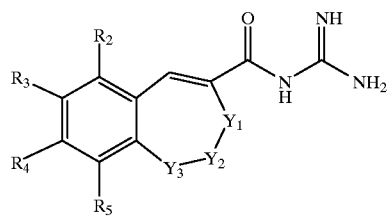

| R₂ | R₃ | R₄ | R₅ | Y₁ | Y₂ | Y₃ |
|---|---|---|---|---|---|---|
| H | H | F | H | —CH(CH₂NH₂)— | —CH₂— | —CH₂— |
| H | H | OCH₃ | H | —CH(CH₂NH₂)— | —CH₂— | —CH₂— |
| H | H | CF₃ | H | —CH(CH₂NH₂)— | —CH₂— | —CH₂— |
| H | H | SCH₃ | H | —CH(CH₂NH₂)— | —CH₂— | —CH₂— |
| H | H | SO₂CH₃ | H | —CH(CH₂NH₂)— | —CH₂— | —CH₂— |
| H | H | H | CH₃ | —CH(CH₂NH₂)— | —CH₂— | —CH₂— |
| H | H | H | Cl | —CH(CH₂NH₂)— | —CH₂— | —CH₂— |
| H | H | H | F | —CH(CH₂NH₂)— | —CH₂— | —CH₂— |
| H | H | H | OCH₃ | —CH(CH₂NH₂)— | —CH₂— | —CH₂— |
| H | H | H | CF₃ | —CH(CH₂NH₂)— | —CH₂— | —CH₂— |
| H | H | H | SCH₃ | —CH(CH₂NH₂)— | —CH₂— | —CH₂— |
| H | H | H | SO₂CH₃ | —CH(CH₂NH₂)— | —CH₂— | —CH₂— |

TABLE 9

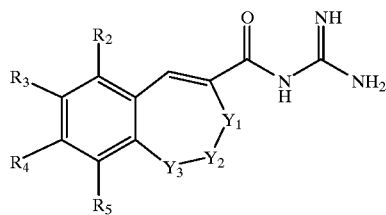

| R₂ | R₃ | R₄ | R₅ | Y₁ | Y₂ | Y₃ |
|---|---|---|---|---|---|---|
| CH₃ | H | H | H | —CH[CH₂N(CH₃)₂]— | —CH₂— | —CH₂— |
| Cl | H | H | H | —CH[CH₂N(CH₃)₂]— | —CH₂— | —CH₂— |
| F | H | H | H | —CH[CH₂N(CH₃)₂]— | —CH₂— | —CH₂— |
| OCH₃ | H | H | H | —CH[CH₂N(CH₃)₂]— | —CH₂— | —CH₂— |
| CF₃ | H | H | H | —CH[CH₂N(CH₃)₃]— | —CH₂— | —CH₂— |
| SCH₃ | H | H | H | —CH[CH₂N(CH₃)₂]— | —CH₂— | —CH₂— |
| SO₂CH₃ | H | H | H | —CH[CH₂N(CH₃)₂]— | —CH₂— | —CH₂— |
| H | CH₃ | H | H | —CH[CH₂N(CH₃)₂]— | —CH₂— | —CH₂— |
| H | Cl | H | H | —CH[CH₂N(CH₃)₂]— | —CH₂— | —CH₂— |
| H | F | H | H | —CH[CH₂N(CH₃)₂]— | —CH₂— | —CH₂— |
| H | OCH₃ | H | H | —CH[CH₂N(CH₃)₂]— | —CH₂— | —CH₂— |
| H | CF₃ | H | H | —CH[CH₂N(CH₃)₂]— | —CH₂— | —CH₂— |
| H | SCH₃ | H | H | —CH[CH₂N(CH₃)₂]— | —CH₂— | —CH₂— |
| H | SO₂CH₃ | H | H | —CH[CH₂N(CH₃)₂]— | —CH₂— | —CH₂— |
| H | H | CH₃ | H | —CH[CH₂N(CH₃)₂]— | —CH₂— | —CH₂— |
| H | H | Cl | H | —CH[CH₂N(CH₃)₂]— | —CH₂— | —CH₂— |
| H | H | F | H | —CH[CH₂N(CH₃)₂]— | —CH₂— | —CH₂— |
| H | H | OCH₃ | H | —CH[CH₂N(CH₃)₂]— | —CH₂— | —CH₂— |
| H | H | CF₃ | H | —CH[CH₂N(CH₃)₂]— | —CH₂— | —CH₂— |
| H | H | SCH₃ | H | —CH[CH₂N(CH₃)₂]— | —CH₂— | —CH₂— |
| H | H | SO₂CH₃ | H | —CH[CH₂N(CH₃)₂]— | —CH₂— | —CH₂— |
| H | H | H | CH₃ | —CH[CH₂N(CH₃)₂]— | —CH₂— | —CH₂— |
| H | H | H | Cl | —CH[CH₂N(CH₃)₂]— | —CH₂— | —CH₂— |
| H | H | H | F | —CH[CH₂N(CH₃)₂]— | —CH₂— | —CH₂— |
| H | H | H | OCH₃ | —CH[CH₂N(CH₃)₂]— | —CH₂— | —CH₂— |
| H | H | H | CF₃ | —CH[CH₂N(CH₃)₂]— | —CH₂— | —CH₂— |
| H | H | H | SCH₃ | —CH[CH₂N(CH₃)₂]— | —CH₂— | —CH₂— |
| H | H | H | SO₂CH₃ | —CH[CH₂N(CH₃)₂]— | —CH₂— | —CH₂— |

TABLE 10

| R₂ | R₃ | R₄ | R₅ | Y₁ | Y₂ | Y₃ |
|---|---|---|---|---|---|---|
| CH₃ | H | H | H | —CH(CH₂OH)— | —CH₂— | —CH₂— |
| Cl | H | H | H | —CH(CH₂OH)— | —CH₂— | —CH₂— |
| F | H | H | H | —CH(CH₂OH)— | —CH₂— | —CH₂— |
| OCH₃ | H | H | H | —CH(CH₂OH)— | —CH₂— | —CH₂— |
| CF₃ | H | H | H | —CH(CH₂OH)— | —CH₂— | —CH₂— |
| SCH₃ | H | H | H | —CH(CH₂OH)— | —CH₂— | —CH₂— |
| SO₂CH₃ | H | H | H | —CH(CH₂OH)— | —CH₂— | —CH₂— |
| H | CH₃ | H | H | —CH(CH₂OH)— | —CH₂— | —CH₂— |
| H | Cl | H | H | —CH(CH₂OH)— | —CH₂— | —CH₂— |
| H | F | H | H | —CH(CH₂OH)— | —CH₂— | —CH₂— |
| H | OCH₃ | H | H | —CH(CH₂OH)— | —CH₂— | —CH₂— |
| H | CF₃ | H | H | —CH(CH₂OH)— | —CH₂— | —CH₂— |
| H | SCH₃ | H | H | —CH(CH₂OH)— | —CH₂— | —CH₂— |
| H | SO₂CH₃ | H | H | —CH(CH₂OH)— | —CH₂— | —CH₂— |
| H | H | CH₃ | H | —CH(CH₂OH)— | —CH₂— | —CH₂— |
| H | H | Cl | H | —CH(CH₂OH)— | —CH₂— | —CH₂— |
| H | H | F | H | —CH(CH₂OH)— | —CH₂— | —CH₂— |
| H | H | OCH₃ | H | —CH(CH₂OH)— | —CH₂— | —CH₂— |
| H | H | CF₃ | H | —CH(CH₂OH)— | —CH₂— | —CH₂— |
| H | H | SCH₃ | H | —CH(CH₂OH)— | —CH₂— | —CH₂— |
| H | H | SO₂CH₃ | H | —CH(CH₂OH)— | —CH₂— | —CH₂— |
| H | H | H | CH₃ | —CH(CH₂OH)— | —CH₂— | —CH₂— |
| H | H | H | Cl | —CH(CH₂OH)— | —CH₂— | —CH₂— |
| H | H | H | F | —CH(CH₂OH)— | —CH₂— | —CH₂— |
| H | H | H | OCH₃ | —CH(CH₂OH)— | —CH₂— | —CH₂— |
| H | H | H | CF₃ | —CH(CH₂OH)— | —CH₂— | —CH₂— |
| H | H | H | SCH₃ | —CH(CH₂OH)— | —CH₂— | —CH₂— |
| H | H | H | SO₂CH₃ | —CH(CH₂OH)— | —CH₂— | —CH₂— |

TABLE 11

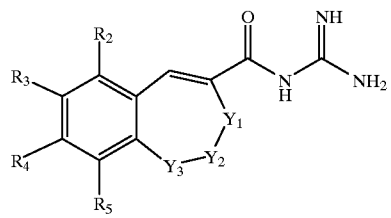

| R₂ | R₃ | R₄ | R₅ | Y₁ | Y₂ | Y₃ |
|---|---|---|---|---|---|---|
| CH₃ | H | H | H | —CH(CH₂OCH₃)— | —CH₂— | —CH₂— |
| Cl | H | H | H | —CH(CH₂OCH₃)— | —CH₂— | —CH₂— |
| F | H | H | H | —CH(CH₂OCH₃)— | —CH₂— | —CH₂— |
| OCH₃ | H | H | H | —CH(CH₂OCH₃)— | —CH₂— | —CH₂— |
| CF₃ | H | H | H | —CH(CH₂OCH₃)— | —CH₂— | —CH₂— |
| SCH₃ | H | H | H | —CH(CH₂OCH₃)— | —CH₂— | —CH₂— |
| SO₂CH₃ | H | H | H | —CH(CH₂OCH₃)— | —CH₂— | —CH₂— |
| H | CH₃ | H | H | —CH(CH₂OCH₃)— | —CH₂— | —CH₂— |
| H | Cl | H | H | —CH(CH₂OCH₃)— | —CH₂— | —CH₂— |
| H | F | H | H | —CH(CH₂OCH₃)— | —CH₂— | —CH₂— |
| H | OCH₃ | H | H | —CH(CH₂OCH₃)— | —CH₂— | —CH₂— |
| H | CF₃ | H | H | —CH(CH₂OCH₃)— | —CH₂— | —CH₂— |
| H | SCH₃ | H | H | —CH(CH₂OCH₃)— | —CH₂— | —CH₂— |
| H | SO₂CH₃ | H | H | —CH(CH₂OCH₃)— | —CH₂— | —CH₂— |
| H | H | CH₃ | H | —CH(CH₂OCH₃)— | —CH₂— | —CH₂— |
| H | H | Cl | H | —CH(CH₂OCH₃)— | —CH₂— | —CH₂— |
| H | H | F | H | —CH(CH₂OCH₃)— | —CH₂— | —CH₂— |
| H | H | OCH₃ | H | —CH(CH₂OCH₃)— | —CH₂— | —CH₂— |
| H | H | CF₃ | H | —CH(CH₂OCH₃)— | —CH₂— | —CH₂— |
| H | H | SCH₃ | H | —CH(CH₂OCH₃)— | —CH₂— | —CH₂— |
| H | H | SO₂CH₃ | H | —CH(CH₂OCH₃)— | —CH₂— | —CH₂— |
| H | H | H | CH₃ | —CH(CH₂OCH₃)— | —CH₂— | —CH₂— |
| H | H | H | Cl | —CH(CH₂OCH₃)— | —CH₂— | —CH₂— |
| H | H | H | F | —CH(CH₂OCH₃)— | —CH₂— | —CH₂— |
| H | H | H | OCH₃ | —CH(CH₂OCH₃)— | —CH₂— | —CH₂— |

TABLE 11-continued

| $R_2$ | $R_3$ | $R_4$ | $R_5$ | $Y_1$ | $Y_2$ | $Y_3$ |
|---|---|---|---|---|---|---|
| H | H | H | $CF_3$ | —CH(CH$_2$OCH$_3$)— | —CH$_2$— | —CH$_2$— |
| H | H | H | $SCH_3$ | —CH(CH$_2$OCH$_3$)— | —CH$_2$— | —CH$_2$— |
| H | H | H | $SO_2CH_3$ | —CH(CH$_2$OCH$_3$)— | —CH$_2$— | —CH$_2$— |

TABLE 12

| $R_2$ | $R_3$ | $R_4$ | $R_5$ | $Y_1$ | $Y_2$ | $Y_3$ |
|---|---|---|---|---|---|---|
| $CH_3$ | H | H | H | —CH(OH)— | —CH$_2$— | —CH$_2$— |
| Cl | H | H | H | —CH(OH)— | —CH$_2$— | —CH$_2$— |
| F | H | H | H | —CH(OH)— | —CH$_2$— | —CH$_2$— |
| $OCH_3$ | H | H | H | —CH(OH)— | —CH$_2$— | —CH$_2$— |
| $CF_3$ | H | H | H | —CH(OH)— | —CH$_2$— | —CH$_2$— |
| $SCH_3$ | H | H | H | —CH(OH)— | —CH$_2$— | —CH$_2$— |
| $SO_2CH_3$ | H | H | H | —CH(OH)— | —CH$_2$— | —CH$_2$— |
| H | $CH_3$ | H | H | —CH(OH)— | —CH$_2$— | —CH$_2$— |
| H | Cl | H | H | —CH(OH)— | —CH$_2$— | —CH$_2$— |
| H | F | H | H | —CH(OH)— | —CH$_2$— | —CH$_2$— |
| H | $OCH_3$ | H | H | —CH(OH)— | —CH$_2$— | —CH$_2$— |
| H | $CF_3$ | H | H | —CH(OH)— | —CH$_2$— | —CH$_2$— |
| H | $SCH_3$ | H | H | —CH(OH)— | —CH$_2$— | —CH$_2$— |
| H | $SO_2CH_3$ | H | H | —CH(OH)— | —CH$_2$— | —CH$_2$— |
| H | H | $CH_3$ | H | —CH(OH)— | —CH$_2$— | —CH$_2$— |
| H | H | Cl | H | —CH(OH)— | —CH$_2$— | —CH$_2$— |
| H | H | F | H | —CH(OH)— | —CH$_2$— | —CH$_2$— |
| H | H | $OCH_3$ | H | —CH(OH)— | —CH$_2$— | —CH$_2$— |
| H | H | $CF_3$ | H | —CH(OH)— | —CH$_2$— | —CH$_2$— |
| H | H | $SCH_3$ | H | —CH(OH)— | —CH$_2$— | —CH$_2$— |
| H | H | $SO_2CH_3$ | H | —CH(OH)— | —CH$_2$— | —CH$_2$— |
| H | H | H | $CH_3$ | —CH(OH)— | —CH$_2$— | —CH$_2$— |
| H | H | H | Cl | —CH(OH)— | —CH$_2$— | —CH$_2$— |
| H | H | H | F | —CH(OH)— | —CH$_2$— | —CH$_2$— |
| H | H | H | $OCH_3$ | —CH(OH)— | —CH$_2$— | —CH$_2$— |
| H | H | H | $CF_3$ | —CH(OH)— | —CH$_2$— | —CH$_2$— |
| H | H | H | $SCH_3$ | —CH(OH)— | —CH$_2$— | —CH$_2$— |
| H | H | H | $SO_2CH_3$ | —CH(OH)— | —CH$_2$— | —CH$_2$— |

TABLE 13

[Structure diagram with R2, R3, R4, R5 substituents on benzene ring fused to Y1-Y2-Y3 ring, with C(=O)-NH-C(=NH)NH2 group]

| R$_2$ | R$_3$ | R$_4$ | R$_5$ | Y$_1$ | Y$_2$ | Y$_3$ |
|---|---|---|---|---|---|---|
| CH$_3$ | H | H | H | —CH(OCH$_3$)— | —CH$_2$— | —CH$_2$— |
| Cl | H | H | H | —CH(OCH$_3$)— | —CH$_2$— | —CH$_2$— |
| F | H | H | H | —CH(OCH$_3$)— | —CH$_2$— | —CH$_2$— |
| OCH$_3$ | H | H | H | —CH(OCH$_3$)— | —CH$_2$— | —CH$_2$— |
| CF$_3$ | H | H | H | —CH(OCH$_3$)— | —CH$_2$— | —CH$_2$— |
| SCH$_3$ | H | H | H | —CH(OCH$_3$)— | —CH$_2$— | —CH$_2$— |
| SO$_2$CH$_3$ | H | H | H | —CH(OCH$_3$)— | —CH$_2$— | —CH$_2$— |
| H | CH$_3$ | H | H | —CH(OCH$_3$)— | —CH$_2$— | —CH$_2$— |
| H | Cl | H | H | —CH(OCH$_3$)— | —CH$_2$— | —CH$_2$— |
| H | F | H | H | —CH(OCH$_3$)— | —CH$_2$— | —CH$_2$— |
| H | OCH$_3$ | H | H | —CH(OCH$_3$)— | —CH$_2$— | —CH$_2$— |
| H | CF$_3$ | H | H | —CH(OCH$_3$)— | —CH$_2$— | —CH$_2$— |
| H | SCH$_3$ | H | H | —CH(OCH$_3$)— | —CH$_2$— | —CH$_2$— |
| H | SO$_2$CH$_3$ | H | H | —CH(OCH$_3$)— | —CH$_2$— | —CH$_2$— |
| H | H | CH$_3$ | H | —CH(OCH$_3$)— | —CH$_2$— | —CH$_2$— |
| H | H | Cl | H | —CH(OCH$_3$)— | —CH$_2$— | —CH$_2$— |
| H | H | F | H | —CH(OCH$_3$)— | —CH$_2$— | —CH$_2$— |
| H | H | OCH$_3$ | H | —CH(OCH$_3$)— | —CH$_2$— | —CH$_2$— |
| H | H | CF$_3$ | H | —CH(OCH$_3$)— | —CH$_2$— | —CH$_2$— |
| H | H | SCH$_3$ | H | —CH(OCH$_3$)— | —CH$_2$— | —CH$_2$— |
| H | H | SO$_2$CH$_3$ | H | —CH(OCH$_3$)— | —CH$_2$— | —CH$_2$— |
| H | H | H | CH$_3$ | —CH(OCH$_3$)— | —CH$_2$— | —CH$_2$— |
| H | H | H | Cl | —CH(OCH$_3$)— | —CH$_2$— | —CH$_2$— |
| H | H | H | F | —CH(OCH$_3$)— | —CH$_2$— | —CH$_2$— |
| H | H | H | OCH$_3$ | —CH(OCH$_3$)— | —CH$_2$— | —CH$_2$— |
| H | H | H | CF$_3$ | —CH(OCH$_3$)— | —CH$_2$— | —CH$_2$— |
| H | H | H | SCH$_3$ | —CH(OCH$_3$)— | —CH$_2$— | —CH$_2$— |
| H | H | H | SO$_2$CH$_3$ | —CH(OCH$_3$)— | —CH$_2$— | —CH$_2$— |

TABLE 14

[Structure diagram with R2, R3, R4, R5 substituents on benzene ring fused to Y1-Y2-Y3 ring, with C(=O)-NH-C(=NH)NH2 group]

| R$_2$ | R$_3$ | R$_4$ | R$_5$ | Y$_1$ | Y$_2$ | Y$_3$ |
|---|---|---|---|---|---|---|
| CH$_3$ | H | H | H | —CH$_2$— | —CH$_2$— | —CH(CH$_2$NH$_2$)— |
| Cl | H | H | H | —CH$_2$— | —CH$_2$— | —CH(CH$_2$NH$_2$)— |
| F | H | H | H | —CH$_2$— | —CH$_2$— | —CH(CH$_2$NH$_2$)— |
| OCH$_3$ | H | H | H | —CH$_2$— | —CH$_2$— | —CH(CH$_2$NH$_2$)— |
| CF$_3$ | H | H | H | —CH$_2$— | —CH$_2$— | —CH(CH$_2$NH$_2$)— |
| SCH$_3$ | H | H | H | —CH$_2$— | —CH$_2$— | —CH(CH$_2$NH$_2$)— |
| SO$_2$CH$_3$ | H | H | H | —CH$_2$— | —CH$_2$— | —CH(CH$_2$NH$_2$)— |
| H | CH$_3$ | H | H | —CH$_2$— | —CH$_2$— | —CH(CH$_2$NH$_2$)— |
| H | Cl | H | H | —CH$_2$— | —CH$_2$— | —CH(CH$_2$NH$_2$)— |
| H | F | H | H | —CH$_2$— | —CH$_2$— | —CH(CH$_2$NH$_2$)— |
| H | OCH$_3$ | H | H | —CH$_2$— | —CH$_2$— | —CH(CH$_2$NH$_2$)— |
| H | CF$_3$ | H | H | —CH$_2$— | —CH$_2$— | —CH(CH$_2$NH$_2$)— |
| H | SCH$_3$ | H | H | —CH$_2$— | —CH$_2$— | —CH(CH$_2$NH$_2$)— |
| H | SO$_2$CH$_3$ | H | H | —CH$_2$— | —CH$_2$— | —CH(CH$_2$NH$_2$)— |

TABLE 14-continued

| R₂ | R₃ | R₄ | R₅ | Y₁ | Y₂ | Y₃ |
|---|---|---|---|---|---|---|
| H | H | CH₃ | H | —CH₂— | —CH₂— | —CH(CH₂NH₂)— |
| H | H | Cl | H | —CH₂— | —CH₂— | —CH(CH₂NH₂)— |
| H | H | F | H | —CH₂— | —CH₂— | —CH(CH₂NH₂)— |
| H | H | OCH₃ | H | —CH₂— | —CH₂— | —CH(CH₂NH₂)— |
| H | H | CF₃ | H | —CH₂— | —CH₂— | —CH(CH₂NH₂)— |
| H | H | SCH₃ | H | —CH₂— | —CH₂— | —CH(CH₂NH₂)— |
| H | H | SO₂CH₃ | H | —CH₂— | —CH₂— | —CH(CH₂NH₂)— |
| H | H | H | CH₃ | —CH₂— | —CH₂— | —CH(CH₂NH₂)— |
| H | H | H | Cl | —CH₂— | —CH₂— | —CH(CH₂NH₂)— |
| H | H | H | F | —CH₂— | —CH₂— | —CH(CH₂NH₂)— |
| H | H | H | OCH₃ | —CH₂— | —CH₂— | —CH(CH₂NH₂)— |
| H | H | H | CF₃ | —CH₂— | —CH₂— | —CH(CH₂NH₂)— |
| H | H | H | SCH₃ | —CH₂— | —CH₂— | —CH(CH₂NH₂)— |
| H | H | H | SO₂CH₃ | —CH₂— | —CH₂— | —CH(CH₂NH₂)— |

TABLE 15

| R₂ | R₃ | R₄ | R₅ | Y₁ | Y₂ | Y₃ |
|---|---|---|---|---|---|---|
| CH₃ | H | H | H | —CH₂— | —CH₂— | —CH[CH₂N(CH₃)₂]— |
| Cl | H | H | H | —CH₂— | —CH₂— | —CH[CH₂N(CH₃)₂]— |
| F | H | H | H | —CH₂— | —CH₂— | —CH[CH₂N(CH₃)₂]— |
| OCH₃ | H | H | H | —CH₂— | —CH₂— | —CH[CH₂N(CH₃)₂]— |
| CF₃ | H | H | H | —CH₂— | —CH₂— | —CH[CH₂N(CH₃)₂]— |
| SCH₃ | H | H | H | —CH₂— | —CH₂— | —CH[CH₂N(CH₃)₂]— |
| SO₂CH₃ | H | H | H | —CH₂— | —CH₂— | —CH[CH₂N(CH₃)₂]— |
| H | CH₃ | H | H | —CH₂— | —CH₂— | —CH[CH₂N(CH₃)₂]— |
| H | Cl | H | H | —CH₂— | —CH₂— | —CH[CH₂N(CH₃)₂]— |
| H | F | H | H | —CH₂— | —CH₂— | —CH[CH₂N(CH₃)₂]— |
| H | OCH₃ | H | H | —CH₂— | —CH₂— | —CH[CH₂N(CH₃)₂]— |
| H | CF₃ | H | H | —CH₂— | —CH₂— | —CH[CH₂N(CH₃)₂]— |
| H | SCH₃ | H | H | —CH₂— | —CH₂— | —CH[CH₂N(CH₃)₂]— |
| H | SO₂CH₃ | H | H | —CH₂— | —CH₂— | —CH[CH₂N(CH₃)₂]— |
| H | H | CH₃ | H | —CH₂— | —CH₂— | —CH[CH₂N(CH₃)₂]— |
| H | H | Cl | H | —CH₂— | —CH₂— | —CH[CH₂N(CH₃)₂]— |
| H | H | F | H | —CH₂— | —CH₂— | —CH[CH₂N(CH₃)₂]— |
| H | H | OCH₃ | H | —CH₂— | —CH₂— | —CH[CH₂N(CH₃)₂]— |
| H | H | CF₃ | H | —CH₂— | —CH₂— | —CH[CH₂N(CH₃)₂]— |
| H | H | SCH₃ | H | —CH₂— | —CH₂— | —CH[CH₂N(CH₃)₂]— |
| H | H | SO₂CH₃ | H | —CH₂— | —CH₂— | —CH[CH₂N(CH₃)₂]— |
| H | H | H | CH₃ | —CH₂— | —CH₂— | —CH[CH₂N(CH₃)₂]— |
| H | H | H | Cl | —CH₂— | —CH₂— | —CH[CH₂N(CH₃)₂]— |
| H | H | H | F | —CH₂— | —CH₂— | —CH[CH₂N(CH₃)₂]— |
| H | H | H | OCH₃ | —CH₂— | —CH₂— | —CH[CH₂N(CH₃)₂]— |
| H | H | H | CF₃ | —CH₂— | —CH₂— | —CH[CH₂N(CH₃)₂]— |
| H | H | H | SCH₃ | —CH₂— | —CH₂— | —CH[CH₂N(CH₃)₂]— |
| H | H | H | SO₂CH₃ | —CH₂— | —CH₂— | —CH[CH₂N(CH₃)₂]— |

TABLE 16

| $R_2$ | $R_3$ | $R_4$ | $R_5$ | $Y_1$ | $Y_2$ | $Y_3$ |
|---|---|---|---|---|---|---|
| $CH_3$ | H | H | H | $-CH_2-$ | $-CH_2-$ | $-CH(CH_2OH)-$ |
| Cl | H | H | H | $-CH_2-$ | $-CH_2-$ | $-CH(CH_2OH)-$ |
| F | H | H | H | $-CH_2-$ | $-CH_2-$ | $-CH(CH_2OH)-$ |
| $OCH_3$ | H | H | H | $-CH_2-$ | $-CH_2-$ | $-CH(CH_2OH)-$ |
| $CF_3$ | H | H | H | $-CH_2-$ | $-CH_2-$ | $-CH(CH_2OH)-$ |
| $SCH_3$ | H | H | H | $-CH_2-$ | $-CH_2-$ | $-CH(CH_2OH)-$ |
| $SO_2CH_3$ | H | H | H | $-CH_2-$ | $-CH_2-$ | $-CH(CH_2OH)-$ |
| H | $CH_3$ | H | H | $-CH_2-$ | $-CH_2-$ | $-CH(CH_2OH)-$ |
| H | Cl | H | H | $-CH_2-$ | $-CH_2-$ | $-CH(CH_2OH)-$ |
| H | F | H | H | $-CH_2-$ | $-CH_2-$ | $-CH(CH_2OH)-$ |
| H | $OCH_3$ | H | H | $-CH_2-$ | $-CH_2-$ | $-CH(CH_2OH)-$ |
| H | $CF_3$ | H | H | $-CH_2-$ | $-CH_2-$ | $-CH(CH_2OH)-$ |
| H | $SCH_3$ | H | H | $-CH_2-$ | $-CH_2-$ | $-CH(CH_2OH)-$ |
| H | $SO_2CH_3$ | H | H | $-CH_2-$ | $-CH_2-$ | $-CH(CH_2OH)-$ |
| H | H | $CH_3$ | H | $-CH_2-$ | $-CH_2-$ | $-CH(CH_2OH)-$ |
| H | H | Cl | H | $-CH_2-$ | $-CH_2-$ | $-CH(CH_2OH)-$ |
| H | H | F | H | $-CH_2-$ | $-CH_2-$ | $-CH(CH_2OH)-$ |
| H | H | $OCH_3$ | H | $-CH_2-$ | $-CH_2-$ | $-CH(CH_2OH)-$ |
| H | H | $CF_3$ | H | $-CH_2-$ | $-CH_2-$ | $-CH(CH_2OH)-$ |
| H | H | $SCH_3$ | H | $-CH_2-$ | $-CH_2-$ | $-CH(CH_2OH)-$ |
| H | H | $SO_2CH_3$ | H | $-CH_2-$ | $-CH_2-$ | $-CH(CH_2OH)-$ |
| H | H | H | $CH_3$ | $-CH_2-$ | $-CH_2-$ | $-CH(CH_2OH)-$ |
| H | H | H | Cl | $-CH_2-$ | $-CH_2-$ | $-CH(CH_2OH)-$ |
| H | H | H | F | $-CH_2-$ | $-CH_2-$ | $-CH(CH_2OH)-$ |
| H | H | H | $OCH_3$ | $-CH_2-$ | $-CH_2-$ | $-CH(CH_2OH)-$ |
| H | H | H | $CF_3$ | $-CH_2-$ | $-CH_2-$ | $-CH(CH_2OH)-$ |
| H | H | H | $SCH_3$ | $-CH_2-$ | $-CH_2-$ | $-CH(CH_2OH)-$ |
| H | H | H | $SO_2CH_3$ | $-CH_2-$ | $-CH_2-$ | $-CH(CH_2OH)-$ |

TABLE 17

| $R_2$ | $R_3$ | $R_4$ | $R_5$ | $Y_1$ | $Y_2$ | $Y_3$ |
|---|---|---|---|---|---|---|
| $CH_3$ | H | H | H | $-CH_2-$ | $-CH_2-$ | $-CH(CH_2OCH_3)-$ |
| Cl | H | H | H | $-CH_2-$ | $-CH_2-$ | $-CH(CH_2OCH_3)-$ |
| F | H | H | H | $-CH_2-$ | $-CH_2-$ | $-CH(CH_2OCH_3)-$ |
| $OCH_3$ | H | H | H | $-CH_2-$ | $-CH_2-$ | $-CH(CH_2OCH_3)-$ |
| $CF_3$ | H | H | H | $-CH_2-$ | $-CH_2-$ | $-CH(CH_2OCH_3)-$ |
| $SCH_3$ | H | H | H | $-CH_2-$ | $-CH_2-$ | $-CH(CH_2OCH_3)-$ |
| $SO_2CH_3$ | H | H | H | $-CH_2-$ | $-CH_2-$ | $-CH(CH_2OCH_3)-$ |
| H | $CH_3$ | H | H | $-CH_2-$ | $-CH_2-$ | $-CH(CH_2OCH_3)-$ |
| H | Cl | H | H | $-CH_2-$ | $-CH_2-$ | $-CH(CH_2OCH_3)-$ |
| H | F | H | H | $-CH_2-$ | $-CH_2-$ | $-CH(CH_2OCH_3)-$ |
| H | $OCH_3$ | H | H | $-CH_2-$ | $-CH_2-$ | $-CH(CH_2OCH_3)-$ |
| H | $CF_3$ | H | H | $-CH_2-$ | $-CH_2-$ | $-CH(CH_2OCH_3)-$ |
| H | $SCH_3$ | H | H | $-CH_2-$ | $-CH_2-$ | $-CH(CH_2OCH_3)-$ |
| H | $SO_2CH_3$ | H | H | $-CH_2-$ | $-CH_2-$ | $-CH(CH_2OCH_3)-$ |

TABLE 17-continued

| R2 | R3 | R4 | R5 | Y1 | Y2 | Y3 |
| --- | --- | --- | --- | --- | --- | --- |
| H | H | CH3 | H | —CH2— | —CH2— | —CH(CH2OCH3)— |
| H | H | Cl | H | —CH2— | —CH2— | —CH(CH2OCH3)— |
| H | H | F | H | —CH2— | —CH2— | —CH(CH2OCH3)— |
| H | H | OCH3 | H | —CH2— | —CH2— | —CH(CH2OCH3)— |
| H | H | CF3 | H | —CH2— | —CH2— | —CH(CH2OCH3)— |
| H | H | SCH3 | H | —CH2— | —CH2— | —CH(CH2OCH3)— |
| H | H | SO2CH3 | H | —CH2— | —CH2— | —CH(CH2OCH3)— |
| H | H | H | CH3 | —CH2— | —CH2— | —CH(CH2OCH3)— |
| H | H | H | Cl | —CH2— | —CH2— | —CH(CH2OCH3)— |
| H | H | H | F | —CH2— | —CH2— | —CH(CH2OCH3)— |
| H | H | H | OCH3 | —CH2— | —CH2— | —CH(CH2OCH3)— |
| H | H | H | CF3 | —CH2— | —CH2— | —CH(CH2OCH3)— |
| H | H | H | SCH3 | —CH2— | —CH2— | —CH(CH2OCH3)— |
| H | H | H | SO2CH3 | —CH2— | —CH2— | —CH(CH2OCH3)— |

TABLE 18

| R2 | R3 | R4 | R5 | Y1 | Y2 | Y3 |
| --- | --- | --- | --- | --- | --- | --- |
| CH3 | H | H | H | —CH2— | —CH2— | —CH(OH)— |
| Cl | H | H | H | —CH2— | —CH2— | —CH(OH)— |
| F | H | H | H | —CH2— | —CH2— | —CH(OH)— |
| OCH3 | H | H | H | —CH2— | —CH2— | —CH(OH)— |
| CF3 | H | H | H | —CH2— | —CH2— | —CH(OH)— |
| SCH3 | H | H | H | —CH2— | —CH2— | —CH(OH)— |
| SO2CH3 | H | H | H | —CH2— | —CH2— | —CH(OH)— |
| H | CH3 | H | H | —CH2— | —CH2— | —CH(OH)— |
| H | Cl | H | H | —CH2— | —CH2— | —CH(OH)— |
| H | F | H | H | —CH2— | —CH2— | —CH(OH)— |
| H | OCH3 | H | H | —CH2— | —CH2— | —CH(OH)— |
| H | CF3 | H | H | —CH2— | —CH2— | —CH(OH)— |
| H | SCH3 | H | H | —CH2— | —CH2— | —CH(OH)— |
| H | SO2CH3 | H | H | —CH2— | —CH2— | —CH(OH)— |
| H | H | CH3 | H | —CH2— | —CH2— | —CH(OH)— |
| H | H | Cl | H | —CH2— | —CH2— | —CH(OH)— |
| H | H | F | H | —CH2— | —CH2— | —CH(OH)— |
| H | H | OCH3 | H | —CH2— | —CH2— | —CH(OH)— |
| H | H | CF3 | H | —CH2— | —CH2— | —CH(OH)— |
| H | H | SCH3 | H | —CH2— | —CH2— | —CH(OH)— |
| H | H | SO2CH3 | H | —CH2— | —CH2— | —CH(OH)— |
| H | H | H | CH3 | —CH2— | —CH2— | —CH(OH)— |
| H | H | H | Cl | —CH2— | —CH2— | —CH(OH)— |
| H | H | H | F | —CH2— | —CH2— | —CH(OH)— |
| H | H | H | OCH3 | —CH2— | —CH2— | —CH(OH)— |
| H | H | H | CF3 | —CH2— | —CH2— | —CH(OH)— |
| H | H | H | SCH3 | —CH2— | —CH2— | —CH(OH)— |
| H | H | H | SO2CH3 | —CH2— | —CH2— | —CH(OH)— |

TABLE 19

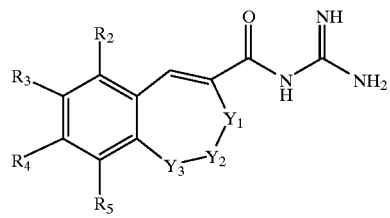

| $R_2$ | $R_3$ | $R_4$ | $R_5$ | $Y_1$ | $Y_2$ | $Y_3$ |
|---|---|---|---|---|---|---|
| $CH_3$ | H | H | H | —$CH_2$— | —$CH_2$— | —$CH(OCH_3)$— |
| Cl | H | H | H | —$CH_2$— | —$CH_2$— | —$CH(OCH_3)$— |
| F | H | H | H | —$CH_2$— | —$CH_2$— | —$CH(OCH_3)$— |
| $OCH_3$ | H | H | H | —$CH_2$— | —$CH_2$— | —$CH(OCH_3)$— |
| $CF_3$ | H | H | H | —$CH_2$— | —$CH_2$— | —$CH(OCH_3)$— |
| $SCH_3$ | H | H | H | —$CH_2$— | —$CH_2$— | —$CH(OCH_3)$— |
| $SO_2CH_3$ | H | H | H | —$CH_2$— | —$CH_2$— | —$CH(OCH_3)$— |
| H | $CH_3$ | H | H | —$CH_2$— | —$CH_2$— | —$CH(OCH_3)$— |
| H | Cl | H | H | —$CH_2$— | —$CH_2$— | —$CH(OCH_3)$— |
| H | F | H | H | —$CH_2$— | —$CH_2$— | —$CH(OCH_3)$— |
| H | $OCH_3$ | H | W | —$CH_2$— | —$CH_2$— | —$CH(OCH_3)$— |
| H | $CF_3$ | H | H | —$CH_2$— | —$CH_2$— | —$CH(OCH_3)$— |
| H | $SCH_3$ | H | H | —$CH_2$— | —$CH_2$— | —$CH(OCH_3)$— |
| H | $SO_2CH_3$ | H | H | —$CH_2$— | —$CH_2$— | —$CH(OCH_3)$— |
| H | H | $CH_3$ | H | —$CH_2$— | —$CH_2$— | —$CH(OCH_3)$— |
| H | H | Cl | H | —$CH_2$— | —$CH_2$— | —$CH(OCH_3)$— |
| H | H | F | H | —$CH_2$— | —$CH_2$— | —$CH(OCH_3)$— |
| H | H | $OCH_3$ | H | —$CH_2$— | —$CH_2$— | —$CH(OCH_3)$— |
| H | H | $CF_3$ | H | —$CH_2$— | —$CH_2$— | —$CH(OCH_3)$— |
| H | H | $SCH_3$ | H | —$CH_2$— | —$CH_2$— | —$CH(OCH_3)$— |
| H | H | $SO_2CH_3$ | H | —$CH_2$— | —$CH_2$— | —$CH(OCH_3)$— |
| H | H | H | $CH_3$ | —$CH_2$— | —$CH_2$— | —$CH(OCH_3)$— |
| H | H | H | Cl | —$CH_2$— | —$CH_2$— | —$CH(OCH_3)$— |
| H | H | H | F | —$CH_2$— | —$CH_2$— | —$CH(OCH_3)$— |
| H | H | H | $OCH_3$ | —$CH_2$— | —$CH_2$— | —$CH(OCH_3)$— |
| H | H | H | $CF_3$ | —$CH_2$— | —$CH_2$— | —$CH(OCH_3)$— |
| H | H | H | $SCH_3$ | —$CH_2$— | —$CH_2$— | —$CH(OCH_3)$— |
| H | H | H | $SO_2CH_3$ | —$CH_2$— | —$CH_2$— | —$CH(OCH_3)$— |

TABLE 20

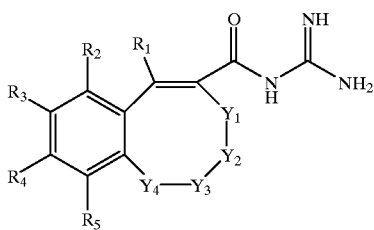

| $R_1$ | $R_2$ | $R_3$ | $R_4$ | $R_5$ | $Y_1$ | $Y_2$ | $Y_3$ | $Y_4$ |
|---|---|---|---|---|---|---|---|---|
| H | H | H | H | H | —$CH_2$— | —$CH_2$— | —$CH_2$— | —$CH_2$— |
| $CH_3$ | H | H | H | H | —$CH_2$— | —$CH_2$— | —$CH_2$— | —$CH_2$— |
| $C_2H_5$ | H | H | H | H | —$CH_2$— | —$CH_2$— | —$CH_2$— | —$CH_2$— |
| H | H | H | H | $CH_3$ | —$CH_2$— | —$CH_2$— | —$CH_2$— | —$CH_2$— |
| H | H | H | H | Cl | —$CH_2$— | —$CH_2$— | —$CH_2$— | —$CH_2$— |
| H | H | H | H | F | —$CH_2$— | —$CH_2$— | —$CH_2$— | —$CH_2$— |
| H | H | H | H | $OCH_3$ | —$CH_2$— | —$CH_2$— | —$CH_2$— | —$CH_2$— |
| H | H | H | H | $CF_3$ | —$CH_2$— | —$CH_2$— | —$CH_2$— | —$CH_2$— |
| $CH_3$ | H | H | H | $CH_3$ | —$CH_2$— | —$CH_2$— | —$CH_2$— | —$CH_2$— |
| $CH_3$ | H | H | H | Cl | —$CH_2$— | —$CH_2$— | —$CH_2$— | —$CH_2$— |
| $CH_3$ | H | H | H | F | —$CH_2$— | —$CH_2$— | —$CH_2$— | —$CH_2$— |
| $CH_3$ | H | H | H | $OCH_3$ | —$CH_2$— | —$CH_2$— | —$CH_2$— | —$CH_2$— |
| $CH_3$ | H | H | H | $CF_3$ | —$CH_2$— | —$CH_2$— | —$CH_2$— | —$CH_2$— |

TABLE 20-continued

| R₁ | R₂ | R₃ | R₄ | R₅ | Y₁ | Y₂ | Y₃ | Y₄ |
|---|---|---|---|---|---|---|---|---|
| C₂H₅ | H | H | H | CH₃ | —CH₂— | —CH₂— | —CH₂— | —CH₂— |
| C₂H₅ | H | H | H | Cl | —CH₂— | —CH₂— | —CH₂— | —CH₂— |
| C₂H₅ | H | H | H | F | —CH₂— | —CH₂— | —CH₂— | —CH₂— |
| C₂H₅ | H | H | H | OCH₃ | —CH₂— | —CH₂— | —CH₂— | —CH₂— |
| C₂H₅ | H | H | H | CF₃ | —CH₂— | —CH₂— | —CH₂— | —CH₂— |
| H | H | H | H | CH₃ | —CH₂— | —CH₂— | —CH₂— | —NH— |
| H | H | H | H | Cl | —CH₂— | —CH₂— | —CH₂— | —NH— |
| H | H | H | H | F | —CH₂— | —CH₂— | —CH₂— | —NH— |
| H | H | H | H | OCH₃ | —CH₂— | —CH₂— | —CH₂— | —NH— |
| H | H | H | H | CF₃ | —CH₂— | —CH₂— | —CH₂— | —NH— |
| CH₃ | H | H | H | CH₃ | —CH₂— | —CH₂— | —CH₂— | —NH— |
| CH₃ | H | H | H | Cl | —CH₂— | —CH₂— | —CH₂— | —NH— |
| CH₃ | H | H | H | F | —CH₂— | —CH₂— | —CH₂— | —NH— |
| CH₃ | H | H | H | OCH₃ | —CH₂— | —CH₂— | —CH₂— | —NH— |
| CH₃ | H | H | H | CF₃ | —CH₂— | —CH₂— | —CH₂— | —NH— |
| C₂H₅ | H | H | H | CH₃ | —CH₂— | —CH₂— | —CH₂— | —NH— |
| C₂H₅ | H | H | H | Cl | —CH₂— | —CH₂— | —CH₂— | —NH— |
| C₂H₅ | H | H | H | F | —CH₂— | —CH₂— | —CH₂— | —NH— |
| C₂H₅ | H | H | H | OCH₃ | —CH₂— | —CH₂— | —CH₂— | —NH— |
| C₂H₅ | H | H | H | CF₃ | —CH₂— | —CH₂— | —CH₂— | —NH— |
| H | H | H | H | CH₃ | —CH₂— | —CH₂— | —CH₂— | —N(CH₃)— |
| H | H | H | H | Cl | —CH₂— | —CH₂— | —CH₂— | —N(CH₃)— |
| H | H | H | H | F | —CH₂— | —CH₂— | —CH₂— | —N(CH₃)— |
| H | H | H | H | OCH₃ | —CH₂— | —CH₂— | —CH₂— | —N(CH₃)— |
| H | H | H | H | CF₃ | —CH₂— | —CH₂— | —CH₂— | —N(CH₃)— |

TABLE 21

| R₁ | R₂ | R₃ | R₄ | R₅ | Y₁ | Y₂ | Y₃ | Y₄ |
|---|---|---|---|---|---|---|---|---|
| CH₃ | H | H | H | CH₃ | —CH₂— | —CH₂— | —CH₂— | —N(CH₃)— |
| CH₃ | H | H | H | Cl | —CH₂— | —CH₂— | —CH₂— | —N(CH₃)— |
| CH₃ | H | H | H | F | —CH₂— | —CH₂— | —CH₂— | —N(CH₃)— |
| CH₃ | H | H | H | OCH₃ | —CH₂— | —CH₂— | —CH₂— | —N(CH₃)— |
| CH₃ | H | H | H | CF₃ | —CH₂— | —CH₂— | —CH₂— | —N(CH₃)— |
| C₂H₅ | H | H | H | CH₃ | —CH₂— | —CH₂— | —CH₂— | —N(CH₃)— |
| C₂H₅ | H | H | H | Cl | —CH₂— | —CH₂— | —CH₂— | —N(CH₃)— |
| C₂H₅ | H | H | H | F | —CH₂— | —CH₂— | —CH₂— | —N(CH₃)— |
| C₂H₅ | H | H | H | OCH₃ | —CH₂— | —CH₂— | —CH₂— | —N(CH₃)— |
| C₂H₅ | H | H | H | CF₃ | —CH₂— | —CH₂— | —CH₂— | —N(CH₃)— |
| H | H | H | H | CH₃ | —CH₂— | —CH₂— | —NH— | —CH₂— |
| H | H | H | H | Cl | —CH₂— | —CH₂— | —NH— | —CH₂— |
| H | H | H | H | F | —CH₂— | —CH₂— | —NH— | —CH₂— |
| H | H | H | H | OCH₃ | —CH₂— | —CH₂— | —NH— | —CH₂— |
| H | H | H | H | CF₃ | —CH₂— | —CH₂— | —NH— | —CH₂— |
| CH₃ | H | H | H | CH₃ | —CH₂— | —CH₂— | —NH— | —CH₂— |
| CH₃ | H | H | H | Cl | —CH₂— | —CH₂— | —NH— | —CH₂— |

TABLE 21-continued

![Structure with R1-R5 on benzene, Y1-Y4 chain, connected to acylguanidine]

| R₁ | R₂ | R₃ | R₄ | R₅ | Y₁ | Y₂ | Y₃ | Y₄ |
|---|---|---|---|---|---|---|---|---|
| CH₃ | H | H | H | F | —CH₂— | —CH₂— | —NH— | —CH₂— |
| CH₃ | H | H | H | OCH₃ | —CH₂— | —CH₂— | —NH— | —CH₂— |
| CH₃ | H | H | H | CF₃ | —CH₂— | —CH₂— | —NH— | —CH₂— |
| C₂H₅ | H | H | H | CH₃ | —CH₂— | —CH₂— | —NH— | —CH₂— |
| C₂H₅ | H | H | H | Cl | —CH₂— | —CH₂— | —NH— | —CH₂— |
| C₂H₅ | H | H | H | F | —CH₂— | —CH₂— | —NH— | —CH₂— |
| C₂H₅ | H | H | H | OCH₃ | —CH₂— | —CH₂— | —NH— | —CH₂— |
| C₂H₅ | H | H | H | CF₃ | —CH₂— | —CH₂— | —NH— | —CH₂— |
| H | H | H | H | CH₃ | —CH₂— | —CH₂— | —N(CH₃)— | —CH₂— |
| H | H | H | H | Cl | —CH₂— | —CH₂— | —N(CH₃)— | —CH₂— |
| H | H | H | H | F | —CH₂— | —CH₂— | —N(CH₃)— | —CH₂— |
| H | H | H | H | OCH₃ | —CH₂— | —CH₂— | —N(CH₃)— | —CH₂— |
| H | H | H | H | CF₃ | —CH₂— | —CH₂— | —N(CH₃)— | —CH₂— |
| CH₃ | H | H | H | CH₃ | —CH₂— | —CH₂— | —N(CH₃)— | —CH₂— |
| CH₃ | H | H | H | Cl | —CH₂— | —CH₂— | —N(CH₃)— | —CH₂— |
| CH₃ | H | H | H | F | —CH₂— | —CH₂— | —N(CH₃)— | —CH₂— |
| CH₃ | H | H | H | OCH₃ | —CH₂— | —CH₂— | —N(CH₃)— | —CH₂— |
| CH₃ | H | H | H | CF₃ | —CH₂— | —CH₂— | —N(CH₃)— | —CH₂— |

TABLE 22

![Structure with R1-R5 on benzene, Y1-Y4 chain, connected to acylguanidine]

| R₁ | R₂ | R₃ | R₄ | R₅ | Y₁ | Y₂ | Y₃ | Y₄ |
|---|---|---|---|---|---|---|---|---|
| C₂H₅ | H | H | H | CH₃ | —CH₂— | —CH₂— | —N(CH₃)— | —CH₂— |
| C₂H₅ | H | H | H | Cl | —CH₂— | —CH₂— | —N(CH₃)— | —CH₂— |
| C₂H₅ | H | H | H | F | —CH₂— | —CH₂— | —N(CH₃)— | —CH₂— |
| C₂H₅ | H | H | H | OCH₃ | —CH₂— | —CH₂— | —N(CH₃)— | —CH₂— |
| C₂H₅ | H | H | H | CF₃ | —CH₂— | —CH₂— | —N(CH₃)— | —CH₂— |
| H | H | H | H | CH₃ | —CH₂— | —NH— | —CH₂— | —CH₂— |
| H | H | H | H | Cl | —CH₂— | —NH— | —CH₂— | —CH₂— |
| H | H | H | H | F | —CH₂— | —NH— | —CH₂— | —CH₂— |
| H | H | H | H | OCH₃ | —CH₂— | —NH— | —CH₂— | —CH₂— |
| H | H | H | H | CF₃ | —CH₂— | —NH— | —CH₂— | —CH₂— |
| CH₃ | H | H | H | CH₃ | —CH₂— | —NH— | —CH₂— | —CH₂— |
| CH₃ | H | H | H | Cl | —CH₂— | —NH— | —CH₂— | —CH₂— |
| CH₃ | H | H | H | F | —CH₂— | —NH— | —CH₂— | —CH₂— |
| CH₃ | H | H | H | OCH₃ | —CH₂— | —NH— | —CH₂— | —CH₂— |
| CH₃ | H | H | H | CF₃ | —CH₂— | —NH— | —CH₂— | —CH₂— |
| C₂H₅ | H | H | H | CH₃ | —CH₂— | —NH— | —CH₂— | —CH₂— |
| C₂H₅ | H | H | H | Cl | —CH₂— | —NH— | —CH₂— | —CH₂— |
| C₂H₅ | H | H | H | F | —CH₂— | —NH— | —CH₂— | —CH₂— |
| C₂H₅ | H | H | H | OCH₃ | —CH₂— | —NH— | —CH₂— | —CH₂— |
| C₂H₅ | H | H | H | CF₃ | —CH₂— | —NH— | —CH₂— | —CH₂— |
| H | H | H | H | CH₃ | —CH₂— | —N(CH₃)— | —CH₂— | —CH₂— |
| H | H | H | H | Cl | —CH₂— | —N(CH₃)— | —CH₂— | —CH₂— |
| H | H | H | H | F | —CH₂— | —N(CH₃)— | —CH₂— | —CH₂— |
| H | H | H | H | OCH₃ | —CH₂— | —N(CH₃)— | —CH₂— | —CH₂— |

TABLE 22-continued

| $R_1$ | $R_2$ | $R_3$ | $R_4$ | $R_5$ | $Y_1$ | $Y_2$ | $Y_3$ | $Y_4$ |
|---|---|---|---|---|---|---|---|---|
| H | H | H | H | $CF_3$ | —$CH_2$— | —$N(CH_3)$— | —$CH_2$— | —$CH_2$— |
| $CH_3$ | H | H | H | $CH_3$ | —$CH_2$— | —$N(CH_3)$— | —$CH_2$— | —$CH_2$— |
| $CH_3$ | H | H | H | Cl | —$CH_2$— | —$N(CH_3)$— | —$CH_2$— | —$CH_2$— |
| $CH_3$ | H | H | H | F | —$CH_2$— | —$N(CH_3)$— | —$CH_2$— | —$CH_2$— |
| $CH_3$ | H | H | H | $OCH_3$ | —$CH_2$— | —$N(CH_3)$— | —$CH_2$— | —$CH_2$— |
| $CH_3$ | H | H | H | $CF_3$ | —$CH_2$— | —$N(CH_3)$— | —$CH_2$— | —$CH_2$— |
| $C_2H_5$ | H | H | H | $CH_3$ | —$CH_2$— | —$N(CH_3)$— | —$CH_2$— | —$CH_2$— |
| $C_2H_5$ | H | H | H | Cl | —$CH_2$— | —$N(CH_3)$— | —$CH_2$— | —$CH_2$— |
| $C_2H_5$ | H | H | H | F | —$CH_2$— | —$N(CH_3)$— | —$CH_2$— | —$CH_2$— |
| $C_2H_5$ | H | H | H | $OCH_3$ | —$CH_2$— | —$N(CH_3)$— | —$CH_2$— | —$CH_2$— |
| $C_2H_5$ | H | H | H | $CF_3$ | —$CH_2$— | —$N(CH_3)$— | —$CH_2$— | —$CH_2$— |

The compound of the general formula (1) of the present invention has the acylguanidine moiety shown in the above formula (1) and has tautomers. In detail, there are a tautomer [—C(O)N═C(NH$_2$)$_2$] whose acylguanidine moiety is diaminomethyleneamino, and another tautomer [—C(O)NH—C(═NH)NH$_2$] whose acylguanidine moiety is aminoiminomethylamino. These tautomers are different only in state and are the same compound. Therefore, the present invention includes both of the tautomers.

The compound of the general formula (1) includes those having an optical center of asymmetry. The compound having an optical center of asymmetry may be obtained as a racemic modification, or it may be obtained as an optically active substance when an optically active starting material is used. If necessary, the racemic modification obtained may be physically or chemically resolved into optical antipodes by a conventional method. Preferably, diastereomers are formed from the racemic mixture by a reaction using a reagent for optical resolution. The diastereomers different in form may be resolved by a conventional method such as fractional crystallization.

As the "prodrug", there may be exemplified those which are easily hydrolyzed in a living body to regenerate the compound of the formula (1). For example, when the compound of the formula (1) has a carboxyl group, examples of the prodrug are compounds obtained by converting the carboxyl group to an alkoxycarbonyl group, an alkylthiocarbonyl group or an alkylaminocarbonyl group. For example, when the compound of the formula (1) has an amino group, examples of the prodrug are compounds obtained by converting the amino group to an alkanoylamino group by substitution by the alkanoyl group, compounds obtained by converting the amino group to an alkoxycarbonylamino group by substitution by the alkoxycarbonyl group, and compounds obtained by converting the amino group to an acyloxymethylamino group or hydroxylamine. For example, when the compound of the formula (1) has a hydroxyl group, examples of the prodrug are compounds obtained by converting the hydroxyl group to an acyloxy group by substitution by the above-exemplified acyl group, and compounds obtained by converting the hydroxyl group to a phosphoric ester or an acyloxymethyloxy group.

Examples of the alkyl portion of the group used for such conversion to the prodrug are the above-exemplified alkyl groups. The alkyl groups may be substituted by, for example, an alkoxy group of 1 to 6 carbon atoms. Preferable examples of the alkyl portion are as follows. For example, in the case of compounds obtained by converting the carboxyl group to an alkoxycarbonyl group, the alkoxycarbonyl group includes lower (number of carbon atoms: for example, 1 to 6) alkoxycarbonyl groups such as methoxycarbonyl, ethoxycarbonyl, etc.; and lower (number of carbon atoms: for example, 1 to 6) alkoxycarbonyl groups substituted by an alkoxy group, such as methoxymethoxycarbonyl, ethoxymethoxycarbonyl, 2-methoxyethoxycarbonyl, 2-methoxyethoxymethoxycarbonyl, pivaloyloxymethoxycarbonyl, etc.

If necessary, the compound of the general formula (1) or the prodrug thereof may be converted to a pharmaceutically acceptable addition salt with an inorganic acid or an organic acid. As such an acid addition salt, there may be exemplified salts with mineral acids such as hydrochloric acid, hydrobromic acid, sulfuric acid, phosphoric acid, etc.; salts with organic carboxylic acids such as formic acid, acetic acid, fumaric acid, maleic acid, oxalic acid, citric acid, malic acid, tartaric acid, aspartic acid, glutamic acid, etc.; and salts with sulfonic acids such as methanesulfonic acid, benzenesulfonic acid, p-toluenesulfonic acid, hydroxybenzenesulfonic acid, dihydroxybenzenesulfonic acid, etc.

If necessary, the compound of the general formula (1) or the prodrug thereof may be converted to a pharmaceutically acceptable base addition salt in some cases. As such a base addition salt, there may be exemplified ammonium salt, lithium salt, sodium salt, potassium salt, calcium salt and magnesium salt.

Each of the compounds of the general formula (1), the prodrugs thereof and the pharmaceutically acceptable salts of the compounds or prodrug may be in the form of an anhydride, hydrate or solvate.

The compounds of the general formula (1), the prodrugs thereof or the pharmaceutically acceptable salts of the compounds or prodrugs inhibit the sodium/proton ($Na^+/H^+$) exchange transport system and hence are useful as a therapeutic or prophylactic agent for diseases caused by a trouble with the sodium/proton ($Na^+/H^+$) exchange transport system, for example, hypertension, organ disorders associated with ischemia or ischemic reperfusion, arrhythmia, angina pectoris, diabetes mellitus, cardiac hypertrophy, cerebro-ischemic disorders, diseases caused by excessive cell proliferations, or diseases caused by endotherial cell injury.

When used as a pharmaceutical composition, the compound of the present invention, the prodrug thereof or the pharmaceutically acceptable salt of the compound or prodrug may be orally or parenterally administered. That is, the compound, prodrug or salt may be orally administered in a usual dosage form such as powder, granules, tablets, capsules, syrup, suspension or the like, or the compound, prodrug or salt may be parenterally administered, for example, by injection of a solution, emulsion or suspension prepared from the compound, prodrug or salt. The compound, prodrug or salt may be administered rectally in the form of a suppository. The compound, prodrug or salt may be formulated into the above-exemplified suitable dosage form by blending the compound, prodrug or salt as an active ingredient with conventional acceptable adjuvants such as a carrier, excipient, binder, stabilizer and diluent. When the compound, prodrug or salt is used in the form of an injection, the injection may contain acceptable additives such as a buffer, solubilizer and tonicity agent. Although the dose and the number of administrations are varied depending on, for example, a disease to be cured, the condition of the disease, age, body weight and administration route, the compound, prodrug or salt may be administered to an adult in a dose of usually 0.1 to 2,000 mg, preferably 1 to 200 mg per day in one portion or several portions.

The present invention is more concretely illustrated below with reference examples, working examples and test examples, which should not be construed as limiting the scope of the invention. The nomenclature of compounds shown in the reference examples and working examples mentioned below is not always based on IUPAC.

Reference Example 1
Synthesis of Ethyl 3,4-dihydronaphthalene-2-carboxylate
(a) Synthesis of 2-ethoxycarbonyl-3,4-dihydro-1(2H)-naphthalene A mixture of α-tetralone (10.0 g, 68.4 mmol), 60% sodium hydride (2.73 g, 68.4 mmol) and N,N-dimethylformamide (150 ml) was stirred at room temperature for about 1 hour, and diethyl carbonate (8.08 g, 68.4 mmol) was added thereto, followed by stirring at room temperature for 30 minutes and then at 55–60° C. for 1.5 hours. After standing overnight at room temperature, the reaction mixture was poured into cold 1N hydrochloric acid and extracted twice with toluene, and the extract solution was washed twice with a 5% aqueous sodium chloride solution and then distilled under reduced pressure to remove the solvent. The resulting residue was purified by a silica gel column chromatography (eluent; ethyl acetate:n-hexane= 3:97) to obtain 10.4 g of 2-ethoxycarbonyl-3,4-dihydro-1 (2H)-naphthalene.
(b) Synthesis of 2-ethoxycarbonyl-1,2,3,4-tetrahydro-1-naphthol 2-Ethoxycarbonyl-3,4-dihydro-1(2H)-naphthalene (4.00 g, 18.3 mmol) was dissolved in ethanol (60 ml) and the solution was cooled to 0° C. Then, sodium tetrahydroborate (0.69 g, 18.3 mmol) was added thereto, and the resulting mixture was stirred at 0–5° C. for 1.5 hours. After stirring at room temperature for another 1 hour, the reaction mixture was poured into a saturated aqueous ammonium chloride solution and extracted twice with ethyl acetate. The extract solution was washed with a 5% aqueous sodium chloride solution and dried over anhydrous magnesium sulfate. The solvent was distilled off under reduced pressure and the resulting residue was purified by a silica gel column chromatography (eluent; ethyl acetate:n-hexane=5:95) to obtain 2.48 g of 2-ethoxycarbonyl-1,2,3,4-tetrahydro-1-naphthol.
(c) Synthesis of Ethyl 3.4-dihydronaphthalene-2-carboxylate A mixture of 2-ethoxycarbonyl-1,2,3,4-tetrahydro-1-naphthol (2.45 g, 11.1 mmol), triethylamine (2.70 g, 26.7 mmol) and tetrahydrofuran (50 ml) was cooled to 0° C., followed by adding dropwise thereto methanesulfonyl chloride (1.53 g, 13.3 mmol). The reaction mixture was stirred at 0–5° C. for 1.5 hours and then at room temperature for 7 hours, and allowed to stand overnight at room temperature. The reaction mixture was poured into a cold aqueous ammonium chloride solution and extracted twice with ethyl acetate, and the extract solution was washed with a saturated aqueous sodium hydrogencarbonate solution and a 5% aqueous sodium chloride solution and dried over anhydrous magnesium sulfate. The solvent was distilled off under reduced pressure and the resulting residue was purified by a silica gel column chromatography (eluent; ethyl acetate:n-hexane=1:99) to obtain 2.12 g of ethyl 3,4-dihydronaphthalene-2-carboxylate.

$^1$HNMR (CDCl$_3$) δ; 1.35 (3H, t, J=7.2 Hz), 2.58~2.64 (2H, m), 2.84~2.90 (2H, m), 4.24~4.31 (2H, m), 7.15~7.27 (4H, m), 7.52 (1H, s).

Reference Example 2
Synthesis of Ethyl 5-methoxy-3,4-dihydro-naphthalene-2-carboxylate Ethyl 5-methoxy-3,4-dihydronaphthalene-2-carboxylate was synthesized by carrying out reaction according to the method described in Reference Example 1, except for using 5-methoxy-1-tetralone as a starting material.

$^1$HNMR (CDCl$_3$) δ; 1.33~1.39 (3H, m), 2.55~2.61 (2H, m), 2.84~2.89 (2H, m), 3.85 (3H, s), 4.27 (2H, q, J=7.2 Hz), 6.85~6.87 (2H, m), 7.15~7.20 (1H, m), 7.49 (1H, t, J=1.5 Hz).

Reference Example 3
Synthesis of Ethyl 6,7-dihydro-5H-benzocycloheptene-8-carboxylate Ethyl 6,7-dihydro-5H-benzocycloheptene-8-carboxylate was synthesized by carrying out reaction according to the method described in Reference Example 1, except for using 1-benzosuberone as a starting material.

$^1$HNMR (CDCl$_3$) δ; 1.35 (3H, t, J=7.2 Hz), 2.01~2.10 (2H, m), 2.61~2.65 (2H, m), 2.80~2.84 (2H, m), 4.23~4.30 (2H, m), 7.13~7.33 (4H, m).

Reference Example 4
Synthesis of Ethyl 1-(4-methylphenylsulfonyl)-2,3-dihydro-1H-benz[b]azepine-4-carboxylate
(a) Synthesis of Ethyl 1-(4-methylphenylsulfonyl)-1,2,3,4-tetrahydro-5-oxo-1-benz[b]azepine-4-carboxylate Ethyl 1-(4-methylphenylsulfonyl)-1,2,3,4-tetrahydro-5-oxo-1-benz[b]azepine-4-carboxylate was synthesized by carrying out reaction according to the method of Proctor et al. (J. Chem. Soc. Perkin I, (1973), 1803–1808) by using ethyl anthranilate as a starting material.
(b) Synthesis of Ethyl 1-(4-methylphenylsulfonyl)-2,3-dihydro-1H-benz[b]azepine-4-carboxylate Ethyl 1-(4-methylphenylsulfonyl)-2,3-dihydro-1H-benz [b]azepine-4-carboxylate was synthesized by carrying out reaction according to the method described in Reference Example 1, except for using the 1-(4- methylphenylsulfonyl)-1,2,3,4-tetrahydro-5-oxo-1-benz[b]azepine-4-carboxylate synthesized in (a).

$^1$HNMR (CDCl$_3$) δ; 1.30 (3H, t, J=7.2 Hz), 2.34 (3H, s), 2.85~2.89 (2H, m), 3.87~3.91 (2H, m), 4.15~4.22 (2H, m), 7.10 (2H, d, J=8.1 Hz), 7.24~7.41 (6H, m), 7.63 (1H, d, J=7.5 Hz).

Reference Example 5

Synthesis of Ethyl 2.3-dihydro-1H-benz[b]-azepine-4-carboxylate

The ethyl 1-(4-methylphenylsulfonyl)-2,3-dihydro-1H-benz[b]azepine-4-carboxylate (0.63 g, 1.70 mmol) synthesized in Reference Example 4 was added to a mixture of trifluoroacetic acid (10 ml), methanesulfonic acid (0.30 g) and thioanisole (1.0 ml) which had been cooled to 0° C., and the resulting mixture was stirred at room temperature for 3.5 hours. The reaction mixture was poured into cooled aqueous ammonia and extracted twice with ethyl acetate, and the extract solution was washed twice with a saturated aqueous sodium chloride solution and dried over anhydrous magnesium sulfate. The solvent was distilled off under reduced pressure and the resulting residue was purified by a silica gel column chromatography (eluent; ethyl acetate:n-hexane=5:95) to obtain 0.32 g of ethyl 2,3-dihydro-1H-benz[b]azepine-4-carboxylate.

$^1$HNMR (CDCl$_3$) δ; 1.32~1.37 (3H, m), 2.85~2.88 (2H, m), 3.38 (2H, t, J=4.8 Hz), 4.25 (2H, q, J=7.2 Hz), 4.55 (1H, br-s), 6.60 (1H, d, J=7.9 Hz), 6.72~6.77 (1H, m,6.98~7.12 (1H, m), 7.26~7.30 (1H, m), 7.65 (1H, s).

Reference Example 6

Synthesis of Ethyl 2,3-dihydro-benz[b]oxepine-4-carboxylate (a) Synthesis of Ethyl 4-(2-ethoxycarbonylphenyloxy)butyrate A mixture of ethyl salicylate (10.0 g, 60.2 mmol), 60% sodium hydride (2.41 g, 60.2 mmol) and N,N-dimethylformamide (150 ml) w as stirred at room temperature for about 1 hour, followed by adding dropwise thereto ethyl 4-bromobutyrate (12.9 g, 66.2 mmol). The reaction mixture was stirred at room temperature for 4.5 hours and then at 65–70° C. for 2 hours. The reaction mixture was poured into a cooled 5% aqueous sodium chloride solution and extracted twice with ethyl acetate, and the extract solution was washed twice with a 5% aqueous sodium chloride solution and dried over anhydrous magnesium sulfate. The solvent was distilled off under reduced pressure and the resulting residue was purified by a silica gel column chromatography (eluent; ethyl acetate:n-hexane=5:95) to obtain 16.4 g of ethyl 4-(2-ethoxycarbonylphenyloxy)butyrate.

(b) Synthesis of Ethyl 1,2,3,4-tetrahydro-5-oxo-benz[b]oxepine-4-carboxylate

A mixture of ethyl 4-(2-ethoxycarbonylphenyloxy)-butyrate (13.0 g, 46.4 mmol), 60% sodium hydride (5.56 g, 139 mmol), ethanol (2.5 ml) and toluene (250 ml) was stirred at 80–85° C. for 2 hours. The reaction mixture was poured into cold 1N hydrochloric acid and extracted twice with ethyl acetate, and the extract solution was washed with a 5% aqueous sodium chloride solution and dried over anhydrous magnesium sulfate. The solvent was distilled off under reduced pressure and the resulting residue was purified by a silica gel column chromatography (eluent; ethyl acetate:n-hexane=3:97) to obtain 9.05 g of ethyl 1,2,3,4-tetrahydro-5-oxo-benz[b]oxepine-4-carboxylate.

(c) Synthesis of Ethyl 2,3-dihydro-benz[b]oxepine-4-carboxylate

Ethyl 2,3-dihydro-benz[b]oxepine-4-carboxylate was synthesized by carrying out reaction according to the method described in Reference Example, 1 except for using the ethyl 1,2,3,4-tetrahydro-5-oxo-benz[b]oxepine-4-carboxylate synthesized in (b).

$^1$HNMR (CDCl$_3$) δ; 1.35 (3H, t, J=7.2 Hz), 2.96~2.99 (2H, m), 4.24~4.31 (4H, m), 6.96~7.04 (2H, m), 7.21~7.27 (1H, m), 7.33 (1H, d, J=7.5 Hz), 7.58 (1H, s).

Example 1

Synthesis of N-(aminoiminomethyl)-3,4-dihydronaphthalene-2-carboxamide Methanesulfonate A mixture of sodium methoxide (5.34 g, 98.9 mmol), guanidine hydrochloride (9.45 g, 98.9 mmol) and N,N-dimethylformamide (60 ml) was stirred at room temperature for 1 hour. Then, a solution of ethyl 3,4-dihydronaphthalene-2-carboxylate (2.00 g, 9.89 mmol) in N,N-dimethylformamide (20 ml) was added dropwise to the reaction mixture. The resulting mixture was stirred at room temperature for 7 hours and then allowed to stand overnight at room temperature. This reaction mixture was poured into a cold aqueous sodium chloride solution and extracted twice with ethyl acetate, and the extract solution was washed twice with a 5% aqueous sodium chloride solution and dried over anhydrous magnesium sulfate. The solvent was distilled off under reduced pressure to obtain crude N-(aminoiminomethyl)-3,4-dihydronaphthalene-2-carboxamide. This compound was dissolved in isopropyl alcohol, followed by adding thereto excess methanesulfonic acid, and the solid precipitated was collected by filtration and dried under reduced pressure to obtain 2.23 g of N-(aminoiminomethyl)-3,4-dihydronaphthalene-2-carboxamide methanesulfonate.

Melting point: 163–164° C.

Example 2

Synthesis of N-(aminoiminomethyl)-5-methoxy-3,4-dihydronaphthalene-2-carboxamide Methanesulfonate 2.29 Grams of N-(aminoiminomethyl)-5-methoxy-3,4-dihydronaphthalene-2-carboxamide methanesulfonate was obtained by the same process as in Example 1 except for using ethyl 5-methoxy-3,4-dihydronaphthalene-2-carboxylate (1.80 g), sodium methoxide (4.18 g), guanidine hydrochloride (7.40 g) and N,N-dimethylformamide (70 ml).

Melting point: 233–234° C.

Example 3

Synthesis of N-(aminoiminomethyl )-6,7-dihydro-5H-benzocycloheptene-8-carboxamide Methanesulfonate Crude N-h(daminoiminomethyl)-6,7-dihydro-5H-benzocycloheptene-8-carboxamide was obtained by the same process as in Example 1 except for using ethyl 6,7-dihydro-5H-benzocycloheptene-8-carboxylate (1.75 g), sodium methoxide (4.37 g), guanidine hydrochloride (7.73 g) and N,N-dimethylformamide (70 ml). The obtained compound was dissolved in a mixed solvent of isopropyl alcohol and diethyl ether, followed by adding thereto excess methanesulfonic acid, and the solid precipitated was collected by filtration and dried under reduced pressure to obtain 2.19 g of N-(aminoiminomethyl)-6,7-dihydro-5H-benzocycloheptene-8-carboxamide methanesulfonate.

Melting point: 133–135° C.

Example 4

Synthesis of N-(aminoiminomethyl)-1-(4-methylphenylsulfonyl)-2,3-dihydro-1H-benz[b]azepine-4-carboxamide Methanesulfonate 0.23 Gram of N-(aminoiminomethyl)-1-(4-methylphenylsulfonyl)-2,3-dihydro-1H-benz[b]azepine-4- carboxamide methanesulfonate was obtained by the same process as in Example 3 except for using ethyl 1-(4-methylphenylsulfonyl)-2,3-dihydro-1H-benz[b]azepine-4-carboxylate (0.30 g), sodium methoxide (0.87 g), guanidine hydrochloride (1.54 g) and N,N-dimethyl-formamide (40 ml).

Melting point: 228–231° C.

Example 5
Synthesis of N-(aminoiminomethyl)-2,3-dihydro-1H-benz[b]azepine-4-carboxamide dimethane-sulfonate 0.40 Gram of N-(aminoiminomethyl)-2,3-dihydro-1H-benz[b]azepine-4-carboxamide dimethane-sulfonate was obtained by the same process as in Example 1 except for using ethyl 2,3-dihydro-1H-benz[b]azepine-4-carboxylate (0.30 g), sodium methoxide (1.49 g), guanidine hydrochloride (2.64 g) and N,N-dimethylformamide (40 ml).

Melting point: 200–202° C. (decomp.).

Example 6
Synthesis of N-(aminoiminomethyl)-2,3-dihydro-benz[b]oxepine-4-carboxamide Methanesulfonate 2.51 Grams of N-(aminoiminomethyl)-2,3-dihydro-benz[b]oxepine-4-carboxamide methanesulfonate was obtained by the same process as in Example 1 except for using ethyl 2,3-dihydro-benz[b]oxepine-4-carboxylate (2.00 g), sodium methoxide (4.95 g), guanidine hydrochloride (8.75 g) and N,N-dimethyl-formamide (70 ml).

Melting point: 183–185° C.

Reference Example 7
Synthesis of Methyl 5-methyl-6,7-dihydro-5H-benzocycloheptene-8-carboxylate
(a) Synthesis of Ethyl 5-methyl-5-phenyl-4-pentenoate A mixture of potassium tert-butoxide (10.27 g, 91.6 mmol), 3-carboethoxypropyltriphenylphosphonium bromide (41.87 g, 91.6 mmol) and tetrahydrofuran (300 ml) was stirred at room temperature. Acetophenone (10.0 g, 83.2 mmol) was added dropwise to the mixture, and the resulting mixture was stirred at room temperature for another 1 hour and then allowed to stand overnight. Water (100 ml) was added to the reaction mixture, and the resulting mixture was stirred at room temperature for 1 hour, poured into an aqueous sodium chloride solution, and then extracted twice with ethyl acetate. The extract solution was washed with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=2/98) to obtain 17.3 g of ethyl 5-methyl-5-phenyl-4-pentenoate.

$^1$HNMR (CDCl$_3$) δ; 1.23 (3H, t, J=7.2 Hz), 2.02 (3H, d, J=1.1 Hz), 2.21~2.54 (4H, m), 4.06~4.13 (2H, m), 5.41~5.45 (1H, m), 7.14~7.38 (5H, m).
(b) Synthesis of Ethyl 5-methyl-5-phenylpentanoate A mixture of ethyl 5-methyl-5-phenyl-4-pentenoate (17.0 g, 77.9 mmol), ammonium formate (49.1 g, 779 mmol), 10% palladium-carbon (1.7 g) and ethanol (350 ml) was stirred at 70–75° C. for 1 hour. The catalyst was filtered off and the filtrate obtained was concentrated under reduced pressure. The residue was dissolved in ethyl acetate and washed with a 5% aqueous sodium chloride solution. The organic layer was dried over anhydrous magnesium sulfate and then concentrated under reduced pressure, and the resulting residue was purified by a silica gel column chromatography (eluent: ethyl acetate/n-hexane=2/98) to obtain 16.3 g of ethyl 5-methyl-5-phenylpentanoate.

$^1$HNMR (CDCl$_3$) δ; 1.21~1.26 (6H, m), 1.42~1.65 (4H, m), 2.15~2.30 (2H, m), 2.64~2.73 (1H, m), 4.06~4.13 (2H, m), 7.15~7.36 (5H, m).

(c) Synthesis of 5-methyl-5-phenylpentanoic Acid

A mixture of ethyl 5-methyl-5-phenylpentanoate (16.0 g, 72.6 mmol), a 30% aqueous sulfuric acid solution and acetic acid (250 ml) was stirred at 75–80° C. for 6 hours. The reaction mixture was poured into cold water and extracted twice with toluene, and the extract solution was washed twice with a 5% aqueous sodium chloride solution and dried over anhydrous magnesium sulfate. The solvent was distilled off under reduced pressure to obtain 13.4 mg of 5-methyl-5-phenylpentanoic acid.

$^1$HNMR (CDCl$_3$) δ; 1.24 (3H, d, J=7.0Hz), 1.44~1.67 (4H, m), 2.26~2.37 (2H, m), 2.63~2.75 (1H, m), 7.15~7.38 (5H, m).
(d) Synthesis of 9-methyl-6,7,8,9-tetrahydro-5H-benzocyclohepten-5-one 5-Methyl-5-phenylpentanoic acid (13.0 g, 67.6 mmol) was added to polyphosphoric acid (510 g), followed by stirring at 70–75° C. for 2 hours. Ice water was poured into the reaction mixture and stirred, followed by extraction with diethyl ether (twice). The extract solution was washed with a saturated aqueous sodium chloride solution and distilled under reduced pressure to remove the solvent, and the resulting residue was purified by a silica gel column chromatography (eluent: ethyl acetate/n-hexane=3/97) to obtain 9.10 g of 9-methyl-6,7,8,9-tetrahydro-5H-benzocyclohepten-5-one.

$^1$HNMR (CDCl$_3$) δ; 1.38 (3H, d, J=6.6 Hz), 1.48~1.68 (2H, m), 1.82~2.04 (2H, m), 2.54~2.78 (2H, m), 3.04~3.16 (1H, m), 7.25~7.31 (2H, m), 7.44~7.49 (1H, m), 7.52~7.55 (1H, m).

Mass spectrum m/z:174 (M$^+$)
(e) Synthesis of Methyl 5-methyl-6.7-dihydro-5H-benzocycloheptene-8-carboxylate Methyl 5-methyl-6,7-dihydro-5H-benzocycloheptene-8-carboxylate was synthesized by the same process as in Reference Example 1 except for using 9-methyl-6,7,8,9-tetrahydro-5H-benzocyclohepten-5-one.

$^1$HNMR (CDCl$_3$) δ; 1.21 (3H, d, J=7.2 Hz), 1.91~2.05 (2H, m), 2.44~2.57 (1H, m), 3.04~3.22 (1H, m), 3.82 (3H, s), 7.16~7.34 (4H, m), 7.70 (1H, d, J=2.2 Hz).

Reference Example 8
Synthesis of 9-methyl-6,7-dihydro-5H-benzocycloheptene-8-carboxylic Acid
(a) Synthesis of Ethyl 6,7,8,9-tetrahydro-5-oxo-5H-benzocycloheptene-6-carboxylate 5.05 Grams of ethyl 6,7,8,9-tetrahydro-5-oxo-5H-benzocycloheptene-6-carboxylate was obtained by the same process as in Reference Example 1, (a) except for using 1-benzosuberone (5.00 g, 31.2 mmol), 60% sodium hydride (1.25 g, 31.2 mmol), diethyl carbonate (4.06 g, 34.3 mmol) and N,N-dimethylformamide (75 ml).
(b) Synthesis of Ethyl 9-methoxy-6.7-dihydro-5H-benzocycloheptene-8-carboxylate A mixture of ethyl 6,7,8,9-tetrahydro-5-oxo-5H-benzocycloheptene-6-carboxylate (12.0 g, 51.7 mmol), potassium ethoxide (4.78 g, 56.8 mmol) and toluene (200 ml) was stirred at room temperature for 0.5 hour and then distilled under reduced pressure to remove the solvent. The residue was dissolved in N-methylpyrrolidinone (150 ml), followed by adding thereto methyl p-toluenesulfonate (10.6 g, 56.8 mmol), and the resulting mixture was stirred at 55–60° C. for 1 hour. The reaction mixture was poured into a cold aqueous sodium chloride solution and extracted twice with ethyl acetate, and the extract solution was washed twice with a 5% aqueous sodium chloride solution and dried over anhydrous magnesium sulfate. The solvent was distilled off under reduced pressure and the resulting residue was dissolved in ethanol. The resulting solution was cooled to 0° C., followed by adding thereto sodium tetrahydroborate (0.98 g, 25.8 nmol), and the resulting mixture was stirred at 0° C. for 1.5 hours. The reaction mixture was poured into a cold aqueous ammonium chloride solution and extracted twice with ethyl acetate, and the extract solution was washed twice with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=2/98) to obtain 6.66 g of ethyl 9-methoxy-6,7-dihydro-5H-benzocycloheptene-8-carboxylate.

$^1$HNMR (CDCl$_3$) δ; 1.33~1.38 (3H, m), 2.07~2.17 (4H, m), 2.63~2.68 (2H, m), 3.57 (3H, s), 4.27 (2H, dd, J=7.2, 14.1 Hz), 7.23~7.34 (3H, m), 7.41~7.46 (1H, m).

(c) Synthesis of Ethyl 9-methyl-6,7-dihydro-5H-benzocycloheptene-8-carboxylate

A solution of ethyl 9-methoxy-6,7-dihydro-5H-benzocycloheptene-8-carboxylate (4.00 g, 16.2 mmol) in tetrahydrofuran (60 ml) was cooled to −10° C., and methylmagnesium iodide (a 2M diethyl ether solution 16.2 ml, 32.5 mmol) was added dropwise thereto. The reaction mixture was stirred at −5° C. for 2 hours, poured into a cold aqueous ammonium chloride solution and then extracted twice with ethyl acetate. The extract solution was washed with an aqueous sodium hydrogen-carbonate solution and a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=2/98) to obtain 0.81 g of ethyl 9-methyl-6,7-dihydro-5H-benzocycloheptene-8-carboxylate.

$^1$HNMR (CDCl$_3$) δ; 1.35 (3H, t, J=7.2 Hz), 2.05~2.18 (4H, m), 2.40 (3H, s), 2.54~2.66 (2H, m), 4.23~4.30 (2H, m), 7.16~7.40 (4H, m).

(d) Synthesis of 9-methyl-6,7-dihydro-5H-benzocycloheptene-8-carboxylic Acid

Ethyl 9-methyl-6,7-dihydro-5H-benzocycloheptene-8-carboxylate (0.70 g, 3.04 mmol) was added to a mixture of a 2N aqueous sodium hydroxide solution and ethanol, and the resulting mixture was stirred at 70° C. for 5 hours. The reaction mixture was concentrated under reduced pressure and the resulting residue was dissolved in water and washed with ethyl acetate. The aqueous layer was acidified with 35% hydrochloric acid and extracted twice with diethyl ether, and the extract solution was washed with a saturated aqueous sodium chloride solution and then dried over anhydrous magnesium sulfate. The solvent was distilled off under reduced pressure to obtain 0.33 g of 9-methyl-6,7-dihydro-5H-benzocycloheptene-8-carboxylic acid.

$^1$HNMR (CDCl$_3$) δ; 2.1~2.2 (4H, m), 2.50 (3H, s), 2.55~2.60 (2H, m), 7.18~7.34 (4H, m).

Reference Example 9
Synthesis of 4,9-dimethyl-6,7-dihydro-5H-benzocycloheptene-8-carboxylic Acid (a) Synthesis of 1-methyl-6,7,8,9-tetrahydro-5H-benzocyclohepten-5-one 1-Methyl-6,7,8,9-tetrahydro-5H-benzocyclohepten-5-one was synthesized by carrying out reactions according to the methods described in Reference Example 7, (a) to (d), except for using 2-methylbenzaldehyde as a starting material.

Melting point: 54–55° C. (after recrystallization from n-hexane).

$^1$HNMR (CDCl$_3$) δ; 1.71~1.88 (4H, m), 2.36 (3H, s), 2.65~2.69 (2H, m), 2.85~2.89 (2H, m), 7.14~7.19 (1H, m), 7.28~7.30 (1H, m), 7.44 (1H, dd, J=0.9, 7.5 Hz).

(b) Synthesis of 6-[bis(methylthio)methylene]-1-methyl-6,7,8,9-tetrahydro-5H-benzocyclohepten-5-one A suspension prepared by adding sodium tert-butoxide (1.38 g, 14.3 mmol) to a mixture of benzene (5 ml) and N,N-dimethylformamide (3 ml) was cooled to 0° C. with ice, followed by adding thereto 1-methyl-6,7,8,9-tetrahydro-5H-benzocycloheptene-5-one (1.25 g, 7.15 mmol) and carbon disulfide (0.45 ml, 7.15 mmol). Benzene (15 ml) and N,N-dimethylformamide (7 ml) were added thereto and the resulting mixture was stirred at room temperature for 4 hours. Then, the reaction mixture was cooled to 0° C., followed by adding thereto methyl iodide (1.11 ml, 17.8 mmol) and then benzene (10 ml) and N,N-dimethylformamide (5 ml), and the resulting mixture was stirred overnight at room temperature. The reaction mixture was poured into ice water and extracted three times with toluene, and the extract solution was washed with water and dried over anhydrous sodium sulfate. The solvent was distilled off under reduced pressure and the resulting residue was purified by a silica gel column chromatography (eluent: ethyl acetate/n-hexane=1/10) to obtain 1.72 g of 6-[bis(methylthio)methylene]-1-methyl-6,7,8,9-tetrahydro-5H-benzocyclohepten-5-one.

$^1$HNMR (CDCl$_3$) δ; 1.90 (2H, q, J=6.5 Hz), 2.37 (3H, s), 2.43 (3H, s), 2.43 (3H, s), 2.44 (3H, s), 2.73 (2H, t, J=6.5 Hz), 2.75 (2H, t, J=6.5 Hz), 7.20 (1H, t, J=7.5 Hz), 7.32 (1H, d, J=7.5 Hz), 7.67 (1H, d, J=7.5 Hz).

(c) Synthesis of Methyl 4,9-dimethyl-6,7-dihydro-5H-benzocycloheptene-8-carboxylate Diethyl ether (10 ml) was added to methylmagnesium iodide (a 2M-diethyl ether solution, 8.8 ml), and the mixture was cooled to 0° C. Then, a solution of 6-[bis(methylthio)methylene]-1-methyl-6,7,8,9-tetrahydro-5H-benzocyclohepten-5-one (1.61 g, 5.78 mmol) in benzene (10 ml) was added dropwise thereto, and the resulting mixture was stirred at 0° C. for 1 hour. The reaction mixture was poured into a saturated aqueous ammonium chloride solution and extracted twice with ethyl acetate, and the extract solution was washed with water and a saturated aqueous sodium chloride solution and dried over anhydrous sodium sulfate. The solvent was distilled off under reduced pressure and the resulting residue (1.63 g) was added to a trifluoroboron-diethyl ether complex (3 ml) and stirred for 10 minutes. Then, methanol (25 ml) was added thereto and the resulting mixture was heated under reflux for 2 days. The solvent was distilled off under reduced pressure and water was added to the resulting residue, followed by extraction with ethyl acetate (three times). The extract solution was washed with water, a saturated aqueous sodium hydrogen-carbonate solution and a saturated aqueous sodium chloride solution, and then dried over anhydrous magnesium sulfate. The solvent was distilled off under reduced pressure and the resulting residue was purified by a silica gel column chromatography (eluent: ethyl acetate/n-hexane=1/20) to obtain 0.88 g of methyl 4,9-dimethyl-6,7-dihydro-5H-benzocycloheptene-8-carboxylate.

$^1$HNMR (CDCl$_3$) δ; 2.04~2.09 (4H, m), 2.36 (3H, s), 2.41 (3H, s), 2.54~2.59 (2H, m), 3.80 (3H, s), 7.10~7.17 (3H, m).

(d) Synthesis of 4,9-dimethyl-6,7-dihydro-5H-benzocycloheptene-8-carboxylic Acid A 2N-aqueous sodium hydroxide solution (10 ml) was added to a solution of methyl 4,9-dimethyl-6,7-dihydro-5H-benzocycloheptene-8-carboxylate (0.85 g, 3.68 mmol) in methanol (10 ml), and the mixture was heated under reflux for 3 hours. The methanol was distilled off under reduced pressure and the residue was adjusted to pH 1 to 2 with 4N-hydrochloric acid and then extracted three times with ethyl acetate. The extract solution was dried over anhydrous magnesium sulfate. The solvent was distilled off under reduced pressure and the thus obtained solid was washed with n-hexane to obtain 0.56 g of 4,9-dimethyl-6,7-dihydro-5H-benzocycloheptene-8-carboxylic acid.

$^1$HNMR (CDCl$_3$) δ; 2.0~2.2 (4H, m), 2.37 (3H, s), 2.50 (3H, s), 2.58 (2H, t, J=6.2 Hz), 7.11~7.19 (3H, m).

Reference Example 10

Synthesis of Methyl 7-methyl-6,7-dihydro-5H-benzocycloheptene-8-carboxylate (a) Synthesis of Ethyl 5-phenyl-3-methyl-2-pentenoate Ethyl diethylphosphonoacetate (1.67 g, 7.42 mmol) was added dropwise to a solution of potassium tert-butoxide (0.83 g, 7.42 mmol) in tetrahydrofuran (10 ml), followed by stirring at room temperature for 10 minutes. Then, a solution of benzylacetone (1.00 g, 6.75 mmol) in tetrahydrofuran (10 ml) was added drop-wise thereto, and the resulting mixture was stirred at room temperature for 1 hour and then heated under reflux for another 1 hour. The reaction mixture was poured into a 5% aqueous potassium hydrogensulfate solution and extracted with ethyl acetate. The extract solution was washed with water and an aqueous sodium chloride solution and dried over anhydrous magnesium sulfate. The solvent was distilled off under reduced pressure to obtain 1.82 g of ethyl 5-phenyl-3-methyl-2-pentenoate.

(b) Synthesis of Ethyl 5-phenyl-3-methylpentanoate

The ethyl 5-phenyl-3-methyl-2-pentenoate (1.00 g, 4.58 mmol) obtained in the above item (a) was dissolved in ethyl acetate (10 ml), and the resulting solution was subjected to hydrogen catalytic reduction by using 10% palladium-carbon (0.2 g) as a catalyst. The catalyst was filtered off and the filtrate was concentrated under reduced pressure. The resulting residue was purified by a silica gel column chromatography (eluent: ethyl acetate/n-hexane=1/30) to obtain 0.82 g of ethyl 5-phenyl-3-methylpentanoate.

$^1$HNMR (CDCl$_3$) δ; 1.00 (3H, d, J=7.6 Hz), 1.23 (3H, t, J=7.3 Hz), 1.52 (1H, m), 1.69 (1H, m), 2.01 (2H, m), 2.15 (1H, dd, J=7.9, 14.5 Hz), 2.33 (1H, dd, J=5.9, 14.5 Hz), 2.61 (2H, m), 4.11 (2H, q, J=7.3 Hz), 7.15 (3H, m), 7.25 (2H, m).

(c) Synthesis of 5-phenyl-3-methylpentanoic Acid

A mixture of ethyl 5-phenyl-3-methylpentanoate (0.30 g, 1.36 mmol), a 1N-aqueous sodium hydroxide solution (3 ml), methanol (3 ml) and tetrahydrofuran (3 ml) was stirred at room temperature for 5 hours. The reaction mixture was adjusted to pH 1 with a 1N-aqueous hydrochloric acid solution and extracted with ethyl acetate. The extract solution was washed with water and a saturated aqueous sodium chloride solution and dried over anhydrous magnesium sulfate. The solvent was distilled off under reduced pressure to obtain 0.24 g of 5-phenyl-3-methylpentanoic acid.

$^1$HNMR (CDCl$_3$) δ; 1.03 (3H, d, J=6.6 Hz), 1.55 (1H, m), 1.69 (1H, m), 2.02 (2H, m), 2.20 (1H, dd, J=7.9, 14.8 Hz), 2.40 (1H, dd, J=5.9, 14.8 Hz), 2.63 (2H, m), 7.18 (3H, m), 7.27 (2H, m).

(d) Synthesis of 7-methyl-6,7,8,9-tetrahydro-5H-benzocyclohepten-5-one

5-Phenyl-3-methylpentanoic acid (0.10 g, 0.52 mmol) was added to polyphosphoric acid (7 g), and the resulting mixture was stirred at 70° C. for 1 hour. Water was added to the reaction mixture, followed by extraction with ethyl acetate, and the extract solution was washed with water, a saturated aqueous sodium hydrogencarbonate solution and a saturated aqueous sodium chloride solution, and then dried over anhydrous magnesium sulfate. The solvent was distilled off under reduced pressure to obtain 0.07 g of 7-methyl-6,7,8,9-tetrahydro-5H-benzocyclohepten-5-one.

$^1$HNMR (CDCl$_3$) δ; 1.06 (3H, d, J=6.6 Hz), 1.55 (1H, m), 2.05 (2H, m), 2.59 (1H, dd, J=9.1, 14.7 Hz), 2.77 (1H, dd, J=4.1, 14.7 Hz), 2.82 (1H, ddd, J=3.3, 6.1, 15.3 Hz), 3.00 (1H, ddd, J=4.0, 10.2, 15.3 Hz), 7.19 (1H, dd, J=1.7, 7.6 Hz), 7.28 (1H, td, J=1.7, 7.6 Hz), 7.39 (1H, td, J=1.7, 7.6 Hz), 7.72 (1H, dd, J=1.7, 7.6 Hz).

(e) Synthesis of Methyl 7-methyl-6,7-dihydro-5H-benzocycloheptene-8-carboxylate

Methyl 7-methyl-6,7-dihydro-5H-benzocyclo-heptene-8-carboxylate was synthesized by carrying out reaction according to the method described in Reference Example 1, except for using 7-methyl-6,7,8,9-tetrahydro-5H-benzocyclohepten-5-one.

$^1$HNMR (CDCl$_3$) δ; 1.14 (3H, d, J=6.9 Hz), 1.93 (1H, m), 2.83 (1H, ddd, J=2.5, 6.3, 15.8 Hz), 2.97 (1H, ddd, J=2.8, 9.6, 15.8 Hz), 3.23 (1H, m), 3.82 (3H, s), 7.19 (3H, m), 7.33 (1H, m), 7.56 (1H, s).

Reference Example 11

Synthesis of Methyl 6-methyl-6,7-dihydro-5H-benzocycloheptene-8-carboxylate (a) Synthesis of Ethyl 4-methyl-5-phenyl-4-pentenoate Benzyltriphenylphosphonium chloride (29.67 g, 76.30 mmol) was added to a solution of potassium tertbutoxide (9.34 g, 83.24 mmol) in tetrahydrofuran (300 ml), followed by stirring at room temperature for 3 hours, and ethyl levulinate (10.00 g, 69.36 mmol) was added dropwise thereto. The reaction mixture was stirred at room temperature for 2 hours and then heated under reflux for another 2 hours. The reaction mixture was adjusted to pH 1 with a 1N-aqueous hydrochloric acid solution and extracted with ethyl acetate, and the extract solution was washed with water and a saturated aqueous sodium chloride solution and dried over anhydrous magnesium sulfate. The solvent was distilled off under reduced pressure and the resulting residue was purified by a silica gel column chromatography (eluent: ethyl acetate/n-hexane=1/25) to obtain 9.20 g of ethyl 4-methyl-5-phenyl-4-pentenoate.

$^1$HNMR (CDCl$_3$) δ; 1.26 (3H, t, J=7.3 Hz), 1.86 (3H, s), 2.42~2.60 (4H, m), 4.15 (2H, q, J=7.3 Hz), 6.30 (1H, d, J=7.9 Hz), 7.16~7.22 (3H, m), 7.31 (2H, td, J=1.3, 7.3 Hz).

(b) Synthesis of Methyl 6-methyl-6,7-dihydro-5H-benzocycloheptene-8-carboxylate

Methyl 6-methyl-6,7-dihydro-5H-benzocyclo-heptene-8-carboxylate was synthesized by the same process as in Reference Example 10, (b) to (e) except for using the ethyl 4-methyl-5-phenyl-4-pentenoate obtained in the above item (a).

$^1$HNMR (CDCl$_3$) δ; 1.06 (3H, d, J=6.6 Hz), 2.17 (1H, dd, J=8.6, 15.8 Hz), 2.32~2.43 (1H, m), 2.52 (1H, dd, J=7.3, 13.9 Hz), 2.60 (1H, dd, J=5.0, 15.8 Hz), 2.72 (1H, dd, J=4.0, 13.9 Hz), 3.82 (3H, s), 7.14~7.29 (4H, m), 7.73 (1H, s).

Reference Example 12

Synthesis of 1-nitro-6,7,8,9-tetrahydro-5H-benzocyclohepten-5-one and 3-nitro-6,7,8,9-tetrahydro-5H-benzocyclohepten-5-one A solution of 1-benzosuberone (0.20 g, 1.2 mmol) in chloroform (2 ml) and then 70% nitric acid (1 ml) were added dropwise to concentrated sulfuric acid (2 ml) under ice-cooling. After stirring under ice-cooling for 30 minutes, the reaction mixture was poured into ice water, neutralized with sodium hydrogen-carbonate, and then extracted with ethyl acetate. The extract solution was washed with a saturated aqueous sodium chloride solution and then dried over anhydrous magnesium sulfate. The solvent was distilled off under reduced pressure and the resulting residue was separated and purified by a silica gel column chromatography (eluent: ethyl acetate/n-hexane=1/7) to obtain the 1-nitro isomer (0.02 g) and the 3-nitro isomer (0.19 g).

1-Nitro-6,7,8,9-tetrahydro-5H-benzocyclohepten-5-one $^1$HNMR (CDCl$_3$) δ; 1.83 (2H, t, J=6.2 Hz), 2.01 (2H, t, J=6.8 Hz), 2.74 (2H, t, J=5.6 Hz), 2.98 (2H, t, J=6.4 Hz), 7.44 (1H, t, J=7.9 Hz), 7.81 (1H, dd, J=1.1, 7.7 Hz), 7.90 (1H, dd, J=1.3, 8.0 Hz).

3-Nitro-6,7,8,9-tetrahydro-5H-benzocyclohepten-5-one $^1$HNMR (CDCl$_3$) δ; 1.80~2.01 (4H, m), 2.80 (2H, t, J=6.2 Hz), 3.05 (2H, t, J=5.9 Hz), 7.40 (1H, d, J=8.2 Hz), 8.25 (1H, dd, J=2.6, 8.3 Hz), 8.55 (1H, d, J=2.4 Hz).

Reference Example 13

Synthesis of Methyl 2-methylthio-6,7-dihydro-5H-benzocycloheptene-8-carboxylate (a) Synthesis of 3-amino-6,7,8,9-tetrahydro-5H-benzocyclohepten-5-one A mixture of 3-nitro-6,7,8,9-tetrahydro-5H-benzocyclohepten-5-one (10.0 g, 48.73 mmol), tin(II) chloride dihydrate (49.48 g, 219.3 mmol) and ethanol (200 ml) was stirred at 70° C. for 2 hours. The reaction mixture was poured into ice water, adjusted to pH 10 with sodium hydroxide, and then extracted with toluene. The extract solution was washed with water and a saturated aqueous sodium chloride solution and dried over anhydrous magnesium sulfate. The solvent was distilled off under reduced pressure and the resulting residue was purified by a silica gel column chromatography (eluent: ethyl acetate/n-hexane=1/2) to obtain 8.08 g of 3-amino-6,7,8,9-tetrahydro-5H-benzocyclohepten-5-one.

$^1$HNMR (CDCl$_3$) δ; 1.80 (4H, m), 2.70 (2H, m), 2.82 (2H, m), 3.69 (2H, brs), 6.75 (1H, dd, J=2.6, 7.9 Hz), 6.98 (1H, d, J=7.9 Hz), 7.05 (1H, d, J=2.6 Hz).

(b) Synthesis 3-methylthio-6,7,8,9-tetrahydro-5H-benzocyclohepten-5-one

A solution of sodium sulfite (3.31 g, 47.94 mmol) in water (5 ml) was added dropwise to a mixture of 3-amino-6,7,8,9-tetrahydro-5H-benzocyclohepten-5-one (8.00 g, 45.65 mmol) and 35% hydrochloric acid (20 ml) under ice-cooling and stirred under ice-cooling for 20 minutes. Sodium acetate trihydrate (33 g) was added to the reaction mixture and the resulting mixture was added dropwise to a 15% aqueous sodium thiomethoxide solution (42.67 g, 91.31 mmol). The reaction mixture was stirred at 80° C. for 1.5 hours, adjusted to pH 9 with an aqueous sodium hydroxide solution and then extracted with ethyl acetate. The extract solution was washed with water and a saturated aqueous sodium chloride solution and dried over anhydrous magnesium sulfate. The solvent was distilled off under reduced pressure and the resulting residue was purified by a silica gel column chromatography (eluent: ethyl acetate/n-hexane=1/30) to obtain 4.33 g of 3-methylthio-6,7,8,9-tetrahydro-5H-benzocyclohepten-5-one.

$^1$HNMR (CDCl$_3$) δ; 1.85 (4H, m), 2.49 (3H, s), 2.73 (2H, m), 2.89 (2H, m), 7.71 (1H, d, J=7.9 Hz), 7.30 (1H, dd, J=2.0, 7.9 Hz), 7.59 (1H, d, J=2.0 Hz).

(c) Synthesis of Methyl 2-methylthio-6,7-dihydro-5H-benzocycloheptene-8-carboxylate Methyl 2-methylthio-6,7-dihydro-5H-benzocycloheptene-8-carboxylate was synthesized by carrying out reactions according to the methods described in Reference Example 1, (a) to (c), except for using the 3-methylthio-6,7,8,9-tetrahydro-5H-benzocyclohepten-5-one obtained in the above item (b).

$^1$HNMR (CDCl$_3$) δ; 2.02 (2H, m), 2.47 (3H, s), 2.62 (2H, m), 2.76 (2H, m), 3.81 (3H, s), 7.06 (1H, d, J=7.9 Hz), 7.12 (1, dd, J=2.0, 7.0 Hz), 7.20 (1H, d, J=2.0 Hz), 7.65 (1H, s).

Reference Example 14

Synthesis of Methyl 2methylsulfonyl-6,7-dihydro-5H-benzocycloheptene-8-carboxylate Methyl 2-methylthio-6,7-dihydro-5H-benzocycloheptene-8-carboxylate (0.04 g, 0.15 mmol) was dissolved in acetic acid (2 ml), followed by adding thereto a 30% aqueous hydrogen peroxide solution (0.1 ml, 0.91 mmol), and the resulting mixture was stirred at 50° C. for 1 hour. Toluene was added to the reaction mixture and the resulting mixture was concentrated under reduced pressure. The resulting residue was purified by a silica gel column chromatography (eluent: ethyl acetate/n-hexane=1/2) to obtain 0.033 g of methyl 2-methylsulfonyl-6,7-dihydro-5H-benzocycloheptene-8-carboxylate.

$^1$HNMR (CDCl$_3$) δ; 2.09 (2H, m), 2.67 (2H, m), 2.89 ((2H, m), 3.06 (3H, s), 3.84 (3H, s), 3.84 (3H, s), 7.36 (1H, d, J=7.9 Hz), 7.72 (1H, s), 7.77 (1H, dd, J<1.7, 7.9 Hz), 7.87 (1H, d, J=1.7 Hz).

IR (KBr) cm$^{-1}$; 2953, 1714, 1629, 1435, 1294, 1235, 1197, 1147, 1125, 972.

Reference Example 15

Synthesis of Methyl 4-methylthio-6,7-dihydro-5H-benzocycloheptene-8-carboxylate

Methyl 4-methylthio-6,7-dihydro-5H-benzocycloheptene-8-carboxylate was synthesized by the same process as described in Reference Example 13, except for using the 1-nitro-6,7,8,9-tetrahydro-5H-benzocyclohepten-8-one obtained in Reference Example 12.

$^1$HNMR (CDCl$_3$) δ; 2.15 (2H, m), 2.45 (3H, s), 2.50 (2H, m), 2.91 (2H, m), 3.82 (3H, s), 7.10 (1H, m), 7.20 (2H, m), 7.71 (1H, s).

Reference Example 16

Synthesis of Methyl 4-methylsulfonyl-6,7-dihydro-5H-benzocycloheptene-8-carboxylate Methyl 4-methylthio-6,7-dihydro-5H-benzocycloheptene-8-carboxylate (0.50 g, 2.01 mmol) was dissolved in methanol (10 ml), followed by adding thereto a 30% aqueous hydrogen peroxide solution (1.14 ml, 10.07 mmol) and sodium tungstate dihydrate (0.066 g, 0.201 mmol), and the resulting mixture was stirred at 70° C. for 5.5 hours. Water was added to the reaction mixture, followed by extraction with ethyl acetate (twice), and the extract solution was washed with water and a saturated aqueous sodium chloride solution and then dried over anhydrous magnesium sulfate. The solvent was distilled off under reduced pressure to obtain 0.589 g of methyl 4-methylsulfonyl-6,7-dihydro-5H-benzocycloheptene-8-carboxylate.

$^1$HNMR (CDCl$_3$) δ; 2.29 (2H, m), 2.48 (2H, m), 3.12 (2H, m), 3.14 (3H, s), 3.85 (3H, s), 7.42 (1H, t, J=7.9 Hz), 7.51 (1H, dd, J=1.7, 7.9 Hz), 7.75 (1H, s), 8.04 (1H, dd, J=1.7, 7.9 Hz).

IR (KBr) cm$^{-1}$; 2943, 2361, 1712, 1627, 1449, 1289, 1214, 1148, 1116, 1087.

Example 7

Synthesis of N-(aminoiminomethyl)-5-methyl-6,7-dihydro-5H-benzocycloheptene-8-carboxamide Methanesulfonate 2.83 Grams of N-(aminoiminomethyl)-5-methyl-6,7-dihydro-5H-benzocycloheptene-8-carboxamide methanesulfonate was obtained by the same process as in Example 3 except for using methyl 5-methyl-6,7-dihydro-5H-benzocycloheptene-8-carboxylate (2.50 g, 10.9 mmol), guanidine hydrochloride (10.37 g, 109 mmol), sodium methoxide (5.86 g, 109 mmol) and N,N-dimethylformamide (100 ml).

Melting point: 163–164° C.

Example 8
Synthesis of N-(aminoiminomethyl)-9-methyl-6,7-dihydro-5H-benzocycloheptene-8-carboxamide Methanesulfonate A mixture of 9-methyl-6,7-dihydro-5H-benzocycloheptene-8-carboxylic acid (0.30 g, 1.48 mmol), N,N'-carbonyldiimidazole (0.36 g, 2.22 mmol) and N,N-dimethylformamide (20 ml) was stirred at room temperature for 2 hours and then added dropwise to a mixture of guanidine hydrochloride (2.83 g, 29.7 mmol), NaOMe (1.60 g, 29.7 mmol) and N,N-dimethylformamide (30 ml). The reaction mixture was stirred at 0–5° C. for 6 hours, poured into a cold aqueous sodium chloride solution, and then extracted twice with ethyl acetate. The extract solution was washed twice with an aqueous sodium chloride solution and dried over anhydrous magnesium sulfate. The solvent was distilled off under reduced pressure and the resulting residue was dissolved in a mixed solvent of 2-propanol and diethyl ether. Methanesulfonic acid was added thereto and the solid precipitated was collected by filtration and then dried under reduced pressure to obtain 0.39 g of N-(aminoiminomethyl)-9-methyl-6,7-dihydro-5H-benzocycloheptene-8-carboxamide methanesulfonate.

Melting point: 184–185° C.

Example 9
Synthesis of N-(aminoiminomethyl)-4,9-dimethyl-6,7-dihydro-5H-benzocycloheptene-8-carboxamide Methanesulfonate 0.64 Gram of N-(aminoiminomethyl)-4,9-dimethyl-6,7-dihydro-5H-benzocycloheptene-8-carboxamide methanesulfonate was obtained by the same process as in Example 8 except for using 4,9-dimethyl-6,7-dihydro-5H-benzocycloheptene-8-carboxylic acid (0.53 g).

Melting point: 193° C. (after recrystallization from a mixed solvent of water and 2-propanol).

Example 10
Synthesis of N-(aminoiminomethyl)-7-methyl-6,7-dihydro-5H-benzocycloheptene-8-carboxamide Methanesulfonate 0.50 Gram of N-(aminoiminomethyl)-7-methyl-6,7-dihydro-5H-benzocycloheptene-8-carboxamide methanesulfonate was obtained by the same process as in Example 3 except for using methyl 7-methyl-6,7-dihydro-5H-benzocycloheptene-8-carboxylate (1.20 g, 5.55 mmol), guanidine hydrochloride (5.30 g, 55.48 mmol), sodium methoxide (3.00 g, 55.48 mmol) and N,N-dimethylformamide (40 ml).

Melting point: 134.5° C.

Example 11
Synthesis of N-(aminoiminomethyl)-6-methyl-6.7-dihydro-5H-benzocycloheptene-8-carboxamide Methanesulfonate 1.16 Grams of N-(aminoiminomethyl)-6-methyl-6,7-dihydro-5H-benzocycloheptene-8-carboxamide methanesulfonate was obtained by the same process as in Example 3 except for using methyl 6-methyl-6,7-dihydro-5H-benzocycloheptene-8-carboxylate (1.00 g, 4.62 mmol), guanidine hydrochloride (4.42 g, 46.24 mmol), sodium methoxide (2.50 g, 46.24 mmol) and N,N-dimethylformamide (46 ml).

Melting point: 170.5° C.

Example 12
Synthesis of N-(aminoiminomethyl)-2-methylthio-6,7-dihydro-5H-benzocycloheptene-8-carboxamide Methanesulfonate 0.41 Gram of N-(aminoiminomethyl)-2-methylthio-6,7-dihydro-5H-benzocycloheptene-8-carboxamide methanesulfonate was obtained by the same process as in Example 3 except for using methyl 2-methylthio-6,7-dihydro-5H-benzocycloheptene-8-carboxylate (0.33 g, 1.33 mmol), guanidine hydrochloride (1.27 g, 13.29 mmol), sodium methoxide (0.72 g, 13.29 mmol) and N,N-dimethylformamide (13 ml).

Melting point: 199.0–199.5° C.

Example 13
Synthesis of N-(aminoiminomethyl)-2-methylsulfonyl-6,7-dihydro-5H-benzocycloheptene-8-carboxamide Methanesulfonate 0.34 Gram of N-(aminoiminomethyl)-2-methylsulfonyl-6,7-dihydro-5H-benzocycloheptene-8-carboxamide methanesulfonate was obtained by the same process as in Example 3 except for using methyl 2-methylsulfonyl-6,7-dihydro-5H-benzocycloheptene-8-carboxylate (0.35 g, 1.25 mmol), guanidine hydrochloride (1.19 g, 12.48 mmol), sodium methoxide (0.67 g, 12.48 mmol) and N,N-dimethylformamide (13 ml).

Melting point: 242–243° C.

Example 14
Synthesis of N-(aminoiminomethyl)-4-methylthio-6,7-dihydro-5H-benzocycloheptene-8-carboxamide Methanesulfonate 0.52 Gram of N-(aminoiminomethyl)-4-methylthio-6,7-dihydro-5H-benzocycloheptene-8-carboxamide methanesulfonate was obtained by the same process as in Example 3 except for using methyl 4-methylthio-6,7-dihydro-5H-benzocycloheptene-8-carboxylate (0.40 g, 1.61 mmol), guanidine hydrochloride (1.54 g, 16.11 mmol), sodium methoxide (0.87 g, 16.11 mmol) and N,N-dimethylformamide (19 ml).

Melting point: 191–192° C.

Example 15
Synthesis of N-(aminoiminomethyl)-4-methylsulfonyl-6,7-dihydro-5H-benzocycloheptene-8-carboxamide Methanesulfonate 0.46 Gram of N-(aminoiminomethyl)-4-methylsulfonyl-6,7-dihydro-5H-benzocycloheptene-8-carboxamide methanesulfonate was obtained by the same process as in Example 3 except for using methyl 4-methylsulfonyl-6,7-dihydro-5H-benzocycloheptene-8-carboxylate (0.40 g, 1.43 mmol), guanidine hydrochloride (1.36 g, 14.27 mmol), sodium methoxide (0.77 g, 14.27 mmol) and N,N-dimethylformamide (14 ml).

Melting point: 203–204° C.

Reference Example 17
Synthesis of Ethyl 1-methyl-2,3-dihydro-1H-benz[b]azepine-4-carboxylate A 37% aqueous formaldehyde solution (1.50 g, 18.4 mmol), sodium cyanotrihydroborate (0.12 g, 18.4 mmol) and acetic acid (0.1 ml) were added to a solution in acetonitrile (8 ml) of the ethyl 2,3-dihydro-1H-benz[b]azepine-4-carboxylate (0.40 g, 1.84 mmol) synthesized in Reference Example 5. After stirring at room temperature for 2 hours, the reaction mixture was poured into a 1N aqueous sodium hydroxide solution and extracted twice with diethyl ether. The extract solution was washed twice with a 5% aqueous sodium chloride solution and dried over anhydrous magnesium sulfate. The solvent was distilled off under reduced pressure and the resulting residue was purified by a silica gel column chromatography (eluent: ethyl acetate/n-hexane=4/96) to obtain 0.40 g of ethyl 1-methyl-2,3-dihydro-1H-benz[b]azepine-4-carboxylate.

$^1$HNMR (CDCl$_3$) δ; 1.34 (3H, t, J=7.2 Hz), 2.83~2.86 (2H, m), 3.03 (3H, s), 3.23~3.26 (2H, m), 4.22~4.29 (2H, m), 6.77~6.82 (2H, m), 7.18~7.24 (1H, m), 7.31~7.33 (1H, m), 7.69 (1H, s).

Reference Example 18
Synthesis of Methyl 5-(2-propyl)-6.7-dihydro-5H-benzocycloheptene-8-carboxylate
(a) Synthesis of Ethyl 5-phenyl-5-(2-propyl)-4-pentenoate 3-Ethoxycarbonylpropyltriphenylphosphonium bromide (73.3.g, 160 mmol) was added to a solution of potassium tert-butoxide (18.5 g, 160 mmol) in tetrahydrofuran (1000 ml) and stirred for 3 hours, and then isobutyrophenone (20.0 g, 135 mmol) was added thereto and stirred for 3 days. After water (200 ml) was added thereto and stirred for 30 minutes, the reaction mixture was added to an aqueous sodium chloride solution and extracted twice with ethyl acetate. The extract solution was washed with a saturated aqueous sodium chloride solution and dried over anhydrous magnesium sulfate. The solvent was distilled off under reduced pressure and the resulting residue was treated by a silica gel column chromatography (eluent: ethyl acetate/n-hexane=1/20) to obtain crude ethyl 5-phenyl-5-(2-propyl)-4-pentenoate (24.6 g; containing starting isobutyrophenone). This crude product was treated with sodium tetrahydroborate (2.83 g) in ethanol and then purified by a silica gel column chromatography (eluent: ethyl acetate/n-hexane=1/40) to obtain 10.0 g of ethyl 5-phenyl-5-(2-propyl)-4-pentenoate.

$^1$HNMR (CDCl$_3$) δ; 0.98 (6H, d, J=6.4 Hz), 1.23 (3H, t, J=7.2 Hz), 2.09–2.18 (2H, m), 2.23~2.29 (2H, m), 2.48–2.58 (1H, m), 4.09 (2H, q, J=7.2 Hz), 5.38 (1H, td, J=1.2, 7.1 Hz), 7.04–7.08 (2H, m), 7.24–7.36 (3H, m).

(b) Synthesis of 5-phenyl-5-(2-propyl)pentanoic Acid

5-Phenyl-5-(2-propyl)pentanoic acid was synthesized by carrying out reactions according to the methods described in Reference Example 10, (b) and (c), except for using ethyl 5-phenyl-5-(2-propyl)-4-pentenoate.

$^1$HNMR (CDCl$_3$) δ; 0.70 (3H, d, J=6.8 Hz), 0.93 (3H, d, J=6.4 Hz), 1.40 (2H, q, J=7.4 Hz), 1.54–1.69 (1H, m), 1.72–1.87 (2H, m), 2.20–2.31 (3H, m), 7.08–7.31 (5H, nm), 10.5 (1H, brs).

(c) Synthesis of 9-(2-propyl)-6,7,8,9-tetrahydro-5H-benzocyclohepten-5-one

Thionyl chloride (5.6 ml, 77 mmol) was added to a solution of 5-phenyl-5-(2-propyl)pentanoic acid (8.35 g, 37.9 mmol) in chloroform (50 ml), followed by heating under reflux for 3.5 hours. Then, thionyl chloride (3.0 ml, 41 mmol) was added thereto and the resulting mixture was heated under reflux for 1 hour. The reaction mixture was concentrated under reduced pressure and the resulting residue was dissolved in 1,2-dichloroethane (20 ml). The resulting solution was added dropwise to a suspension of aluminum chloride (10.1 g, 75.8 mmol) in 1,2-dichloroethane (100 ml) which had been cooled to 0° C., and the resulting mixture was stirred at 0° C. for 10 minutes. The reaction mixture was poured into a cold 1N hydrochloric acid and extracted twice with ethyl acetate, and the extract solution was washed twice with a saturated aqueous sodium chloride solution and dried over anhydrous magnesium sulfate. The solvent was distilled off under reduced pressure and the resulting residue was purified by a silica gel column chromatography (eluent: ethyl acetate/n-hexane=1/10) to obtain 6.83 g of 9-(2-propyl)-6,7,8,9-tetrahydro-5H-benzocyclohepten-5-one.

$^1$HNMR (CDCl$_3$) δ; 0.68 (3H, d, J=6.4 Hz), 1.04 (3H, d, J=6.4 Hz), 1.7~2.1 (5H, m), 2.40~2.49 (1H, m), 2.56–2.76 (2H, m), 7.15–7.20 (1H, m), 7.23–7.30 (1H, m), 7.36–7.42 (2H, m)

(d) Synthesis of Methyl 5-(2-propyl)-6,7-dihydro-5H-benzocycloheptene-8-carboxylate Methyl 5-(2-propyl)-6,7-dihydro-5H-benzocycloheptene-8-carboxylate was synthesized by carrying gut reaction according to the method described in Reference Example 1, except for using 9-(2-propyl)-6,7,8,9-tetrahydro-5H-benzocyclohepten-5-one.

$^1$HNMR (CDCl$_3$) δ; 0.62 (3H, d, J=6.6 Hz), 1.03 (3H, d, J=6.9 Hz), 1.75–1.96 (2H, m), 2.19–2.31 (1H, m), 2.50–2.58 (1H, m), 2.66–2.84 (2H, m), 3.81 (3H, s), 7.06–7.12 (1H, m), 7.16–7.24 (2H, m), 7.32–7.36 (1H, m), 7.64–7.68 (1H, m).

Reference Example 19
Synthesis of Methyl 5-ethyl-6,7-dihydro-5H-benzocycloheptene-8-carboxylate
(a) Synthesis of 9-ethyl-6,7,8,9-tetrahydro-5H-benzocyclohepten-5-one 9-Ethyl-6,7,8,9-tetrahydro-5H-benzocyclo-hepten-5-one was synthesized by the same process as in Reference Example 7, (a) to (d) except for using propiophenone as a starting material.

$^1$HNMR (CDCl$_3$) δ; 0.93 (3H, t, J=7.3 Hz), 1.40–2.17 (6H, m), 2.55–2.71 (2H, m), 2.73–2.83 (1H, m), 7.21 (1H, d, J=7.5 Hz), 7.26–7.31 (1H, m), 7.43 (1H, dd, J=1.5, 7.5 Hz), 7.49 (1H, dd, J=1.2, 7.5 Hz).

(b) Synthesis of 6-[bis(methylthio)methylene]-9-ethyl-6,7,8,9-tetrahydro-5H-benzocyclohepten-5-one 6-[Bis(methylthio)methylene]-9-ethyl-6,7,8,9-tetrahydro-5H-benzocyclohepten-5-one was synthesized by the same process as in Reference Example 9, (b) except for using 9-ethyl-6,7,8,9-tetrahydro-5H-benzocyclohepten-5-one.

$^1$HNMR (CDCl$_3$) δ; 0.92 (3H, t, J=7.3 Hz), 1.49–1.59 (1H, m), 1.63–1.75 (1H, m), 1.79–1.91 (1H, m), 2.06–2.18 (1H, m), 2.27–2.38 (1H, m), 2.43 (3H, s), 2.48 (3H, s), 2.63–2.73 (1H, m), 3.10–3.18 (1H, m), 7.77 (1H, dd, J=1.5, 7.5 Hz), 7.23 (1H, d, J=7.7 Hz), 7.32 (1H, dt, J=1.1, 7.5 Hz), 7.47 (1H, dt, J=1.5, 7.5 Hz).

(c) Synthesis of methyl 5-ethyl-6,7-dihydro-5H-benzocycloheptene-8-carboxylate

6-[Bis(methylthio)methylene]-9-ethyl-6,7,8,9-tetrahydro-5H-benzocyclohepten-5-one (0.35 g, 1.31 mmol) was dissolved in ethanol (7 ml), followed by adding thereto sodium tetrahydroborate (0.16 g, 4.35 mmol), and the reaction mixture was heated under reflux for 2 hours. The reaction mixture was poured into ice water and extracted with ethyl acetate, and the extract solution was washed with a saturated aqueous sodium chloride solution and dried over anhydrous magnesium sulfate. The solvent was distilled off under reduced pressure, and boron trifluoride diethyl ether complex (0.56 g, 3.95 mmol) was added to the residue, followed by stirring at room temperature for 20 minutes. Then, methanol (5 ml) was added thereto and the resulting mixture was heated under reflux for 3 hours. The reaction mixture was poured into ice water and extracted with ethyl acetate, and the extract solution was washed with a saturated aqueous sodium chloride solution and dried over anhydrous magnesium sulfate. The solvent was distilled off under reduced pressure and the resulting residue was purified by a silica gel column chromatography to obtain 0.20 g of methyl 5-ethyl-6,7-dihydro-5H-benzocycloheptene-8-carboxylate.

$^1$HNMR (CDCl$_3$) δ; 0.89 (3H, t, J=7.4 Hz), 1.50–1.61 (2H, m), 1.91–2.00 (1H, m), 2.04–2.14 (1H, m), 2.51–2.65 (1H, m), 2.74–2.87 (2H, m), 3.81 (3H, s), 7.14– 7.36 (4H, m), 7.68 (1H, d, J=2.0Hz).

Reference Example 20
Synthesis of 7,7-dimethyl-6.7-dihydro-5H-benzocycloheptene-8-carboxylic Acid
(a) Synthesis of 3,3-dimethyl-5-oxo-5-phenylpentanoic Acid A mixture of 3,3-dimethylglutaric anhydride (10.0 g, 70.4 mmol), anhydrous aluminum chloride (23.5 g, 176 mmol) and benzene (100 ml) was heated under reflux for 5 hours. The reaction mixture was poured into ice water, adjusted to pH 1 with a 35% hydrochloric acid and then extracted with ethyl acetate. The extract solution was washed with water and a saturated aqueous sodium chloride solution and dried over anhydrous magnesium sulfate. The solvent was distilled off under reduced pressure to obtain 17.4 g of 3,3-dimethyl-5-oxo-5-phenylpentanoic acid.

$^1$HNMR (CDCl$_3$) δ; 1.18 (6H, s), 2.60 (2H, s), 3.12 (2H, s), 7.45 (2H, td, J=1.3, 8.3 Hz), 7.56 (1H, td, J=1.3, 8.3 Hz), 7.95 (2H, dd, J=1.3, 8.3 Hz).

(b) Synthesis of 3,3-dimethyl-5-phenylpentanoic Acid 3,3-Dimethyl-5-oxo-5-phenylpentanoic acid (17.0 g, 77.2 mmol) was subjected to hydrogen catalytic reduction in acetic acid (170 ml) by using 10% palladium-carbon as a catalyst. After completion of the reaction, the catalyst was filtered off and the solvent was distilled off under reduced pressure to obtain 14.2 g of 3,3-dimethyl-5-phenylpentanoic acid.

$^1$HNMR (CDCl$_3$) δ; 1.12 (6H, s), 1.63–1.70 (2H, m), 2.33 (2H, s), 2.58–2.64 (2H, m), 7.14–7.30 (5H, m).

(c) Synthesis of Monomethyl(1,1-dimethyl-3-phenylpropyl)propanedioate

Diisopropylamine (25.1 ml, 179 mmol) was dissolved in tetrahydrofuran (100 ml) and the solution was cooled to −72° C. Then, n-butyllithiium (a 3 M n-hexane solution; 57.4 ml, 172 mmol) was added dropwise thereto, followed by stirring at −5° C. for 30 minutes. After the reaction mixture was re-cooled to −70° C., a solution of 3,3-dimethyl-5-phenylpentanoic acid (14.2 g, 68.8 mmol) in tetrahydrofuran (100 ml) was added dropwise thereto and stirred for another 30 minutes, and dimethyl carbonate (9.30 g, 103 mmol) was added dropwise thereto. The resulting mixture was stirred at −5° C. for 2 hours and then at room temperature for 1.5 hours. The reaction mixture was adjusted to pH 1 with 1N hydrochloric acid and extracted with ethyl acetate, and the extract solution was washed with water and a saturated aqueous sodium chloride solution and dried over anhydrous magnesium sulfate. The solvent was distilled off under reduced pressure and the resulting residue was purified by a silica gel column chromatography to obtain 7.91 g of monomethyl (1,1-dimethyl-3-phenylpropyl)propanedioate.

$^1$HNMR (CDCl$_3$) δ; 1.20 (3H, s), 1.21 (3H, s), 1.71–1.78 (2H, m), 2.11 (1H, s), 2.59–2.66 (2H, m), 3.49 (1H, s), 3.77 (3H, s), 7.16–7.20 (3H, m), 7.25–7.31 (2H, m).

(d) Synthesis of 7,7-dimethyl-6-methoxycarbonyl-6,7,8,9-tetrahydro-5H-benzocyclohepten-5-one 7,7-Dimethyl-6-methoxycarbonyl-6,7,8,9-tetrahydro-5H-benzocyclohepten-5-one was synthesized by the same process as in Reference Example 7, (d) except for using monomethyl (1,1-dimethyl-3-phenylpropyl)propanedioate.

$^1$HNMR (CDCl$_3$) δ; 1.20 (3H, s), 1.28 (3H, s), 1.65 (1H, dd, J=11.2, 14.5 Hz), 1.87 (1H, dd, J=7.3, 14.5 Hz), 2.92 (1H, dd, J=7.3, 15.8 Hz), 3.13 (1H, dd, J=11.2, 15.8 Hz), 3.67 (3H, s), 3.94 (1H, s), 7.21~7.31 (2H, m), 7.39 (1H, td, J=1.7, 7.6 Hz), 7.74 (1H, dd, J=1.7, 7.6 Hz).

(e) Synthesis of Methyl 7,7-dimethyl-6,7-dihydro-5H-benzocycloheptene-8-carboxylate Methyl 7,7-dimethyl-6,7-dihydro-5H-benzocycloheptene-8-carboxylate was synthesized by the same process as in Reference Example 1, (b) and (c) except for using 7,7-dimethyl-6-methoxycarbonyl-6,7,8,9-tetrahydro-5H-benzocyclohepten-5-one.

$^1$HNMR (CDCl$_3$) δ; 1.36 (6H, s), 1.85 (2H, m), 2.87 (2H, m), 3.79 (3H, s), 7.10~7.25 (3H, m), 7.28~7.31 (1H, m), 7.33 (1H, s).

(f) Synthesis of 7,7-dimethyl-6,7-dihydro-5H-benzocycloheptene-8-carboxylic Acid 7,7-Dimethyl-6,7-dihydro-5H-benzocycloheptene-8-carboxylic acid was synthesized by carrying out reaction according to the method described in Reference Example 9, (d), except for using methyl 7,7-dimethyl-6,7-dihydro-5H-benzocycloheptene-8-carboxylate.

$^1$HNMR (CDCl$_3$) δ; 1.42 (6H, s), 1.88 (2H, m), 2.89 (2H, m), 7.13~7.23 (3H, m), 7.33~7.36 (1H, m), 7.66 (1H, s).

Reference Example 21
Synthesis of Methyl 7-ethyl-6,7-dihydro-5H-benzocycloheptene-8-carboxylate
(a) Synthesis of 7-ethyl-6,7,8,9-tetrahydro-5H-benzocyclohepten-5-one 7-Ethyl-6,7,8,9-tetrahydro-5H-benzocyclohepten-5-one was synthesized by the same process as in Reference Example 10, (a) and (b) and then the same process as in Reference Example 7, (c) and (d), except for using 1-phenylpentan-3-one as a starting material.

$^1$HNMR (CDCl$_3$) δ; 0.93 (3H, t, J=7.4 Hz), 1.50–1.74 (1H, m), 1.76–1.88 (1H, m), 1.96–2.07 (1H, m), 2.56–2.64 (1H, m), 2.77–2.93 (1H, m), 2.97–3.08 (1H, m), 7.18–7.22 (1H, m), 7.26–7.32 (1H, m), 7.38–7.43 (1H, m), 7.72–7.75 (1H, m).

(b) Synthesis of Methyl 7-ethyl-6,7-dihydro-5H-benzocycloheptene-8-carboxylate

Methyl 7-ethyl-6,7-dihydro-5H-benzocycloheptene-8-carboxylate was synthesized by the same process as in Reference Example 19, (b) and (c) except for using 7-ethyl-6,7,8,9-tetrahydro-5H-benzocyclohepten-5-one.

$^1$HNMR (CDCl$_3$) δ; 0.90 (3H, t, J=7.34 Hz), 1.27–1.39 (1H, m), 1.55–1.69 (1H, m), 1.87–2.09 (2H, m), 2.78–2.94 (2H, m), 2.95–3.08 (1H, m), 3.82 (3H, s), 7.08–7.35 (4H, m), 7.57 (1H, s).

Reference Example 22
Synthesis of Methyl 6-(2-propyl)-6,7-dihydro-5H-benzocycloheptene-8-carboxylate
(a) Synthesis of Ethyl 4-(2-propyl)-5-oxo-5-phenylpentanoate A mixture of isobutyl phenyl ketone (10.0 g, 61.6 mmol), 60% sodium hydride (5.42 g, 136 mmol) and N,N-dimethylformamide (100 ml) was stirred at 50° C. for 2.5 hours, and then the reaction mixture was cooled to 0° C. Ethyl δ-bromopropionate (12.3 g, 67.8 mmol) was added dropwise to the reaction mixture, and the resulting mixture was stirred at 0° C. for another 1 hour. The reaction mixture was adjusted to pH 1 by dropwise addition of 1N hydrochloric acid and extracted with a mixed solvent of ethyl acetate/toluene (2/1). The extract solution was washed with water and a saturated aqueous sodium chloride solution and dried over anhydrous magnesium sulfate. The solvent was distilled off under reduced pressure and the resulting residue was purified by a silica gel column chromatography to obtain 6.28 g of ethyl 4-(2-propyl)-5-oxo-5-phenylpentanoate.

$^1$HNMR (CDCl$_3$) δ; 0.90 (3H, d, J=6.9 Hz), 0.96 (3H, d, J=6.6 Hz), 1.19 (3H, t, J=7.3 Hz), 1.88~1.99 (1H, m), 2.02–2.19 (3H, m), 2.24–2.37 (1H, m), 3.37 (1H, ddd, J=3.6, 6.3, 9.9 Hz), 4.08 (2H, q, J=7.3 Hz), 7.46 (2H, dd, J=1.3, 7.6 Hz), 7.56 (1H, td, J=1.3, 7.6 Hz), 7.93 (2H, dd, J=1.3, 7.6 Hz).

(b) Synthesis of 4-(2-propyl)-5-oxo-5-phenylpentanoic Acid 5.87 Grams of 4-(2-propyl)-5-oxo-5-phenylpentanoic acid was obtained by carrying out reaction according to the method described in Reference Example 10, (c), except for using ethyl 4-(2-propyl)-5-oxo-5-phenylpentanoate (6.00 g, 22.9 mmol).

$^1$HNMR (CDCl$_3$) δ; 0.89 (3H, d, J=6.9 Hz), 0.97 (3H, d, J=6.6 Hz), 1.84~2.00 (1H, m), 2.03~2.22 (3H, m), 2.25~2.44 (1H, m), 3.37 (1H, ddd, J=3.6, 5.9, 9.9 Hz), 7.46 (2H, dd, J=1.3, 7.6 Hz), 7.57 (1H, td, J=1.3, 7.6 Hz), 7.92 (2H, dd, J=1.3, 7.6 Hz).

(c) Synthesis of 4-(2-propyl)-5-phenylpentanoic Acid 4-(2-Propyl)-5-oxo-5-phenylpentanoic acid (5.50 g, 23.5 mmol) was subjected to hydrogen catalytic reduction at room temperature by the use of 10% palladium-carbon (0.6 g) as catalyst in a mixed solvent of acetic acid (60 ml) and 35% hydrochloric acid (3 ml). The catalyst was filtered off and the filtrate was concentrated under reduced pressure to obtain 4.49 g of 4-(2-propyl)-5-phenylpentanoic acid.

$^1$HNMR (CDCl$_3$) δ; 0.87 (3H, d, J=6.9 Hz), 0.92 (3H, d, J=6.6 Hz), 1.46–1.59 (2H, m), 1.61–1.75 (2H, m), 2.27 (2H, dd, J=6.3, 7.6 Hz), 2.41 (1H, dd, J=7.6, 13.9 Hz), 2.63 (1H, dd, J=6.3, 13.9 Hz), 7.13–7.19 (3H, m), 7.22–7.29 (2H, m).

(d) Synthesis of 8-(2-propyl)-6,7,8,9-tetrahydro-5H-benzocyclohepten-5-one 2.61 Grams of 8-(2-propyl)-6,7,8,9-tetrahydro-5H-benzocyclohepten-5-one was obtained by the same process as in Reference Example 7, (d) except for using 4-(2-propyl)-5-phenylpentanoic acid (3.00 g, 13.6 mmol).

$^1$HNMR (CDCl$_3$) δ; 0.91 (3H, d, J=6.6 Hz), 1.00 (3H, d, J=6.6 Hz), 1.48–1.72 (3H, m), 1.85–1.97 (1H, m), 2.66 (1H, ddd, J=3.3, 8.3, 13.2 Hz), 2.81 (1H, ddd, J=3.6, 9.6, 13.2 Hz), 2.90 (2H, d, J=5.3 Hz), 7.20 (1H, dd, J=1.3, 7.6 Hz), 7.28 (1H, td, J=1.3, 7.6 Hz), 7.41 (1H, td, J=1.3, 7.6 Hz), 7.75 (1H, dd, J=1.3, 7.6 Hz).

(e) Synthesis of Methyl 6-(2-propyl)-6,7-dihydro-5H-benzocycloheptene-8-carboxylate Methyl 6-(2-propyl)-6,7-dihydro-5H-benzocycloheptene-8-carboxylate was synthesized by carrying out reaction according to the method described in Reference Example 1, except for using 8-(2-propyl)-6,7,8,9-tetrahydro-5H-benzocyclohepten-5-one.

$^1$HNMR (CDCl$_3$) δ; 0.96 (3H, d, J=6.6 Hz), 0.97 (3H, d, J=6.9 Hz), 1.69 (1H, m), 1.93 (1H, m), 2.35–2.52 (2H, m), 2.62 (1H, dd, J=7.9, 13.9 Hz), 2.71 (1H, dd, J=3.3, 13.9 Hz), 3.82 (3H, s), 7.15–7.29 (4H, m), 7.72 (1H, s).

Reference Example 23

Synthesis of Methyl 5,5-dimethyl-6 7-dihydro-5H-benzocycloheptene-8-carboxylate (a) Synthesis of 3,3-dimethyl-3-phenylpropionaldehyde A mixture of magnesium (4.48 g, 187 mmol), 1-chloro-2-methyl-2-phenylpropane (30.0 g, 179 mmol), a small amount of iodine and tetrahydrofuran (100 ml) was stirred at 70° C. for 2.5 hours. Then, the reaction mixture was cooled to 0° C., followed by adding dropwise thereto a solution of N-formylmorpholine (24.6 g, 214 mmol) in tetrahydrofuran (45 ml), and the resulting mixture was stirred at room temperature for 2 hours. Subsequently, the reaction mixture was re-cooled to 0° C. and 3N hydrochloric acid (180 ml) was added thereto, followed by stirring at room temperature. The reaction mixture was extracted with ethyl acetate, and the extract solution was washed successively with an aqueous sodium thiosulfate solution, an aqueous sodium hydrogencarbonate solution and a saturated aqueous sodium chloride solution, and then dried over anhydrous magnesium sulfate. The solvent was distilled off under reduced pressure and the resulting residue was purified by a silica gel column chromatography to obtain 18.0 g of 3,3-dimethyl-3-phenylpropionaldehyde.

$^1$HNMR (CDCl$_3$) δ; 1.46 (6H, s), 2.68 (2H, d, J=2.9 Hz), 7.20–7.28 (1H, m), 7.32–7.41 (4H, m), 9.50 (1H, t, J=3.0 Hz).

(b) Synthesis of Methyl 5,5-dimethyl-6,7-dihydro-5H-benzocycloheptene-8-carboxylate Methyl 5,5-dimethyl-6,7-dihydro-5H-benzocycloheptene-8-carboxylate was synthesized by carrying out reaction according to the method described in Reference Example 10, except for using 3,3-dimethyl-3-phenylpropionaldehyde.

$^1$HNMR (CDCl$_3$) δ; 1.31 (6H, s), 1.84 (2H, t, J=6.5 Hz), 2.75 (2H, dt, J=1.7, 6.5 Hz), 7.22 (1H, dt, J=1.7, 7.3 Hz), 7.28 (1H, dt, J=1.7, 6.7 Hz), 7.38 (1H, dd, J=1.8, 7.3 Hz), 7.43 (1H, dd, J=1.5, 7.7 Hz).

Reference Example 24

Synthesis of Methyl 6-ethyl-6,7-dihydro-5H-benzocycloheptene-8-carboxylate (a) Synthesis of 8-ethyl-6,7,8,9-tetrahydro-5H-benzocyclohepten-5-one 8-Ethyl-6,7,8,9-tetrahydro-5H-benzocyclohepten-5-one was synthesized by carrying out reactions according to the methods described in Reference Example 22, (a) to (c) and then the method described in Reference Example 18, (c), except for using n-butyrophenone as a starting material.

$^1$HNMR (CDCl$_3$) δ; 0.97 (3H, t, J=7.5 Hz), 1.28–1.45 (3H, m), 1.79–2.00 (2H, m), 2.58–2.83 (3H, m), 2.97 (1H, dd, J=5.0, 14.4 Hz), 7.17 (1H, dd, J=1.4, 7.4 Hz), 7.30 (1H, td, J=1.4, 7.4 Hz), 7.42 (1H, td, J=1.4, 7.4 Hz), 7.72 (1H, dd, J=1.4, 7.4 Hz).

(b) Synthesis of Methyl 6-ethyl-6,7-dihydro-5H-benzocycloheptene-8-carboxylate

Methyl 6-ethyl-6,7-dihydro-5H-benzocycloheptene-8-carboxylate was synthesized by carrying out reaction according to the method described in Reference Example 1, except for using 8-ethyl-6,7,8,9-tetrahydro-5H-benzocyclohepten-5-one.

$^1$HNMR (CDCl$_3$) δ; 0.97 (3H, t, J=7.3 Hz), 1.40 (2H, q, J=7.3 Hz), 2.05–2.18 (1H, m), 2.23 (1H, ddd, J=1.3, 8.3, 15.8 Hz), 2.52 (1H, dd, J=7.3, 13.9 Hz), 2.58 (1H, dd, J=5.4, 15.8 Hz), 2.74 (1H, dd, J=4.0, 13.9 Hz), 3.82 (3H, s), 7.15–7.30 (4H, m), 7.74 (1H, s).

Reference Example 25

Synthesis of Methyl 6, 6-dimethyl-6,7-dihydro-5H-benzocycloheptene-8-carboxylate Methyl 6,6-dimethyl-6,7-dihydro-5H-benzocycloheptene-8-carboxylate was synthesized by the same process as in Reference Example 24 except for using isobutyrophenone as a starting material.

$^1$HNMR (CDCl$_3$) δ; 1.04 (6H, s), 2.10 (2H, s), 2.38 (2H, s), 3.83 (3H, s), 7.17–7.28 (4H, m), 7.79 (1H, s).

Reference Example 26

Synthesis of 7-(2-propyl)-6,7-dihydro-5H-benzocycloheptene-8-carboxylic Acid (a) Synthesis of 4-methyl-1-phenylpentan-3-one A mixture of 3-phenylpropionic acid (13.0 g, 86.6 mmol), 2,3-dihydrofuran (6.67 g, 95.2 mmol) and dichloromethane (90 ml) was cooled to −60° C., followed by adding thereto a solution of methanesulfonic acid (0.012 g, 0.13 mmol) in dichloromethane (1 ml). The reaction mixture was heated to −5° C. and stirred at this temperature for 4 hours. The reaction mixture was re-cooled to −60° C., followed by adding dropwise thereto isopropylmagnesium chloride (a 2M tetrahydrofuran solution; 48 ml, 95.2 mmol), and the resulting mixture was stirred at room temperature for 16 hours. The reaction mixture was poured into a cooled aqueous phosphoric acid solution and extracted with chloroform. The extract solution was washed successively with water, a saturated aqueous sodium hydrogencarbonate solution, water and a saturated aqueous sodium chloride solution, and then dried over anhydrous magnesium sulfate. The solvent was distilled off under reduced pressure and the resulting residue was purified by a silica gel column chromatography to obtain 5.97 g of 4-methyl-1-phenylpentan-3-one.

$^1$HNMR (CDCl$_3$) δ; 1.07 (6H, d, J=6.9 Hz), 2.56 (1H, m), 2.76 (2H, m), 2.89 (2H, m), 7.15–7.20 (3H, m), 7.27 (2H, m).

(b) Synthesis of Ethyl 3-(2-propyl)-5-phenylpentanoate

Ethyl 3-(2-propyl)-5-phenylpentanoate was synthesized by the same process as in Reference Example 10, (a) and (b) except for using 4-methyl-1-phenylpentan-3-one.

$^1$HNMR (CDCl$_3$) δ; 0.87 (6H, m), 1.25 (3H, t, J=7.3 Hz), 1.48–1.68 (2H, m), 1.69–1.89 (2H, m), 2.21 (1H, dd, J=7.6, 15.2 Hz), 2.34 (1H, dd, J=5.9, 15.2 Hz), 2.60 (2H, m), 4.12 (2H, q, J=7.3 Hz), 7.14–7.30 (5H, m).

(c) Synthesis of Monoethyl[3-phenyl-1-(2-propyl)propyl]propanedioate

A solution of ethyl 3-(2-propyl)-5-phenylpentanoate (2.30 g, 9.26 mmol) in tetrahydrofuran (25 ml) was cooled to −78° C., followed by adding dropwise thereto lithium diisopropylamide (a 2M solution in a mixed solvent of heptane, tetrahydrofuran and ethylbenzene; 5.6 ml, 11.1 mmol). Then, carbon dioxide was introduced into the reaction mixture at −78° C. for 10 minutes. The reaction mixture was adjusted to pH 2 by dropwise addition of water and 1N hydrochloric acid and extracted with ethyl acetate. The extract solution was washed with water and a saturated aqueous sodium chloride solution and dried over anhydrous magnesium sulfate. The solvent was distilled off under reduced pressure to obtain 2.45 g of monoethyl [3-phenyl-1-(2-propyl)propyl]propanedioate.

$^1$HNMR (DMSO-d$_6$) δ; 0.92 (6H, m), 1.28 (3H, m), 1.64–1.77 (2H, m), 1.84 (1H, m), 2.17 (1H, m), 2.52–2.69 (2H, m), 3.53 (1H, d, J=6.9 Hz), 4.08–4.26 (2H, m), 7.14–7.29 (5H, m).

(d) Synthesis of 7-(2-propyl)-6,7-dihydro-5H-benzocycloheptene-8-carboxylic Acid 7-(2-Propyl)-6,7-dihydro-5H-benzocycloheptene-8-carboxylic acid was synthesized by the same process as in Reference Example 7, (d), the same process as in Reference Example 1, (b) and (c), and then the same process as in Reference Example 22, (b), except for using monoethyl[3-phenyl-1-(2-propyl)propyl]propanedioate.

$^1$HNMR (CDCl$_3$) δ; 0.79 (3H, d, J=6.6 Hz), 0.91 (3H, d, J=6.6 Hz), 1.98 (1H, m), 2.01–2.10 (2H, m), 2.82–2.94 (2H, m), 3.06 (1H, m), 7.14–7.32 (3H, m), 7.33 (1H, m), 7.8 (1H, s).

Reference Example 27

Synthesis of 4-chloro-7-methyl-6,7-dihydro-5H-benzocycloheptene-8-carboxylic Acid (a) Synthesis of 1-(2-chlorophenyl)-1-buten-3-one A mixture of 2-chlorobenzaldehyde (25.0 g, 178 mmol), acetone (40 ml) and water (20 ml) was cooled to 0° C., followed by adding dropwise thereto a 5% aqueous sodium hydroxide solution (7 ml), and the resulting mixture was stirred at room temperature for 4 hours. The reaction mixture was adjusted to pH 1 with 1N hydrochloric acid and extracted with ethyl acetate. The extract solution was washed with water and a saturated aqueous sodium chloride solution and dried over anhydrous magnesium sulfate. The solvent was distilled off under reduced pressure and the resulting residue was purified by a silica gel column chromatography to obtain 13.2 g of 1-(2-chlorophenyl)-1-buten-3-one.

$^1$HNMR (CDCl$_3$) δ; 2.70 (3H, s), 6.95 (1H, d, J=16.2 Hz), 7.54~7.64 (2H, m), 7.70 (1H, m), 7.91 (1H, dd, J=2.0, 6.9 Hz), 8.21 (1H, d, J=16.2 Hz).

(b) Synthesis of Ethyl 5-(2-chlorophenyl)-3-methylpentanoate

Ethyl 5-(2-chlorophenyl)-3-methylpentanoate was synthesized by carrying out reactions according to the methods described in Reference Example 10, (a) and (b), except for using 1-(2-chlorophenyl)-1-buten-3-one and using platinum oxide (PtO$_2$) as a catalyst for hydrogen catalytic reduction in place of 10% palladium-carbon.

$^1$HNMR (CDCl$_3$) δ; 1.04 (3H, d, J=6.6 Hz), 1.26 (3H, t, J=7.3 Hz), 1.43~1.72 (2H, m), 2.05 (1H, m), 2.18 (1H, dd, J=7.9, 14.5 Hz), 2.37 (1H, dd, J=5.9, 14.5 Hz), 2.64~2.84 (2H, m), 4.14 (2H, q, J=7.3 Hz), 7.08~7.24 (3H, m), 7.32 (1H, dd, J=1.7, 7.6 Hz).

(c) Synthesis of Ethyl 4-chloro-7-methyl-6,7-dihydro-5H-benzocycloheptene-8-carboxylate Ethyl 4-chloro-7-methyl-6,7-dihydro-5H-benzocycloheptene-8-carboxylate was synthesized by carrying out reactions according to the methods described in Reference Example 26, (c), Reference Example 18, (c) and Reference Example 1, (b) and (c), except for using ethyl 5-(2-chlorophenyl)-3-methylpentanoate.

$^1$HNMR (CDCl$_3$) δ; 1.11 (3H, d, J=6.9 Hz), 1.36 (3H, t, J=7.3 Hz), 1.83~2.07 (2H, m), 3.01~3.16 (2H, m), 3.17~3.28 (1H, m), 4.27 (2H, m), 7.12 (1H, t, J=7.6 Hz), 7.24 (1H, d, J=7.6 Hz), 7.31 (1H, dd, J=1.3, 7.6 Hz), 7.51 (1H, s).

(d) Synthesis of 4-chloro-7-methyl-6,7-dihydro-5H-benzocycloheptene-8-carboxylic Acid 4-Chloro-7-methyl-6,7-dihydro-5H-benzocycloheptene-8-carboxylic acid was synthesized by the same process as in Reference Example 10, (c) except for using ethyl 4-chloro-7-methyl-6,7-dihydro-5H-benzocycloheptene-8-carboxylate.

$^1$HNMR (CDCl$_3$) δ; 1.17 (3H, d, J=6.9 Hz), 1.89~2.08 (2H, m), 2.98~3.16 (2H, m), 3.18~3.28 (1H, m), 7.15 (1H, t, J=7.9 Hz), 7.27 (1H, d, J=7.9 Hz), 7.35 (1H, dd, J=1.7, 7.9 Hz), 7.74 (1H, s).

Reference Example 28

Synthesis of 1,7-dimethyl-6,7-dihydro-5H-benzocycloheptene-8-carboxylic Acid (a) Synthesis of 4,7-diemthyl-6,7,8,9-tetrahydro-5H-benzocyclohepten-5-one A mixture of the 7-methyl-6,7,8,9-tetrahydro-5H-benzocyclohepten-5-one (6.63 g, 38.1 mmol) synthesized in Reference Example 10, (d), trimethylsilane chloride (7.25 ml, 57.1 mmol), sodium iodide (8.56 g, 57.1 mmol), triethylamine (7.95 ml, 57.0 mmol) and acetonitrile (80 ml) was stirred at room temperature for 4 hours. Then, the solvent was distilled off under reduced pressure and the resulting residue was extracted with a mixed solvent of n-hexane/diethyl ether (1/1). The extract solution was concentrated under reduced pressure and the resulting residue was dissolved in n-hexane (150 ml), followed by adding thereto tetramethylethylenediamine (13.5 ml, 89.4 mmol), and the reaction mixture was cooled to 0° C. Then, n-butyllithium (a 3.0 M n-hexane solution; 30 ml, 90.6 mmol) was added dropwise to the reaction mixture and the resulting mixture was stirred at room temperature for 20 minutes and then at 60° C. for 2.5 hours. The reaction mixture was cooled to room temperature and methyl iodide (3.55 ml, 57.0 mmol) was added thereto, followed by stirring at room temperature for 30 minutes. The reaction mixture was diluted with n-hexane and the dilution was washed with water and dried over anhydrous magnesium sulfate. The solvent was distilled off under reduced pressure and the resulting residue was purified by a silica gel column chromatography to obtain 3.43 g of 4,7-dimethyl-6,7,8,9-tetrahydro-5H-benzocyclohepten-5-one.

$^1$HNMR (CDCl$_3$) δ; 1.02 (3H, d, J=6.5 Hz), 1.41~1.50 (1H, m), 1.86~2.07 (2H, m), 2.30 (3H, s), 2.45 (1H, dd, J=11.1, 15.4 Hz), 2.60 (1H, ddd, J=1.0, 3.5, 15.4 Hz), 2.73~2.81 (2H, m), 6.96 (1H, d, J=7.5 Hz), 7.07 (1H, d, J=7.5 Hz), 7.20 (1H, t, J=7.5 Hz).

(b) Synthesis of 6-[bis(methylthio)methylene]-4,7-dimethyl-6,7,8,9-tetrahydro-5H-benzocyclohepten-5-one 6-[Bis(methylthio)methylene]-4,7-diemthyl-6,7,8,9-tetrahydro-5H-benzocyclohepten-5-one was synthesized by the same process as in Reference Example 9, (b) except for using 4,7-diemthyl-6,7,8,9-tetrahydro-5H-benzocyclohepten-5-one.

$^1$HNMR (CDCl$_3$) δ; 1.17 (3H, d, J=6.7 Hz), 1.40~1.57 (1H, m), 2.02 (3H, s), 2.08~2.20 (1H, m), 2.27 (3H, s), 2.59 (3H, s), 2.79 (1H, dd, J=11.5, 17.2 Hz), 2.97 (1H, dd, J=6.7, 17.2 Hz), 3.24~3.39 (1H, m), 6.99 (1H, d, J=7.3 Hz), 7.10 (1H, d, J=7.3 Hz), 7.19 (1H, t, J=7.3 Hz).

(c) Synthesis of Methyl 1,7-dimethyl-6,7-dihydro-5H-benzocycloheptene-8-carboxylate A solution of lithium aluminum hydride (0.027 g, 0.71 mmol) in tetrahydrofuran (2 ml) was cooled to 0° C., and a solution of 6-[bis(methylthio)methylene]-4,7-dimethyl-6,7,8,9-tetrahydro-5H-benzocyclohepten-5-one (0.15 g, 0.50 mmol) in tetrahydrofuran (1 ml) was added dropwise to the cooled solution and stirred for 1 hour. Aqueous tetrahydrofuran was added dropwise to the reaction solution, followed by extraction with ethyl acetate. The extract solution was washed with a saturated aqueous sodium chloride solution and dried over anhydrous sodium sulfate. The solvent was distilled off under reduced pressure and trifluoroborondiethyl ether complex (0.3 ml) was added to the residue and stirred for 10 minutes. Then, methanol (2.5 ml) was added thereto and the resulting mixture was heated under reflux for 9 hours. The reaction mixture was poured into ice water and extracted with ethyl acetate, and the extract solution was dried over anhydrous magnesium sulfate. The solvent was distilled off under reduced pressure and the resulting residue was purified by a silica gel column chromatography to obtain 0.08 g of methyl 1,7-dimethyl-6,7-dihydro-5H-benzocycloheptene-8-carboxylate.

$^1$HNMR (CDCl$_3$) δ; 1.03 (3H, d, J=7.0 Hz), 1.73~1.87 (1H, m), 2.17~2.30 (1H, m), 2.39 (3H, s), 2.66~2.72 (2H, m), 3.13 (1H, qt, J=7.0, 7.0 Hz), 3.83 (3H, s), 6.96~7.14 (3H, m), 7.75 (1H, s).

(d) Synthesis of 1,7-dimethyl-6,7-dihydro-5H-benzocycloheptene-8-carboxylic Acid 1,7-Dimethyl-6,7-dihydro-5H-benzocycloheptene-8-carboxylic acid was synthesized by the same process as in Reference Example 10, (c) except for using methyl 1,7-dimethyl-6,7-dihydro-5H-benzocycloheptene-8-carboxylate.

$^1$HNMR (CDCl$_3$) δ; 1.09 (3H, d, J=7.0 Hz), 1.74~1.88 (1H, m), 2.15~2.31 (1H, m), 2.41 (3H, s), 2.70~2.75 (2H, m), 3.15 (1H, qt, J=7.0, 7.0 Hz), 7.00 (1H, d, J=7.3 Hz), 7.07 (1H, d, J=7.3 Hz), 7.13 (1H, t, J=7.3 Hz), 7.96 (1H, s).

Reference Example 29

Synthesis of 4,7-dimethyl-6,7-dihydro-5H-benzocycloheptene-8-carboxylic Acid 4,7-Dimethyl-6,7-dihydro-5H-benzocycloheptene-8-carboxylic acid was synthesized by carrying out reaction according to the method described in Reference Example 27, except for using 2-methylbenzaldehyde as a starting material and 10% palladium-carbon as a catalyst for hydrogen catalytic reduction.

$^1$HNMR (CDCl$_3$) δ; 1.12 (3H, d, J=6.8 Hz), 1.86~2.15 (2H, m), 2.36 (3H, s), 2.88 (2H, t, J=5.7 Hz), 3.18~3.26 (1H, m), 7.09~7.20 (2H, m), 7.24 (1H, dd, J=2.3, 6.9 Hz), 7.74 (1H, s).

Reference Example 30

Synthesis of 3-chloro-7-methyl-6,7-dihydro-5H-benzocycloheptene-8-carboxylic Acid (a) Synthesis of 1-(3-chlorophenyl)-1-buten-3-one 1-(3-Chlorophenyl)-1-buten-3-one was synthesized by the same process as in Reference Example 27, (a) except for using 3-chlorobenzaldehyde.

$^1$HNMR (CDCl$_3$) δ; 2.38 (3H, s), 6.70 (1H, d, J=16.2 Hz), 7.30~7.43 (3H, m), 7.44 (1H, d, J=16.2 Hz), 7.52 (1H, d, J=1.9 Hz).

(b) Synthesis of 1-(3-chlorophenyl)butan-3-one 1-(3-Chlorophenyl)-1-buten-3-one (20.0 g, 111 mmol) was subjected to hydrogen catalytic reduction in ethanol (200 ml) at room temperature by using platinum oxide (PtO$_2$; 0.30 g) as a catalyst. The catalyst was filtered off and the resulting filtrate was concentrated under reduced pressure. The resulting residue was purified by a silica gel column chromatography to obtain 11.1 g of 1-(3-chlorophenyl)butan-3-one.

$^1$HNMR (CDCl$_3$) δ; 2.14 (3H, s), 2.72~2.78 (2H, m), 2.84~2.90 (2H, m), 7.06 (1H, ddd, J=1.7, 2.0, 6.6 Hz), 7.14~7.24 (3H, m).

(c) Synthesis of Monoethyl[1-methyl-3-(3-chlorophenyl)propyl]propanedioate

Monoethyl[1-methyl-3-(3-chlorophenyl)propyl]-propanedioate was synthesized by carrying out reactions according to the methods described in Reference Example 10 (a) and (b) and Reference Example 26 (c), except for using 1-(3-chlorophenyl)butan-3-one and platinum oxide (PtO$_2$) as a catalyst for hydrogen catalytic reduction.

$^1$HNMR (CDCl$_3$) δ; 1.10 (3H, m), 1.28 (3H, m), 1.46~1.64 (1H, m), 1.74~1.86 (1H, m), 2.24–2.35 (1H, m), 2.51~2.75 (2H, m), 3.36 (1H, m), 4.23 (2H, m), 7.04 (1H, m), 7.14~7.30 (3H, m), 8.3~9.7 (1H, m).

(c) Synthesis of 3-chloro-7-methyl-6,7-dihydro-5H-benzocycloheptene-8-carboxylic Acid 3-Chloro-7-methyl-6,7-dihydro-5H-benzocycloheptene-8-carboxylic acid was synthesized by carrying out reactions according to the methods described in Reference Example 18, (c), Reference Example 1, (b) and (c) and Reference Example 10, (c), except for using monoethyl[1-methyl-3-(3-chlorophenyl)propyl]propanedioate.

$^1$HNMR (CDCl$_3$) δ; 1.20 (3H, d, J=6.9 Hz), 1.91~2.05 (2H, m), 2.78~2.86 (1H, m), 2.93~3.03 (1H, m), 3.21~3.28 (1H, m), 7.18 (1H, s), 7.20 (1H, dd, J=1.9, 8.9 Hz), 7.28 (1H, d, J=8.9 Hz), 7.67 (1H, s).

Reference Example 31

Synthesis of 3,7-dimethyl-6,7-dihydro-5H-benzocycloheptene-8-carboxylic Acid 3,7-Dimethyl-6,7-dihydro-5H-benzocycloheptene-8-carboxylic acid was synthesized by carrying out reaction according to the method described in Reference Example 30, except for using 3-methylbenzaldehyde as a starting material and using 10% palladium-carbon as a catalyst for hydrogen catalytic reduction in place of platinum oxide (PtO$_2$).

$^1$HNMR (CDCl$_3$) δ; 1.20 (3H, d, J=6.8 Hz), 1.93 (2H, q, J=5.4 Hz), 2.34 (3H, s), 2.73~2.86 (1H, m), 2.95~3.05 (1H, m), 3.16~3.29 (1H, m), 7.01~7.05 (2H, m), 7.27 (1H, d, J=7.7 Hz), 7.72 (1H, s).

Reference Example 32

Synthesis of 2,7-dimethyl-6,7-dihydro-5H-benzocycloheptene-8-carboxylic Acid (a) Synthesis of 1-(4-methylphenyl)butan-3-one 1-(4-Methylphenyl)butan-3-one was synthesized by carrying out reactions according to the methods described in Reference Example 27, (a) and Reference Example 30, (b), except for using 4-methylbenzaldehyde as a starting material and 10% palladium-carbon as a catalyst for hydrogen catalytic reduction.

$^1$HNMR (CDCl$_3$) δ; 2.13 (3H, s), 2.31 (3H, s), 2.70~2.77 (2H, m), 2.82~2.90 (2H, m), 7.04~7.13 (4H, m).

(b) Synthesis of 1-(4-methylphenyl)butan-3-ol

A solution of 1-(4-methylphenyl)butan-3-one (11.4 g, 70.3 mmol) in methanol (80 ml) was cooled, followed by adding thereto sodium tetrahydroborate (1.51 g, 40.0 mmol), and the resulting mixture was stirred at 0° C. for 2 hours. The reaction mixture was added to 1N hydrochloric acid, and the methanol was distilled off under reduced pressure and the residue was extracted with ethyl acetate. The extract solution was washed with a saturated aqueous sodium chloride solution and dried over anhydrous magnesium sulfate, and then the solvent was distilled off under reduced pressure to obtain 11.7 g of 1-(4-methylphenyl)butan-3-ol.

$^1$HNMR (CDCl$_3$) δ; 1.22 (3H, d, J=6.1 Hz), 1.70~1.80 (2H, m), 2.32 (3H, s), 2.55~2.78 (2H, m), 3.71~3.89 (1H, m), 7.10 (4H, brs).

(c) Synthesis of Monoethyl[1-methyl-3-(4-methylphenyl)propyl]propanedioate

Triethylamine (19.5 g, 140 mmol) was added to a solution of 1-(4-methylphenyl)butan-3-ol (11.7 g, 71.1 mmol) in toluene (100 ml), and the resulting mixture was cooled to 0° C. Then, methanesulfonyl chloride (6.58 ml, 85.0 mmol) was added dropwise thereto, followed by stirring at 0° C. for 1 hour and then at room temperature for 1 hour. The reaction mixture was poured into a saturated aqueous sodium hydrogen-carbonate solution and extracted with ethyl acetate, and the extract solution was washed with a saturated aqueous sodium chloride solution. Then, the extract solution was dried over anhydrous magnesium sulfate, and the solvent was distilled off under reduced pressure. The resulting residue (18.2 g) was added to a mixture of benzylmethyl malonate (19.3 ml, 107 mmol), 60% sodium hydride (4.56 g, 114 mmol) and N-methyl-2-pyrrolidinone (100 ml), and the resulting mixture was stirred at 80° C. for 5 hours. The reaction mixture was added to 1N hydrochloric acid and extracted with a mixed solvent of toluene/ethyl acetate (1/1), and the extract solution was washed with 1N hydrochloric acid and a saturated aqueous sodium chloride solution and then dried over anhydrous magnesium sulfate. The solvent was distilled off and the resulting residue was purified by a silica gel column chromatography to obtain 14.2 g of benzylethyl [1-methyl-3-(4-methylphenyl)propyl]propanedioate. Then, this ester (14.2 g) was subjected to hydrogen catalytic reduction in ethyl acetate (100 ml) at room temperature by using 10% palladium-carbon (1.4 g) as a catalyst. The catalyst was filtered off and the filtrate was concentrated under reduced pressure to obtain 10.5 g of monoethyl[1-methyl-3-(4-methylphenyl)propyl]propanedioate.

$^1$HNMR (CDCl$_3$) δ; 1.09 (3H, m), 1.47–1.63 (1H, m), 1.72–1.85 (1H, m), 2.31 (3H, s), 2.24–2.36 (1H, m), 2.49–2.75 (2H, m), 3.39 (1H, m), 3.76 (3H, s), 7.03–7.12 (4H, m).

(d) Synthesis of 2,7-dimethyl-6,7-dihydro-5H-benzocycloheptene-8-carboxylic Acid 2,7-Dimethyl-6,7-dihydro-5H-benzocycloheptene-8-carboxylic acid was synthesized by carrying out reactions according to the methods described in Reference Example 18 (c), Reference Example 1 (b) and (c) and Reference Example 10 (c), except for using monoethyl[1-methyl-3-(4-methylphenyl)propyl]propanedioate.

$^1$HNMR (CDCl$_3$) δ; 1.19 (3H, d, J=6.5 Hz), 1.88–1.97 (2H, m), 2.33 (3H, s), 2.82 (1H, ddd, J=3.3, 6.1, 15.7 Hz), 2.98 (1H, ddd, J=3.8, 8.3, 15.7 Hz), 3.24 (1H, qt, J=6.5, 6.5 Hz), 7.03–7.10 (2H, m), 7.19 (1H, s), 7.69 (1H, s).

Example 16

Synthesis of N-(aminoiminomethyl)-1-methyl-2,3-dihydro-1H-benz[b]azepine-4-carboxamide Dimethanesulfonate 0.43 Gram of N-(aminoiminomethyl)-1-methyl-2,3-dihydro-1H-benz[b]azepine-4-carboxamide dimethanesulfonate was obtained by the same process as in Example 3 except for using ethyl 1-methyl-2,3-dihydro-1H-benz[b]azepine-4-carboxylate (0.40 g, 1.73 mmol), sodium methoxide (0.47 g), guanidine hydrochloride (0.83 g) and N,N-dimethylformamide (16 ml).

Melting point: 175–176° C.

Example 17

Synthesis of N-(aminoiminomethyl)-5-(2-propyl)-6,7-dihydro-5H-benzocycloheptene-8-carboxamide Methanesulfonate 2.2 Grams of N-(aminoiminomethyl)-5-(2-propyl)-6,7-dihydro-5H-benzocycloheptene-8-carboxamide methanesulfonate was obtained by the same process as in Example 1 except for using methyl 5-(2-propyl)-6,7-dihydro-5H-benzocycloheptene-8-carboxylate (1.97 g, 8.05 mmol), sodium methoxide (4.31 g), guanidine hydrochloride (7.65 g) and N,N-dimethylformamide (50 ml).

Melting point: 176° C.

Example 18

Synthesis of N-(aminoiminomethyl)-5-ethyl-6,7-dihydro-5H-benzocycloheptene-8-carboxamide Methanesulfonate 0.19 Gram of N-(aminoiminomethyl)-5-ethyl-6,7-dihydro-5H-benzocycloheptene-8-carboxamide methanesulfonate was obtained by the same process as in Example 1 except for using methyl 5-ethyl-6,7-dihydro-5H-benzocycloheptene-8-carboxylate (0.20 g, 1.87 mmol), sodium methoxide (0.94 g), guanidine hydrochloride (1.66 g) and N,N-dimethylformamide (15 ml).

Melting point: 152–153° C.

Example 19

Synthesis of N-(aminoiminomethyl)-7,7-dimethyl-6,7-dihydro-5H-benzocycloheptene-8-carboxamide Methanesulfonate 0.41 Gram of N-(aminoiminomethyl)-7,7-dimethyl-6,7-dihydro-5H-benzocycloheptene-8-carboxamide methanesulfonate was obtained by carrying out reaction according to the method described in Example 8, except for using 7,7-dimethyl-6,7-dihydro-5H-benzocycloheptene-8-carboxylic acid (0.80 g, 3.70 mmol), N,N'-carbonyldiimidazole (0.90 g, 5.55 mmol), guanidine hydrochloride (3.53 g, 37.0 mmol), sodium methoxide (2.00 g, 37.0 mmol) and N,N-dimethylformamide (33 ml).

Melting point: 139–140° C.

Example 20
Synthesis of N-(aminoiminomethyl)-7-ethyl-6,7-dihydro-5H-benzocycloheptene-8-carboxamide Methanesulfonate 1.27 Grams of N-(aminoiminomethyl)-7-ethyl-6,7-dihydro-5H-benzocycloheptene-8-carboxamide methanesulfonate was obtained by the same process as in Example 1 except for using methyl 7-ethyl-6,7-dihydro-5H-benzocycloheptene-8-carboxylate (1.40 g, 6.08 mmol), guanidine hydrochloride (11.6 g, 21.6 mmol), sodium methoxide (6.57 g, 21.6 mmol) and N,N-dimethylformamide (22 ml).

Melting point: 120–122° C.

Example 21
Synthesis of N-(aminoiminomethyl)-6-(2-propyl)-6,7-dihydro-5H-benzocycloheptene-8-carboxamide Methanesulfonate 1.02 Grams of N-(aminoiminomethyl)-6-(2-propyl)-6,7-dihydro-5H-benzocycloheptene-8-carboxamide methanesulfonate was obtained by the same process as in Example 1 except for using methyl 6-(2-propyl)-6,7-dihydro-5H-benzocycloheptene-8-carboxylate (1.00 g, 4.09 mmol), guanidine hydrochloride (3.91 g, 40.9 mmol), sodium methoxide (2.21 g, 40.9 mmol) and N,N-dimethylformamide (15 ml).

Melting point: 149–150° C.

Example 22
Synthesis of N-(aminoiminomethyl)-5,5-dimethyl-6,7-dihydro-5H-benzocycloheptene-8-carboxamide Methanesulfonate 2.50 Grams of N-(aminoiminomethyl)-5,5-dimethyl-6,7-dihydro-5H-benzocycloheptene-8-carboxamide methanesulfonate was obtained by the same process as in Example 1 except for using methyl 5.5-dimethyl-6,7-dihydro-5H-benzocycloheptene-8-carboxylate (2.00 g, 8.69 mmol), guanidine hydrochloride (16.6 g, 174 mmol), sodium methoxide (9.38 g, 174 mmol) and N,N-dimethylformamide (50 ml).

Melting point: 185–187° C.

Example 23
Synthesis of N-(aminoiminomethyl)-6-ethyl-6,7-dihydro-5H-benzocycloheptene-8-carboxamide Methanesulfonate 3.09 Grams of N-(aminoiminomethyl)-6-ethyl-6,7-dihydro-5H-benzocycloheptene-8-carboxamide methanesulfonate was obtained by the same process as in Example 1 except for using methyl 6-ethyl-6,7-dihydro-5H-benzocycloheptene-8-carboxylate (2.44 g, 10.6 mmol), guanidine hydrochloride (9.56 g, 100 mmol), sodium methoxide (5.40 g, 100 mmol) and N,N-dimethylformamide (60 ml).

Melting point: 166.5–167° C.

Example 24
Synthesis of N-(aminoiminomethyl)-6,6-dimethyl-6,7-dihydro-5H-benzocycloheptene-8-carboxamide Methanesulfonate 1.70 Grams of N-(aminoiminomethyl)-6,6-dimethyl-6,7-dihydro-5H-benzocycloheptene-8-carboxamide methanesulfonate was obtained by the same process as in Example 1 except for using methyl 6,6-dimethyl-6,7-dihydro-5H-benzocycloheptene-8-carboxylate (1.61 g, 6.98 mmol), guanidine hydrochloride (6.70 g, 70.1 mmol), sodium methoxide (3.79 g, 70.1 mmol) and N,N-dimethylformamide (40 ml).

Melting point: 175° C.

Example 25
Synthesis of N-(aminoiminomethyl)-7-(2-propyl)-6,7-dihydro-5H-benzocycloheptene-8-carboxamide Methanesulfonate 0.20 Gram of N-(aminoiminomethyl)-7-(2-propyl)-6,7-dihydro-5H-benzocycloheptene-8-carboxamide methanesulfonate was obtained by carrying out reaction according to the method described in Example 8, except for using 7-(2-propyl)-6,7-dihydro-5H-benzocycloheptene-8-carboxylic acid (0.18 g, 0.80 mmol), N,N'-carbonyldiimidazole (0.19 g, 1.20 mmol), guanidine hydrochloride (0.76 g, 7.99 mmol), sodium methoxide (0.43 g, 7.99 mmol) and N,N-dimethylformamide (2 ml).

Melting point: 166.5–168° C.

Example 26
Synthesis of N-(aminoiminomethyl)-4-chloro-7-methyl-6,7-dihydro-5H-benzocycloheptene-8-carboxamide Methanesulfonate 2.09 Grams of N-(aminoiminomethyl)-4-chloro-7-methyl-6,7-dihydro-5H-benzocycloheptene-8-carboxamide methanesulfonate was obtained by carrying out reaction according to the method described in Example 8, except for using 4-chloro-7-methyl-6,7-dihydro-5H-benzocycloheptene-8-carboxylic acid (1.50 g, 6.34 mmol), N,N'-carbonyldiimidazole (1.54 g, 9.51 mmol), guanidine hydrochloride (6.05 g, 63.4 mmol), sodium methoxide (3.42 g, 63.4 mmol) and N,N-dimethylformamide (25 ml).

Melting point: 177.5–180° C.

Example 27
Synthesis of N-(aminoiminomethyl)-1,7-dimethyl-6,7-dihydro-5H-benzocycloheptene-8-carboxamide Methanesulfonate 0.90 Gram of N-(aminoiminomethyl)-1,7-dimethyl-6,7-dihydro-5H-benzocycloheptene-8-carboxamide methanesulfonate was obtained by carrying out reaction according to the method described in Example 8, except for using 1,7-dimethyl-6,7-dihydro-5H-benzocycloheptene-8-carboxylic acid (0.91 g, 4.07 mmol), N,N'-carbonyldiimidazole (0.99 g, 6.11 mmol), guanidine hydrochloride (3.82 g, 39.9 mmol), sodium methoxide (2.16 g, 40.0 mmol) and N,N-dimethylformamide (30 ml).

Melting point: 137.5–139° C.

Example 28
Synthesis of N-(aminoiminomethyl)-4,7-dimethyl-6,7-dihydro-5H-benzocycloheptene-8-carboxamide Methanesulfonate 0.74 Gram of N-(aminoiminomethyl)-4,7-dimethyl- 6,7-dihydro-5H-benzocycloheptene-8-carboxamide methanesulfonate was obtained by carrying out reaction according to the method described in Example 8, except for using 4,7-dimethyl-6,7-dihydro-5H-benzocycloheptene-8-carboxylic acid (0.80 g, 3.70 mmol), N,N'-carbonyldiimidazole (0.90 g, 5.55 mmol), guanidine hydrochloride (8.39 g, 87.9 mmol), sodium methoxide (4.75 g, 87.9 mmol) and N,N-dimethylformamide (49.5 ml).

Melting point: 150–152° C.

Example 29
Synthesis of N-(aminoiminomethyl)-3-chloro-7-methyl-6,7-dihydro-5H-benzocycloheptene-8-carboxamide Methanesulfonate 2.11 Grams of N-(aminoiminomethyl)-3-chloro-7-methyl-6,7-dihydro-5H-benzocycloheptene-8-carboxamide methanesulfonate was obtained by carrying out reaction according to the method described in Example 8, except for using 3-chloro-7-methyl-6,7-dihydro-5H-benzocycloheptene-8-carboxylic acid (1.50 g, 6.34 mmol), N,N'-carbonyldiimidazole (1.54 g, 9.51 mmol), guanidine hydrochloride (6.05 g, 63.4 mmol), sodium methoxide (3.42 g, 63.4 mmol) and N,N-dimethylformamide (25 ml).

Melting point: 142.5–145° C.

Example 30
Synthesis of N-(aminoiminomethyl)-3,7-dimethyl- 6,7-dihydro-5H-benzocycloheptene-8-carboxamide Methanesulfonate 1.00 Gram of N-(aminoiminomethyl)-3,7-dimethyl-6,7-dihydro-5H-benzocycloheptene-8-carboxamide methanesulfonate was obtained by carrying out reaction according to the method described in Example 8, except for using 3,7-dimethyl-6,7-dihydro-5H-benzocycloheptene-8-carboxylic acid (1.00 g, 4.62 mmol), N,N'-carbonyldiimidazole (1.13 g, 6.94 mmol), guanidine hydrochloride (8.83 g, 92.5 mmol), sodium methoxide (5.00 g, 92.5 mmol) and N,N-dimethylformamide (60 ml).

Melting point: 151–153° C.

Example 31
Synthesis of N-(aminoiminomethyl)-2,7-dimethyl-6,7-dihydro-5H-benzocycloheptene-8-carboxamide Methanesulfonate 2.59 Grams of N-(aminoiminomethyl)-2,7-dimethyl-6,7-dihydro-5H-benzocycloheptene-8-carboxamide methanesulfonate was obtained by carrying out reaction according to the method described in Example 8, except for using 2,7-dimethyl-6,7-dihydro-5H-benzocycloheptene-8-carboxylic acid (2.36 g, 10.9 mmol), N,N'-carbonyldiimidazole (2.68 g, 16.5 mmol), guanidine hydrochloride (10.5 g, 110 mmol), sodium methoxide (5.94 g, 110 mmol) and N,N-dimethylformamide (70 ml).

Melting point: 199° C.

TEST EXAMPLE
Inhibitory Effect on the $Na^+/H^+$ Exchange Transport System (In Vitro)

Test Method

A test was carried out according to the method of Iemori et al. (J. Hypertension, 8, 153(1990)). In detail, inhibitory effect on the $Na^+/H^+$ exchange transport system was evaluated by using as an indication a pH change in isolated ventricular myocytes (rat) under an acid load.

Test Results

| Example | Inhibitory effect on Na+/H+ exchange transport system $IC_{50}$ ($\mu M$) |
|---|---|
| 1 | 0.3 |
| 2 | 0.1 |
| 3 | 0.05 |
| 4 | 3.3 |
| 5 | 0.15 |
| 6 | 0.07 |
| 7 | 0.05 |
| 8 | 7.1 |
| 9 | 2.3 |
| 10 | 0.01 |
| 11 | 0.21 |
| 12 | 0.46 |
| 13 | >10 |

| Example | Inhibitory effect on Na+/H+ exchange transport system $IC_{50}$ ($\mu M$) |
|---|---|
| 14 | 0.03 |
| 15 | 0.03 |

INDUSTRIAL APPLICABILITY

The compounds of the present invention, prodrugs thereof and pharmaceutically acceptable salts of the compounds or prodrugs inhibit the sodium/proton ($Na^+/H^+$) exchange transport system and hence are useful as a therapeutic or prophylactic agent for diseases caused by the acceleration of the sodium/proton ($Na^+/H^+$) exchange transport system, for example, hypertension, arrhythmia, angina pectoris, cardiac hypertrophy, diabetes mellitus, organ disorders associated with ischemia or ischemic reperfusion [e.g. cardiac ischemic reperfusion-injury, acute renal failure, or disorders induced by surgical treatment such as organ transplantation or percutaneous transluminal coronary angioplasty (PTCA)], cerebro-ischemic injury [e.g. injury associated with cerebral infarction, injury caused as sequelae of stroke, or brain edema], diseases caused by hyperplasia such as hyperplasia of fibroblast, hyperplasia of smooth muscle cells or hyperplasia of mesangium cells, which diseases are, for example, atherosclerosis, pulmonary fibrosis, hepatic fibrosis, renal fibrosis, glomerular nephrosclerosis, organ hypertrophy, prostatic hypertrophy, diabetic complications or restenosis after PTCA, or diseases caused by endotherial cell injury.

What is claimed is:
1. A compound represented by the formula (1):

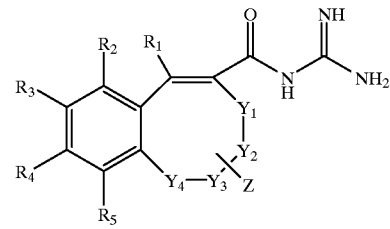

(1)

wherein $R_1$ is a hydrogen atom, an alkyl group, a substituted alkyl group, an alkenyl group, an alkynyl group, a cycloalkyl group, a cycloalkenyl group, a saturated heterocyclic group, an aromatic group, an acyl group, a halogen atom, $-OR_6$, $-S(O)_nR_7$, $-Q-Ra$ or

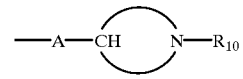

wherein A is an oxygen atom or $-S(O)_n-$, $R_{10}$ is a hydrogen atom, an alkyl group, a substituted alkyl group, an acyl group, $-S(O)_nR_7$ or $-Q-Ra$, and the ring is a 3- to 8-membered saturated heterocyclic group composed of a nitrogen atom and carbon atoms;

$R_2$, $R_3$, $R_4$ and $R_5$ are independently a hydrogen atom, an alkyl group, a substituted alkyl group, an alkenyl group, an alkynyl group, a cycloalkyl group, a cycloalkenyl group, a saturated heterocyclic group, an aromatic group, an acyl group, a carboxyl group, an alkoxycarbonyl group, a halogen atom, a nitro group, —OR$_6$, —N(R$_8$)R$_9$, —CON(R$_8$)R$_9$, —SO$_2$N(R$_8$)R$_9$, —S(O)$_n$R$_7$, —Q—Ra or

wherein A' is an oxygen atom, —S(O)$_n$— or —N(R$_{51}$)—, and R$_{10}$ and the ring are as defined above;

Y$_1$, Y$_2$, Y$_3$ and Y$_4$, which may be the same or different, are independently a single bond, —CH$_2$—, —CO—, or —C(=C(R$_{12}$)R$_{13}$)— provided that at least two of Y$_1$ through Y$_4$ are independently a group other than a single bond;

Z may be absent, or one or more Zs may be present and are, the same or different, independently the following substituent for a hydrogen atom bonded to any of the carbon atoms constituting the ring formed by Y$_1$ through Y$_4$, an alkyl group, a substituted alkyl group, an alkenyl group, an alkynyl group, a cycloalkyl group, a cycloalkenyl group, a saturated heterocyclic group, a halogen atom, a carboxyl group, an alkoxy-carbonyl group, an aromatic group, an acyl group, —OR$_6$, —N(R$_8$)R$_9$, —S(O)$_n$R$_7$, —C(O)N(R$_8$)R$_9$, —SO$_2$N(R$_8$)R$_9$, or —Q—Ra;

Q is a substituted or unsubstituted lower alkylene group;

Ra is a substituted or unsubstituted vinyl group, or a substituted or unsubstituted ethynyl group;

R$_6$ is a hydrogen atom, an alkyl group, a substituted alkyl group, a cycloalkyl group, a cycloalkenyl group, a saturated heterocyclic group or an aromatic group;

R$_7$ is an alkyl group, a substituted alkyl group or an aromatic group;

n is an integer of 0, 1 or 2;

R$_8$ and R$_9$ are independently a hydrogen atom, an alkyl group, a substituted alkyl group, a cycloalkyl group, a cycloalkenyl group, a saturated heterocyclic group, an aromatic group, an acyl group, —S(O)$_2$R$_7$ or —Q—Ra, or R$_8$ and R$_9$, when taken together with the nitrogen atom to which they are bonded, form a 5- to 7-membered saturated cyclic amino group which may contain other heteroatom(s) in the ring and may be substituted by one or more alkyl groups, substituted alkyl groups, hydroxyl groups or —OR$_6$ groups;

R$_{11}$ is a hydrogen atom, an alkyl group, a substituted alkyl group, a cycloalkyl group, a saturated heterocyclic group, an aromatic group, an acyl group, —S(O)$_2$R$_7$ or —Q—Ra;

R$_{51}$ is a hydrogen atom, an alkyl group, a substituted alkyl group, a cycloalkyl group, a saturated heterocyclic group, an aromatic group, an acyl group, —S(O)$_2$R$_7$ or —Q—Ra; and R$_{12}$ and R$_{13}$ are independently a hydrogen atom, an alkyl group, a substituted alkyl group, an alkenyl group, an alkynyl group, a cycloalkyl group, a cycloalkenyl group, a saturated heterocyclic group, a halogen atom, a carboxyl group, an alkoxycarbonyl group, an aromatic group, an acyl group, —OR$_6$, —CON(R$_8$)R$_9$, —S(O)$_n$R$_7$ or —Q—Ra, a prodrug of said compound, or a pharmaceutically acceptable salt of said compound or prodrug; wherein the alkyl group is a linear or a branched alkyl group of 8 or less carbon atoms;

the cycloalkyl group is either an unsubstituted one or a substituted one having as the substituent(s); 1 to 4 alkyl group(s), substituted alkyl group(s), hydroxyl group(s) or —OR$_6$ group(s), and is a 3- to 8-membered cycloalkyl group;

the cycloalkenyl group is either an unsubstituted one or a substituted one having as the substituent(s); 1 to 4 alkyl group(s), substituted alkyl group(s), hydroxyl group(s) or —OR$_6$ group(s), and is a 3- to 8-membered cyoloalkenyl group having a double bond;

the saturated heterocyclic group is either an unsubstituted one or a substituted one having as the substituent(s); 1 to 4 alkyl group(s), substituted alkyl group(s), hydroxyl group(s), or —OR$_6$ group(s), and is a 3- to 8-membered saturated heterocyclic group having an oxygen atom or a sulfur atom;

the alkoxycarbonyl group is a linear or branched alkoxycarbonyl group of 6 or less carbon atoms;

the aromatic group is a substituted or unsubstituted aryl group, or a substituted or unsubstituted heteroaryl group, wherein the aryl group is 10 or less carbon atoms, and the heteroaryl group is a 5- or 6-membered heteroaryl group containing 1 to 4 nitrogen atoms or a 5- to 6-membered heteroaryl group containing 0 to 2 nitrogen atoms and an oxygen atom or a sulfur atom;

the substituent of each of the substituted aryl group and the substituted heteroaryl group is an alkyl group, a substituted alkyl group, a halogen atom, a nitro group, an alkoxycarbonyl group , a carboxyl group, and a group represented by the formula —OR$_6$, —N(R$_8$)R$_9$, —CON(R$_8$)R$_9$, —SO$_2$N(R$_8$)R$_9$ or —S(O)$_n$R$_7$;

the 5- to 7-membered cyclic amino group is a 5- to 7-membered ring group containing 1 to 3 nitrogen atoms or a 5- to 7-membered ring group containing a nitrogen atom and an oxygen atom;

the substituent of the substituted alkyl group is a halogen atom, a hydroxyl group, an alkoxy group, a cycloalkyl group, a cyano group, a carboxy group, an alkoxycarbonyl group, an acyl group, an aromatic group, and a group represented by the formula —CONRpRq wherein Rp and Rq is independently a hydrogen atom or an alkyl group, or Rp and Rq, when taken together, represent a 5- to 7-membered saturated cyclic amino group which may contain another heteroatom; —N(R$_8$)R$_9$; or

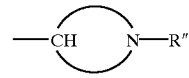

wherein R" is a hydrogen atom, an alkyl group or a substituted alkyl group, and the ring is a 3- to 8-membered saturated heterocyclic group composed of a nitrogen atom and carbon atoms, the substituent of each of the lower alkylene group and the vinyl or ethynyl group is an alkyl group, a substituted alkyl group, a cycloalkyl group, a cycloalkenyl group, a saturated heterocyclic group, a carboxyl group, an alkoxycarbonyl group, an aromatic group, and a group represented by the formula —CON(R$_8$)R$_9$;

the lower alkylene group is an alkylene group of 6 or less carbon atoms;

the acyl group is a formyl group, an alkanoyl group of 2 to 6 carbon atoms, a cycloalkanecarbonyl group of 4 to 7 carbon atoms, a cycloalkenecarbonyl group of 3 to 6 carbon atoms, an aroyl group of 6 to 10 carbon atoms, a saturated heterocyclic ring-carbonyl group having a 5- or 6-membered saturated heterocyclic ring containing one or two heteroatoms selected from nitrogen atom, oxygen atom, and sulfur atom; or a heteroaromatic acyl group having a 5- or 6-membered heteroaromatic ring containing one or two heteroatoms selected from nitrogen atom, oxygen atom and sulfur atom;

the alkenyl group is an alkenyl group of 6 or less carbon atoms; and the alkynyl group is an alkynyl group of 6 or less carbon atoms.

2. A compound, a prodrug thereof or a pharmaceutically acceptable salt of the compound or prodrug according to claim 1, wherein $Y_1$, $Y_2$, $Y_3$ and $Y_4$, which may be the same or different, are independently a single bond, —$CH_2$—, —CO—, or —C(=C($R_{12}$)$R_{13}$)—.

3. A compound, a prodrug thereof or a pharmaceutically acceptable salt of the compound or prodrug according to claim 1, wherein one or two of $Y_1$ through $Y_4$ is a single bond, and the others are independently a group other than a single bond.

4. A compound, a prodrug thereof or a pharmaceutically acceptable salt of the compound or prodrug according to claim 2, wherein one or two of $Y_1$ through $Y_4$ is a single bond, and the others are independently a group other than a single bond.

5. A compound, a prodrug thereof or a pharmaceutically acceptable salt of the compound or prodrug according to claim 1, wherein one of $Y_1$ through $Y_4$ is a single bond, and the others are independently a group other than a single bond.

6. A compound, a prodrug thereof or a pharmaceutically acceptable salt of the compound or prodrug according to claim 2, wherein one of $Y_1$ through $Y_4$ is a single bond, and the others are independently a group other than a single bond.

7. A compound, a prodrug thereof or a pharmaceutically acceptable salt of the compound or prodrug according to claim 5, wherein Z is an alkyl group or a substituted alkyl group.

8. A compound, a prodrug thereof or a pharmaceutically acceptable salt of the compound or prodrug according to claim 5 or claim 7, wherein each of Y1, Y2 and Y3 is —CH2— which may be substituted by one Z or two or more Zs which may be the same or different, and Y4 is a single bond.

9. A compound, a prodrug thereof or a pharmaceutically acceptable salt of the compound or prodrug according to claim 8, wherein one of $Y_1$, $Y_2$ and $Y_3$ is —$CH_2$— substituted by one Z or two Zs which may be the same or different, and the two others are independently unsubstituted —$CH_2$—, and $Y_4$ is a single bond.

10. A compound, a prodrug thereof or a pharmaceutically acceptable salt of the compound or prodrug according to claim 8, wherein $Y_1$ is —$CH_2$— substituted by one Z or two Zs which may be the same or different, $Y_2$ and $Y_3$ are independently unsubstituted —$CH_2$—, and $Y_4$ is a single bond.

11. A compound, a prodrug thereof or a pharmaceutically acceptable salt of the compound or prodrug according to claim 8, wherein $Y_3$ is —$CH_2$— substituted by one Z or two Zs which may be the same or different, $Y_1$ and $Y_2$ are independently unsubstituted —$CH_2$—, and $Y_4$ is a single bond.

12. A compound, a prodrug thereof or a pharmaceutically acceptable salt of the compound or prodrug according to any one of claims 1 to 11, wherein one of $R_2$, $R_3$, $R_4$ and $R_5$ is a substituted alkyl group, an alkenyl group, an alkynyl group, a cycloalkyl group, a cycloalkenyl group, an acyl group, a carboxyl group, an alkoxycarbonyl group, —CON($R_8$)$R_9$, —$SO_2$N($R_8$)$R_9$, —S(O)$_n$$R_7$, —Q—Ra or

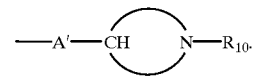

13. A compound, a prodrug thereof or a pharmaceutically acceptable salt of the compound or prodrug according to any one of claims 1 to 12, wherein at least one Z is present.

14. N-(aminoiminomethyl)-7-methyl-6,7-dihydro-5H-benzocycloheptene-8-carboxamide or N-(aminoiminomethyl)-7,7-dimethyl-6,7-dihydro-5H-benzocycloheptene-8-carboxamide, a prodrug thereof, or a pharmaceutically acceptable salt of any one of these compounds or prodrugs.

15. A process for producing a compound of the formula (1), a prodrug thereof or a pharmaceutically acceptable salt of the compound or prodrug according to claim 1, which comprises reacting a compound represented by the formula (2):

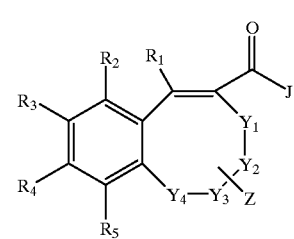

(2)

wherein $R_1$, $R_2$, $R_3$, $R_4$, $R_5$, $Y_1$, $Y_2$, $Y_3$, $Y_4$ and Z are as defined in claim 1, and J is a hydroxyl group or a leaving group replaceable by a nucleophilic reagent, with guanidine.

16. A pharmaceutical composition comprising a compound, a prodrug thereof or a pharmaceutically acceptable salt of the compound or prodrug according to any one of claims 1 to 13 or 14.

17. A sodium/proton exchange transport system inhibitor comprising the compound, a prodrug thereof or a pharmaceutically acceptable salt of the compound or prodrug according to any one of claims 1 to 13 or 14, as an active ingredient.

18. A pharmaceutical composition for the treatment or prophylaxis of hypertension, arrhythmia, angina pectoris, cardiac hypertrophy, diabetes mellitus, organ disorders associated with ischemia or ischemic reperfusion, cerebro-ischemic disorders, diseases caused by excessive cell proliferation, or diseases caused by endothelial cell injury, which comprises a compound, a prodrug thereof or a pharmaceutically acceptable salt of the compound or prodrug according to any one of claims 1 to 13 or 14.

* * * * *